United States Patent
Grzybowski et al.

(10) Patent No.: US 10,442,888 B2
(45) Date of Patent: Oct. 15, 2019

(54) POLYMERS AND COMPOUNDS BASED ON DIPYRROLO[1,2-B:1',2'-G][2,6]NAPHTHYRIDINE-5,11-DIONE

(71) Applicant: BASF SE, Ludwigshafen am Rhein (DE)

(72) Inventors: Marek Grzybowski, Szczecin (PL); Daniel T. Gryko, Warsaw (PL); Bartlomiej Sadowski, Pomiechowek (PL); Karen Strassel, Freiburg (DE); Pascal Hayoz, Hofstettn (CH); Daniel Kaelblein, Speyer (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/765,525

(22) PCT Filed: Oct. 20, 2016

(86) PCT No.: PCT/EP2016/075141
§ 371 (c)(1),
(2) Date: Apr. 3, 2018

(87) PCT Pub. No.: WO2017/068009
PCT Pub. Date: Apr. 27, 2017

(65) Prior Publication Data
US 2019/0077907 A1    Mar. 14, 2019

(30) Foreign Application Priority Data
Oct. 21, 2015 (EP) .................................. 15190894

(51) Int. Cl.
*C08G 61/12* (2006.01)
*C07D 471/22* (2006.01)
(Continued)

(52) U.S. Cl.
CPC ......... *C08G 61/126* (2013.01); *C07D 471/22* (2013.01); *C08G 61/124* (2013.01);
(Continued)

(58) Field of Classification Search
CPC ............... C08G 61/126; C08G 61/124; C08G 2261/3246; C08G 2261/1412;
(Continued)

(56) References Cited

U.S. PATENT DOCUMENTS

| 6,690,029 B1 | 2/2004 | Anthony et al. |
| 2006/0013549 A1 | 1/2006 | Shtein et al. |

(Continued)

FOREIGN PATENT DOCUMENTS

| WO | 03/052841 A1 | 6/2003 |
| WO | 2004/112161 A2 | 12/2004 |

(Continued)

OTHER PUBLICATIONS

Extended European Search Report dated Jan. 22. 2016 in Patent Application No. 15190894.4.

(Continued)

*Primary Examiner* — Shane Fang
(74) *Attorney, Agent, or Firm* — Oblon, McClelland, Maier & Neustadt, L.L.P.

(57) ABSTRACT

Polymers containing a repeating unit of the formula —[Ar—Y—Ar']— (V), and compounds of formula $R^{10}$—Ar—Y—Ar'—$R^{10'}$ (I), where Y is a group of formula (Continued)

and organic devices containing the polymers. The polymers and compounds have excellent solubility in organic solvents and excellent film-forming properties. In addition, high efficiency of energy conversion, excellent field-effect mobility, good on/off current ratios and/or excellent stability can be observed, when the polymers and compounds are used in organic field effect transistors, organic photovoltaics and photodiodes.

24 Claims, 1 Drawing Sheet

(51) Int. Cl.
*H01B 1/12* (2006.01)
*H01L 51/00* (2006.01)
*H01L 51/05* (2006.01)
*H01L 51/42* (2006.01)

(52) U.S. Cl.
CPC ............ *H01B 1/12* (2013.01); *H01B 1/128* (2013.01); *H01L 51/0035* (2013.01); *H01L 51/0036* (2013.01); *H01L 51/0043* (2013.01); *H01L 51/0072* (2013.01); *H01L 51/0074* (2013.01); *H01L 51/0541* (2013.01); *C08G 2261/1412* (2013.01); *C08G 2261/3241* (2013.01); *C08G 2261/3244* (2013.01); *C08G 2261/3246* (2013.01); *H01L 51/0558* (2013.01); *H01L 51/4253* (2013.01); *Y02E 10/549* (2013.01)

(58) Field of Classification Search
CPC .... C08G 2261/3241; C08G 2261/3244; C07D 471/22; H01L 51/0036; H01L 51/0072; H01L 51/0043; H01L 51/0074; H01L 51/0558; H01L 51/4253; H01B 1/128; H01B 1/12; Y02E 10/549
See application file for complete search history.

(56) References Cited

U.S. PATENT DOCUMENTS

| | | |
|---|---|---|
| 2007/0079867 A1 | 4/2007 | Chittibabu et al. |
| 2014/0302637 A1 | 10/2014 | Hayoz et al. |
| 2015/0144846 A1* | 5/2015 | Nanson ............... H01L 51/0036 252/500 |
| 2016/0049588 A1 | 2/2016 | Hayoz et al. |

FOREIGN PATENT DOCUMENTS

| | | |
|---|---|---|
| WO | 2007/082584 A1 | 7/2007 |
| WO | 2008/001123 A1 | 1/2008 |
| WO | 2008/107089 A1 | 9/2008 |
| WO | 2009/047104 A2 | 4/2009 |
| WO | 2010/108873 A1 | 9/2010 |
| WO | 2010/136352 A1 | 12/2010 |
| WO | 2013/050401 A2 | 4/2013 |
| WO | 2014/072292 A2 | 5/2014 |

OTHER PUBLICATIONS

Marek Grzybowski, et al., "Dipyrrolonaphthyridinediones—structurally unique cross-conjugated dyes", Chemical Communications, vol. 52, No. 29, 2016, pp. 5108-5111.
U.S. Appl. No. 14/770,867, filed Mar. 14, 2017, U.S. Pat. No. 9,595,680 A, Daniel T. Gryko, et al.
U.S. Appl. No. 15/414,060, filed Feb. 13, 2018, U.S. Pat. No. 9,893,302 A, Daniel T. Gryko, et al.
U.S. Appl. No. 15/324,548, filed Jan. 6, 2017, US 2017-0207392 A1, Ian McCulloch, et al.
U.S. Appl. No. 15/503,242, filed Feb. 10, 2017, US 2017-0229657 A1, Zhenan Bao, et al.
U.S. Appl. No. 15/514,180, filed Mar. 24, 2017, US 2017-0250358 A1, Emmanuel Martin, et al.
U.S. Appl. No. 15/318,566, filed Dec. 13, 2016, US 2017-0117479 A1, Thomas Gessner, et al.
U.S. Appl. No. 15/543,637, filed Jul. 14, 2017 US 2018-0009936 A1, Pascal Hayoz, et al.
International Search Report dated Dec. 14, 2016, in PCT/EP2016/075141, filed Oct. 20, 2016.

* cited by examiner

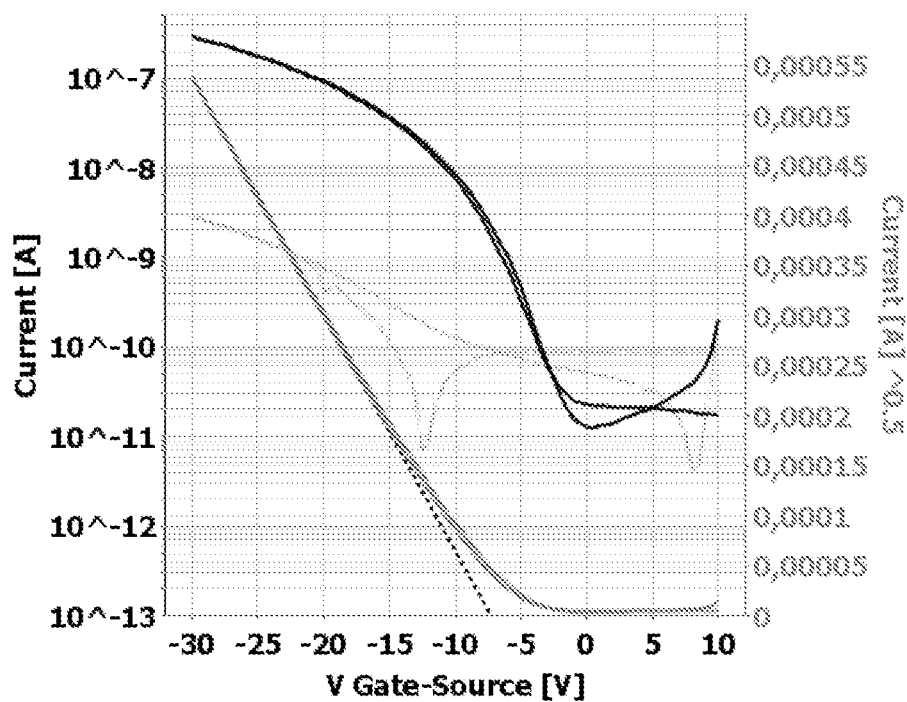

POLYMERS AND COMPOUNDS BASED ON DIPYRROLO[1,2-B:1',2'-G][2,6]NAPHTHYRIDINE-5,11-DIONE

The present invention relates to polymers comprising a repeating unit of the formula (V), and compounds of formula (I) and their use as organic semiconductor in organic devices, especially in organic photovoltaics and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics and photodiodes.

Daniel D. Gryko et al., Chem. Commun., 2016, 52, 5108 [publication date: Mar. 31, 2016] reports the synthesis of red-emissive dyes based on dipyrrolo[1,2-b:10,20-g][2,6]naphthyridine-5,11-dione (DPND) having intense fluorescence in the range of 520-740 nm.

Photophysical properties of DPND dyes measured in dichloromethane are shown in Tab. 2:

| Dye | $\lambda^{max}_{abs}$ [nm] | $\varepsilon_{max}$ [M$^{-1}$ cm$^{-1}$] | $\lambda^{max}_{em}$ [nm] | $\theta_{fl}$ | $\delta_v^a$ [cm$^{-1}$] |
|---|---|---|---|---|---|
| 1a | 509 | 26600 | 535 | 0.61[b] | 950 |
| 1b | 499 | 29200 | 523 | 0.66[b] | 900 |
| 1c | 504 | 29300 | 528 | 0.71[b] | 900 |
| 1d | 505 | 23100 | 543 | 0.58[b] | 1400 |
| 1e | 510 | 28300 | 536 | 0.26[b] | 950 |
| 1f | 500 | 28000 | 526 | 0.67[b] | 1000 |
| 4 | 503 | 24600 | 601 | 0.46[b] | 3240 |
| 5 | 520 | 34200 | 549 | 0.21[b] | 1000 |
| 6 | 517 | 34600 | 537 | 0.25[b] | 720 |
| 7a | 599 | 57300 | 633 | 0.51[c] | 900 |
| 7b | 584 | 47400 | 616 | 0.51[c] | 900 |
| 7c | 601 | 52400 | 643 | 0.59[c] | 1100 |
| 7d | 645 | 56600 | 736 | 0.17[c] | 1900 |

[a]Stokes shift i.e. the difference between the lowest energy absorption band and the highest energy emission band expressed in cm$^{-1}$.
[b]Reference: rhodamine 6G in EtOH ($\theta_{fl}$ = 0.94).
[c]Reference: cresyl violet in MeOH ($\theta_{fl}$ = 0.54).

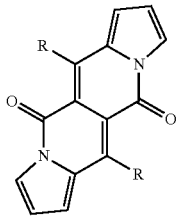

1a, R = H
1b, R = CH$_3$
1c, R = C$_7$H$_{15}$
1d, R = sec-Butyl
1e, R = 4-Methoxybenzyl
1f, R = C$_2$H$_5$,

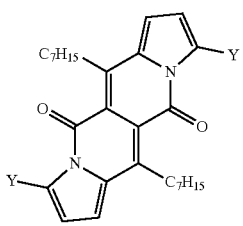

4, Y = COCF$_3$
5, Y = Br
6, Y = CN,

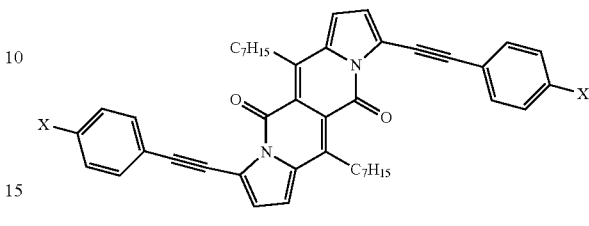

7a, X = NO$_2$
7b, X = CF$_3$
7c, X = OCH$_3$
7d, X = N(CH$_3$)$_2$.

All compounds 1a-f show intense structured absorption bands with the maxima at around 500 nm and the molecular absorption coefficients ranging from 24 000 to 29 000 M$^{-1}$ cm$^{-1}$. Except for 1e, all of the samples show good fluorescence quantum yields (0.58-0.71) and small Stokes shifts (~1000 cm$^{-1}$). The presence of phenylethynyl substituents in dyes 7a-d caused a large bathochromic shift of the absorption by 80-140 nm in comparison with the starting DPND 1c.

WO08107089 relates to silylethynylated heteroacenes and formulations and electronic devices made with those compounds.

WO13050401 relates to polymers comprising one or more (repeating) unit(s) of the formula

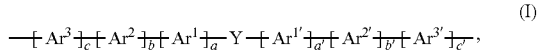

and compounds of formula

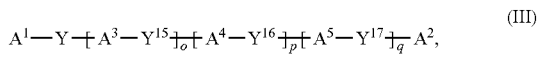

wherein Y, Y$^{15}$, Y$^{16}$ and Y$^{17}$ are independently of each other a group of formula

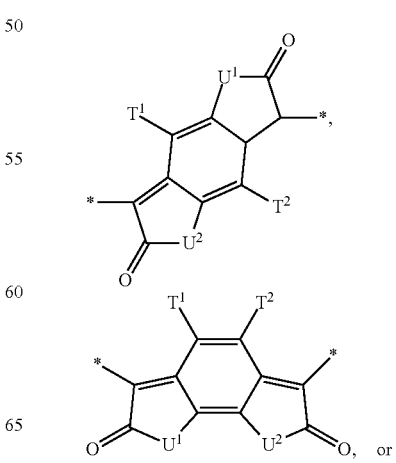

O, or

-continued

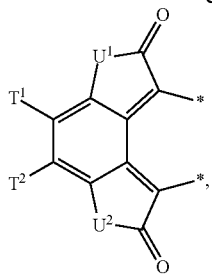

and their use as IR absorber, organic semiconductor in organic devices, especially in organic photovoltaics and photodiodes, or in a device containing a diode and/or an organic field effect transistor.

WO14072292 relates to polymers comprising one or more (repeating) unit(s) of the formula

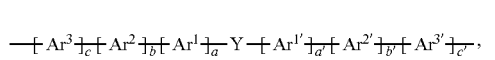 (I)

and compounds of formula

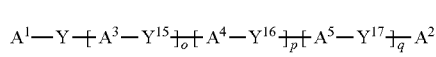 (III)

wherein Y, $Y^{15}$, $Y^{16}$ and $Y^{17}$ are independently of each other a group of formula

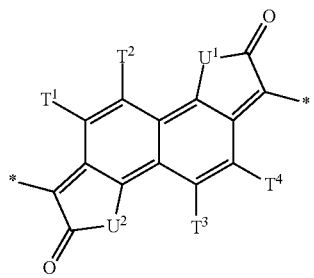

and their use as IR absorber, organic semiconductor in organic devices, especially in organic photovoltaics and photodiodes, or in a device containing a diode and/or an organic field effect transistor.

The present invention relates to compounds of formula $R^{10}$—Ar—Y—Ar'—$R^{10'}$ (I), wherein Ar is a group of formula —$[Ar^3]_c$—$[Ar^2]_b$—$[Ar^1]_a$—**,
Ar' is a group of formula **—$[Ar^{1'}]_{a'}$—$[Ar^{2'}]_{b'}$—$[Ar^{3'}]_{c'}$—,

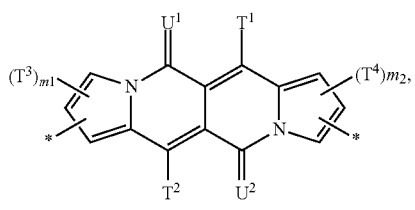

Y is a group of formula
** indicates the bonding to Y,
a is 0, 1, 2, or 3; a' is 0, 1, 2, or 3; b is 0, 1, 2, or 3; b' is 0, 1, 2, or 3; c is 0, 1, 2, or 3; c' is 0, 1, 2, or 3; m1 is 0, 1, or 2, m2 is 0, 1, or 2,
$U^1$ is O, or S,
$U^2$ is O, or S,
$T^1$, $T^2$, $T^3$ and $T^4$ are independently of each other hydrogen, halogen, cyano, —$COOR^{103}$, —$OCOR^{103}$, —$NR^{112}COR^{103}$, —$CONR^{112}R^{113}$, —$OR^{103'}$, —$SR^{103'}$, —$SOR^{103'}$, —$SO_2R^{103'}$, —$NR^{112}SO_2R^{103'}$, —$NR^{112}R^{113}$, —$NO_2$, $C_7$-$C_{25}$arylalkyl, which can be substituted one to three times with $C_1$-$C_8$alkyl and/or $C_1$-$C_8$alkoxy;
a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_2$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$;
a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$;
a —CO—$C_1$-$C_{18}$alkyl group, a —CO—$C_5$-$C_{12}$cycloalkyl group, or —COO—$C_1$-$C_{18}$alkyl group;
$Ar^1$ and $Ar^{1'}$ are independently of each other

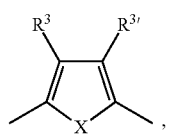 (XIa)

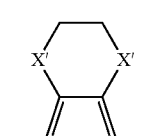 (XIb)

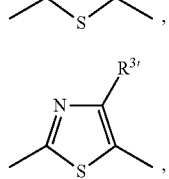 (XIc)

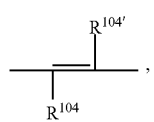 (XId)
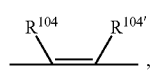 (XIe)
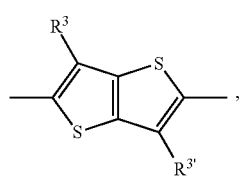 (XIf)
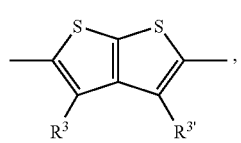 (XIg)
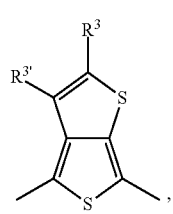 (XIh)
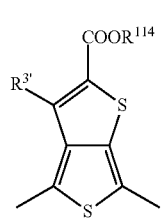 (XIi)
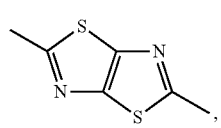 (XIj)
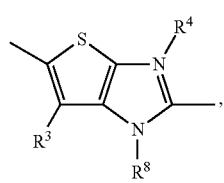 (XIk)
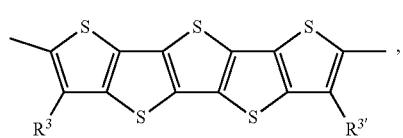 (XIl)
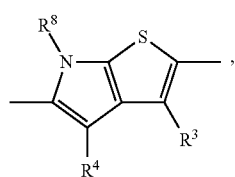 (XIm)
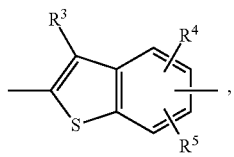 (XIn)
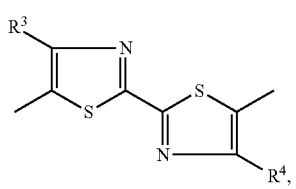 (XIo)
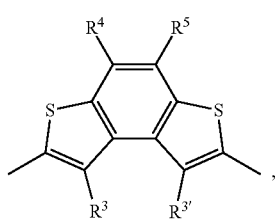 (XIp)
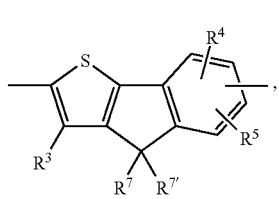 (XIq)
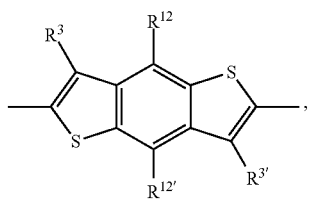 (XIr)
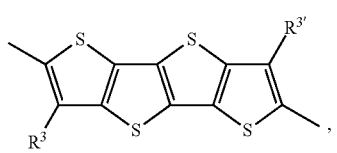 (XIs)
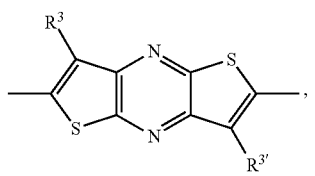 (XIt)
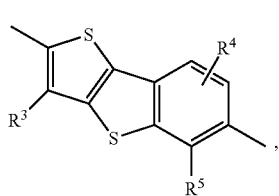 (XIu)

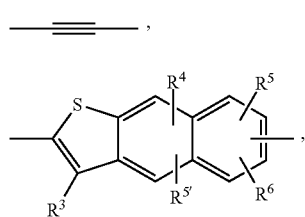 (XIw),
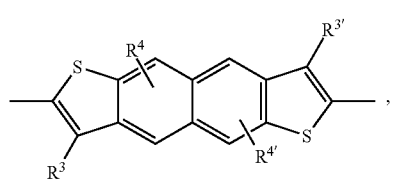 (XIx),
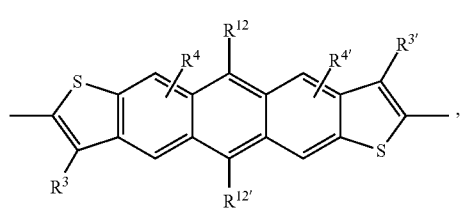 (XIy),
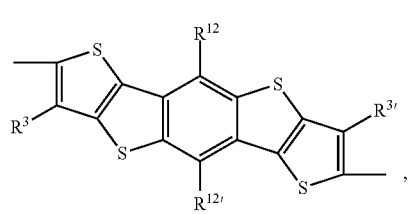 (XIIa),
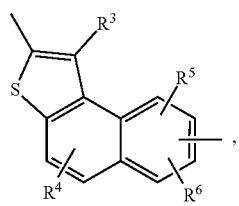 (XIIb),
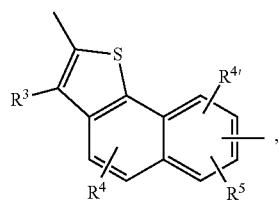 (XIIc),
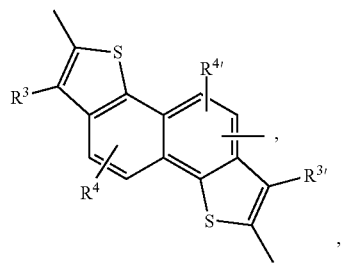 (XIId),
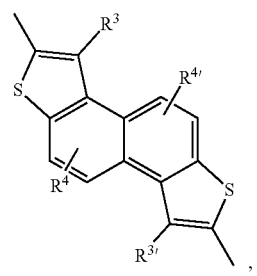 (XIIe),
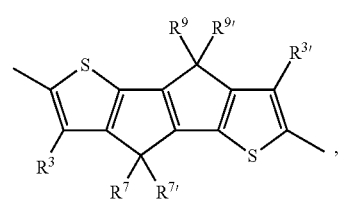 (XIIf),
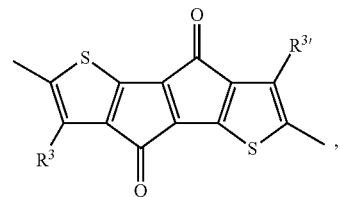 (XIIg),
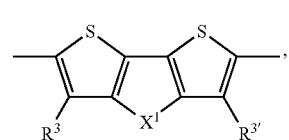 (XIIh),
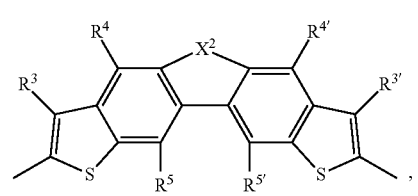 (XIIi),
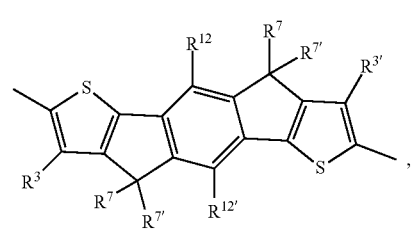 (XIIj),
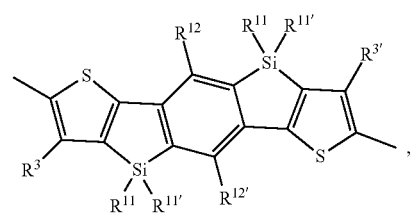 (XIIk),

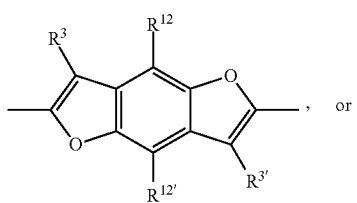  (XIII)
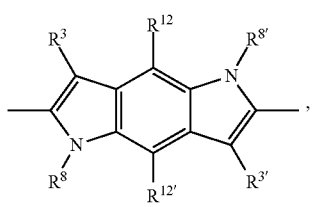  (XIIm)
Ar², Ar²', Ar³ and Ar³' have independently of each other the meaning of Ar¹, or are independently of each other
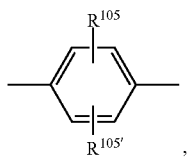  (XIIIa)
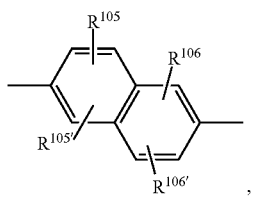  (XIIIb)
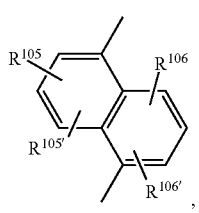  (XIIIc)
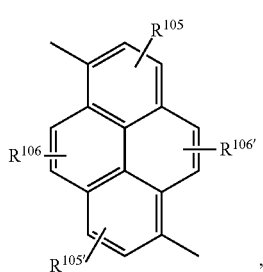  (XIIId)
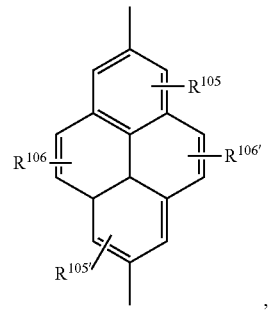  (XIIIe)
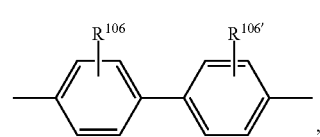  (XIIIf)
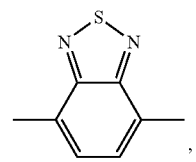  (XIIIg)
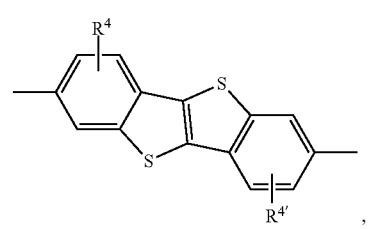  (XIIIh)
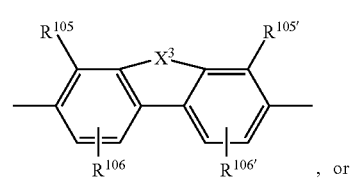  (XIIIi)
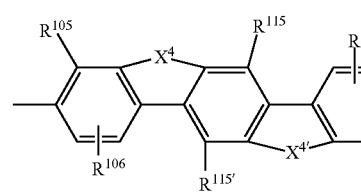  (XIIIj)
X is O, S, Se, Te, or NR⁸,
X' is O, or S,
$X^1$, $X^2$ and $X^3$ are independently of each other S, O, $NR^{107}$, $-Si(R^{117})(R^{117'})-$, $-Ge(R^{117})(R^{117'})-$, $-C(R^{108})(R^{109})-$, $-C(=O)-$, $-C(=CR^{110}R^{111})-$,
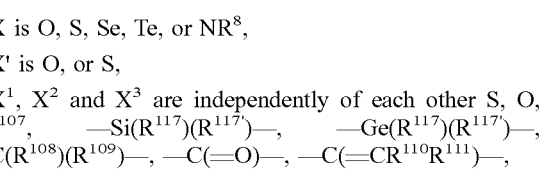
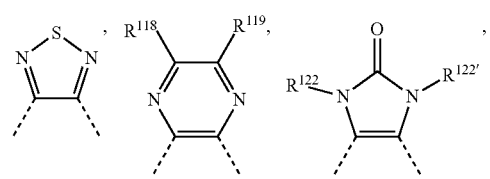

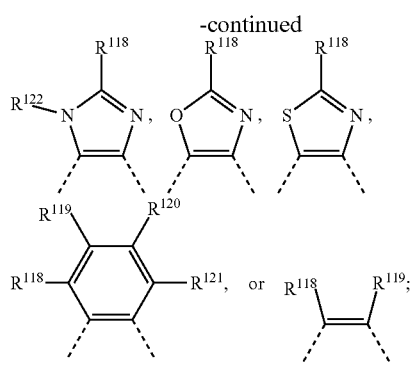

X⁴ and X⁴' are independently of each other S, O, NR¹⁰⁷—, —Si(R¹¹⁷)(R¹¹⁷')—, —Ge(R¹¹⁷)(R¹¹⁷')—, —C(R¹⁰⁸)(R¹⁰⁹)—, —C(=O)—, —C(=CR¹¹⁰R¹¹¹)—, $R^3$ and $R^{3'}$ are independently of each other hydrogen, halogen, halogenated $C_1$-$C_{25}$alkyl, especially $CF_3$, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^4$, $R^{4'}$, $R^5$, $R^{5'}$, $R^6$, and $R^{6'}$ are independently of each other hydrogen, halogen, halogenated $C_1$-$C_{25}$alkyl, especially $CF_3$, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^7$, $R^{7'}$, $R^9$ and $R^{9'}$ are independently of each other hydrogen, $C_1$-$C_{25}$alkyl, which may optionally be interrupted by one, or more oxygen, or sulphur atoms; or $C_7$-$C_{25}$arylalkyl, $R^8$ and $R^{8'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, $R^{10}$ and $R^{10'}$ are independently of each other hydrogen, halogen, $NO_2$, $NR^{112}R^{113}$, cyano, $C_1$-$C_{25}$alkyl, $C_1$-$C_{25}$alkyl which is substituted one or more times by E ($CF_3$) and/or interrupted one or more times by D,

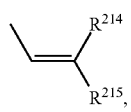

COO—$C_1$-$C_{18}$alkyl, $C_4$-$C_{18}$cycloalkyl group, $C_4$-$C_{18}$cycloalkyl group, which is substituted by G, $C_2$-$C_{18}$alkenyl, $C_2$-$C_{18}$alkynyl, $C_1$-$C_{18}$alkylthio, $C_1$-$C_{18}$alkoxy, $C_1$-$C_{18}$alkoxy which is substituted by E and/or interrupted by D, $C_7$-$C_{25}$aralkyl, $C_7$-$C_{25}$aralkyl, which is substituted by G, or a group of formulae IVa to IVk,

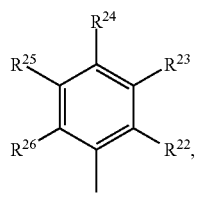 (IVa)

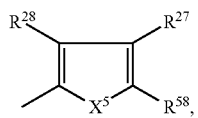 (IVb)

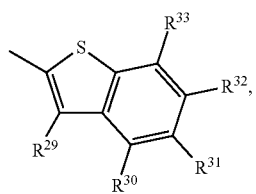 (IVc)

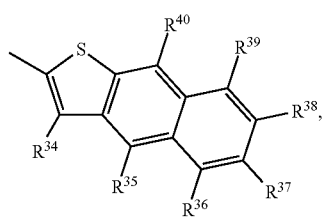 (IVd)

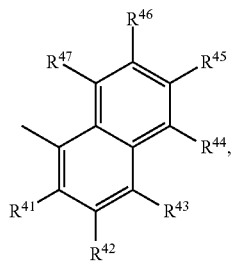 (IVe)

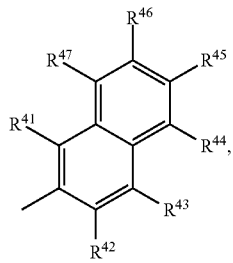 (IVf)

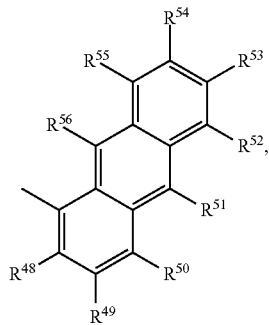 (IVg)

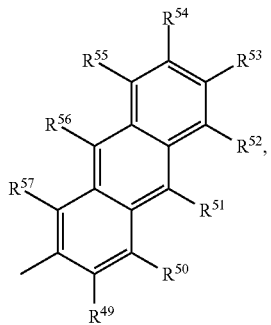

(IVh)

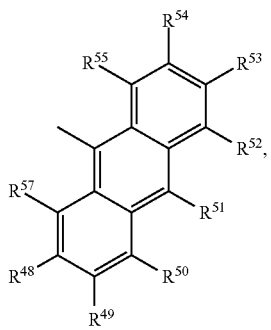

(IVi)

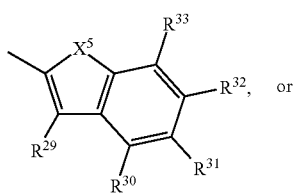

(IVj)

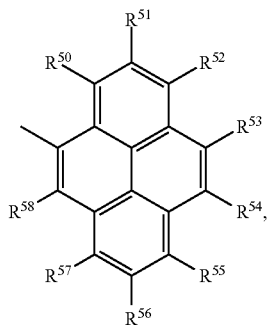

(IVk)

$X^5$ is O, S, Se, Te, or $NR^{59}$, $R^{11}$ and $R^{11'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

$R^{13}$ is a $C_1$-$C_{10}$alkyl group, or a tri($C_1$-$C_8$alkyl)silyl group;
$R^{22}$ to $R^{26}$ and $R^{29}$ to $R^{58}$ represent independently of each other H, halogen, cyano, $NO_2$, $NR^{112}R^{113}$, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{25}$alkylthio, $C_1$-$C_{25}$alkoxy, $C_1$-$C_{25}$alkoxy which is substituted by E and/or interrupted by D, $C_7$-$C_{25}$aralkyl, or $C_7$-$C_{25}$aralkyl, which is substituted by G, $R^{27}$ and $R^{28}$ are independently of each other hydrogen, $C_1$-$C_{25}$alkyl, halogen, cyano or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms, $R^{59}$ is hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, $R^{60}$ is hydrogen, $C_1$-$C_{18}$haloalkyl, $C_1$-$C_{25}$alkyl, which may optionally be interrupted by one or more oxygen or sulphur atoms; $C_1$-$C_{18}$alkanoyl, or $C_7$-$C_{25}$arylalkyl, $R^{103}$ and $R^{103'}$ are independently of each other hydrogen, $C_1$-$C_{100}$alkyl, $C_1$-$C_{25}$alkyl substituted by E and/or interrupted with D, $C_2$-$C_{25}$alkenyl, $C_2$-$C_{25}$alkenyl substituted by E and/or interrupted with D, $C_7$-$C_{25}$arylalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^{104}$ and $R^{104'}$ are independently of each other hydrogen, CN, $C_1$-$C_{18}$alkyl, $C_6$-$C_{10}$aryl, which may optionally be substituted by G, or $C_2$-$C_8$heteroaryl, which may optionally be substituted by G, $R^{105}$, $R^{105'}$, $R^{106}$ and $R^{106'}$ are independently of each other hydrogen, halogen, cyano, $C_1$-$C_{25}$alkyl, which may optionally be interrupted by one or more oxygen or sulphur atoms; $C_7$-$C_{25}$arylalkyl, or $C_1$-$C_{18}$alkoxy, $R^{107}$ is hydrogen, $C_7$-$C_{25}$arylalkyl, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$perfluoroalkyl; $C_1$-$C_{25}$alkyl, which may be interrupted by —O—, or —S—; or —COOR$^{103}$; $R^{103}$ is as defined above;

$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{108}$ and $R^{109}$ together form a group of formula =$CR^{110}R^{111}$, wherein $R^{110}$ and $R^{111}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, D is —CO—, —COO—, —S—, —O—, or —NR$^{112}$—,
E is $C_1$-$C_{18}$alkylthio, $C_1$-$C_{18}$alkoxy, CN, —NR$^{112}$R$^{113}$, —CONR$^{112}$R$^{113}$, or halogen,
G is E, or $C_1$-$C_{18}$alkyl, and $R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{114}$ is $C_1$-$C_{25}$alkyl, which may optionally be interrupted by one, or more oxygen, or sulphur atoms, $R^{115}$ and $R^{115'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

—≡—$R^{116}$, $R^{116}$ is a $C_1$-$C_{10}$alkyl group, or a tri($C_1$-$C_8$alkyl)silyl group;

$R^{117}$ and $R^{117'}$ are independently of each other $C_1$-$C_{25}$alkyl group, especially a $C_1$-$C_8$alkyl group, $C_7$-$C_{25}$arylalkyl, or a phenyl group, which can be substituted one to three times with $C_1$-$C_8$alkyl and/or $C_1$-$C_8$alkoxy;

$R^{118}$, $R^{119}$, $R^{120}$ and $R^{121}$ are independently of each other hydrogen, halogen, halogenated $C_1$-$C_{25}$alkyl, especially $CF_3$, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl, and $R^{124}$ and $R^{124'}$ are independently of each other hydrogen, cyano, $COOR^{103}$, a $C_1$-$C_{25}$alkyl group, $C_6$-$C_{24}$aryl, or $C_2$-$C_{20}$heteroaryl, $E_{Si}$ is —$SiR^{161}R^{162}R^{163}$ or —O—$SiR^{161}R^{162}R^{163}$;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165})_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170})_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$alkyl, halogen, cyano or $C_1$-$C_{25}$alkoxy;

$R^{167}$ and $R^{168}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50;

$R^{214}$ and $R^{215}$ are independently of each other hydrogen, $C_1$-$C_{18}$alkyl, $C_6$-$C_{24}$aryl, $C_2$-$C_{20}$heteroaryl, —CN or $COOR^{216}$; and $R^{216}$ is $C_1$-$C_{25}$alkyl, $C_1$-$C_{25}$haloalkyl, $C_7$-$C_{25}$arylalkyl, $C_6$-$C_{24}$aryl or $C_2$-$C_{20}$heteroaryl.

The FIGURE shows representative transfer characteristics of an FET fabricated from polymer P9 with $V_{GS}$=10 V to −30 V at 0.5V step size with $V_{DS}$=−30V. Drain current (black solid curve), Gate current (dotted grey curve), Square root of drain current (grey solid curve), and fitted slope of square root (dashed black curve).

The compounds of formula (I) may be used as functional dyes in dye sensitized and bulk heterojunction solar cells, organic light-emitting diodes, photodiodes, organic field-effect transistors, fluorescence imaging, sensors and solid-state dye lasers.

The compounds of formula (I) may also show very strong fluorescence and two photon absorption. Owing to these features, these dyes are excellent candidates for application in such fields as: fluorescence imaging, detection of cations and colouring of artist's or industrial paints.

Y is preferably a group of formula

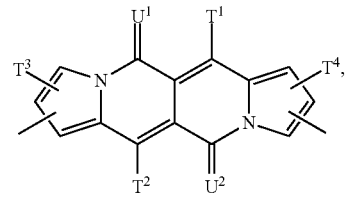

wherein $T^1$, $T^2$, $T^3$, $T^4$, $U^1$ and $U^2$ are defined above and below.

In a more preferred embodiment Y is a group of formula

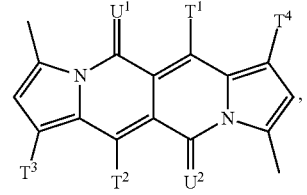

especially a group of formula

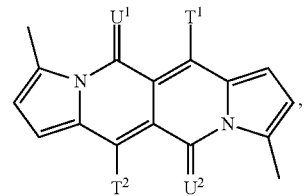

wherein $T^1$, $T^2$, $T^3$, $T^4$, $U^1$ and $U^2$ are defined above and below.

In another more preferred embodiment Y is a group of formula

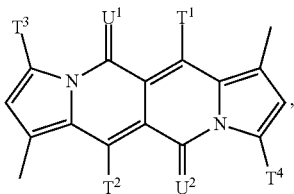

especially a group of formula

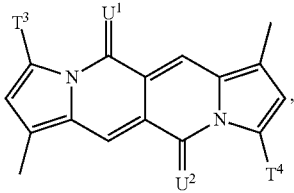

wherein $T^1$, $T^2$, $T^3$, $T^4$, $U^1$ and $U^2$ are defined above and below.

The compound of formula (I) is preferably a compound of formula

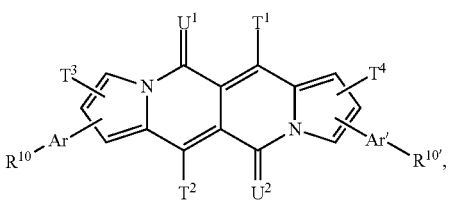

(Ia)

wherein $T^1$, $T^2$, $T^3$, $T^4$, $U^1$, $U^2$, Ar, Ar', $R^{10}$ and $R^{10'}$ are defined above and below.

The compound of formula (I) is more preferably a compound of formula

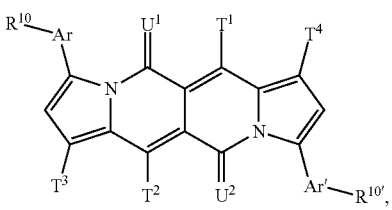

(Ia-1)

or a compound of formula

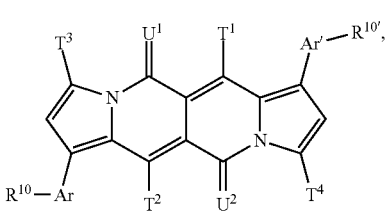

(Ia-2)

wherein $T^1$, $T^2$, $T^3$, $T^4$, $U^1$, $U^2$, Ar, Ar', $R^{10}$ and $R^{10'}$ are defined above and below.

$T^1$ and $T^2$ are preferably H, a $C_1$-$C_{38}$alkyl group which can optionally be substituted one or more times with $C_1$-$C_{12}$alkoxy, halogen, $C_5$-$C_{12}$cycloalkyl, cyano, or $E_{Si}$; and/or can optionally be interrupted by —O—, —S—, or —$NR^{60}$—, wherein $R^{60}$ is $C_1$-$C_{25}$alkyl, or phenyl$C_1$-$C_4$alkyl, which can be substituted one to three times with $C_1$-$C_8$alkyl and/or $C_1$-$C_8$alkoxy, wherein $E_{Si}$ is —$SiR^{161}R^{162}R^{163}$;

$R^{161}$, $R^{162}$ and $R^{163}$ are independently of each other $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—$SiR^{164}R^{165}R^{166}$, —(O—$SiR^{164}R^{165})_d$—$R^{166}$, or phenyl;

$R^{164}$, $R^{165}$ and $R^{166}$ are independently of each other $C_1$-$C_8$alkyl, $C_1$-$C_8$haloalkyl, $C_2$-$C_8$alkenyl, —O—$SiR^{169}R^{170}R^{171}$, —(O—$SiR^{169}R^{170})_d$—$R^{171}$, or phenyl;

$R^{169}$, $R^{170}$ and $R^{171}$ are independently of each other $C_1$-$C_8$alkyl, $C_1$-$C_8$haloalkyl, $C_2$-$C_8$alkenyl, —O—$Si(CH_3)_3$, or phenyl;

d is an integer from 1 to 10.

$T^3$ and $T^4$ are preferably H, a $C_1$-$C_{38}$alkyl group which can optionally be substituted one or more times with $C_1$-$C_{12}$alkoxy, halogen, $C_5$-$C_{12}$cycloalkyl, cyano, or $E_{Si}$; and/or can optionally be interrupted by —O—, —S—, or —$NR^{60}$—, wherein $R^{60}$ is $C_1$-$C_{25}$alkyl, or phenyl$C_1$-$C_4$alkyl, which can be substituted one to three times with $C_1$-$C_8$alkyl and/or $C_1$-$C_8$alkoxy, wherein $E_{Si}$ is —$SiR^{161}R^{162}R^{163}$;

$R^{161}$, $R^{162}$ and $R^{163}$ are independently of each other $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—$SiR^{164}R^{165}R^{166}$, —(O—$SiR^{164}R^{165})_d$—$R^{166}$, or phenyl;

$R^{164}$, $R^{165}$ and $R^{166}$ are independently of each other $C_1$-$C_8$alkyl, $C_1$-$C_8$haloalkyl, $C_2$-$C_8$alkenyl, —O—$SiR^{169}R^{170}R^{171}$, —(O—$SiR^{169}R^{170})_d$—$R^{171}$, or phenyl;

$R^{169}$, $R^{170}$ and $R^{171}$ are independently of each other $C_1$-$C_8$alkyl, $C_1$-$C_8$haloalkyl, $C_2$-$C_8$alkenyl, —O—$Si(CH_3)_3$, or phenyl;

d is an integer from 1 to 10.

The compound of formula (Ia-1) is especially a compound of formula

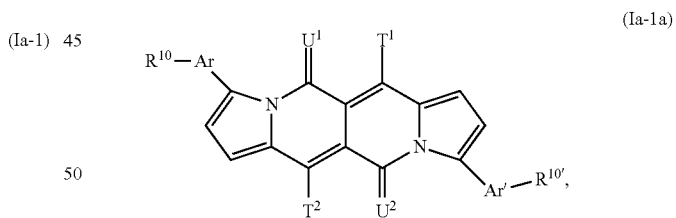

(Ia-1a)

The compound of formula (Ia-2) is especially a compound of formula

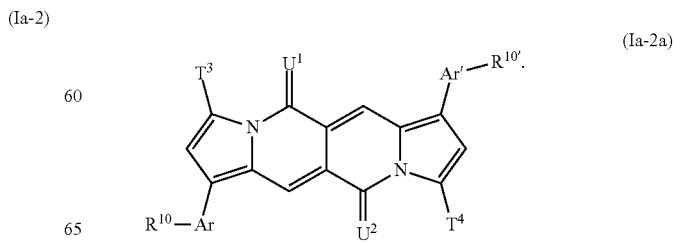

(Ia-2a)

$T^1$, $T^2$, $T^3$, $T^4$, $U^1$, $U^2$, Ar, Ar', $R^{10}$ and $R^{10'}$ are defined above.
$U^1$ and $U^2$ are preferably O.
Examples of the group of formula
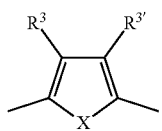
are groups of formula
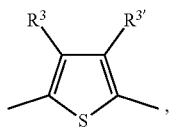
(XIa-1)
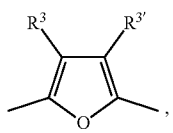
(XIa-2)
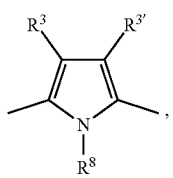
(XIa-3)
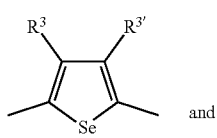 and
(XIa-4)
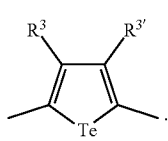
(XIa-5)
Examples of the group of formula
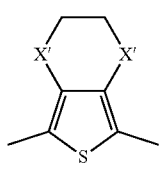
(XIb)
are groups of formula
 and
(XIb-1)
(XIb-2)
Examples of the group of formula
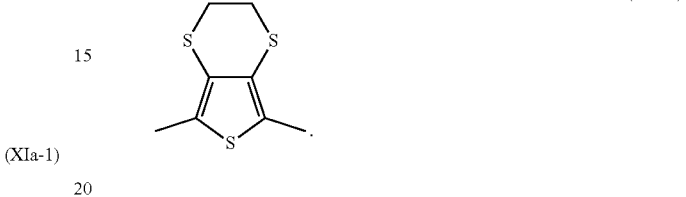
(XIIh)
are groups of formula
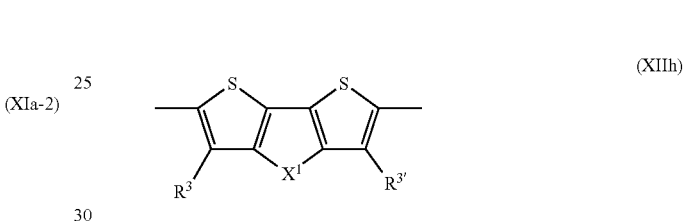
(XIIh-1)
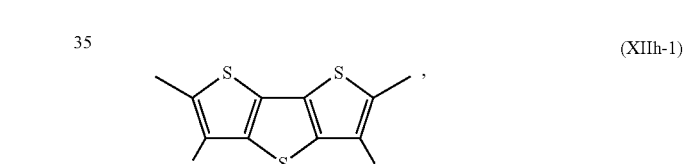
(XIIh-2)
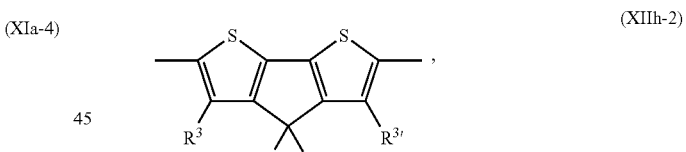
(XIIh-3)
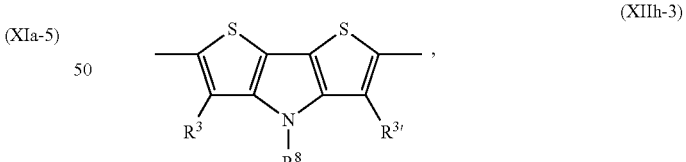
(XIIh-4)
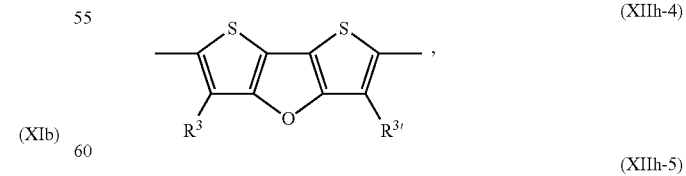
(XIIh-5)
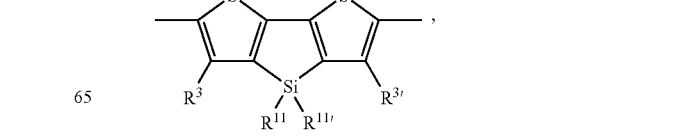

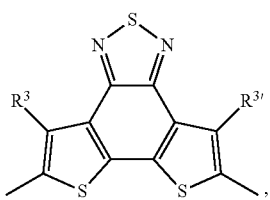
(XIIh-6)
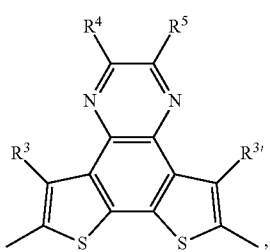
(XIIh-7)
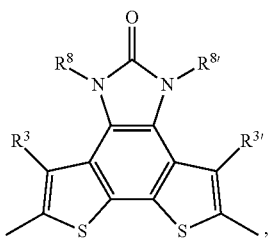
(XIIh-8)
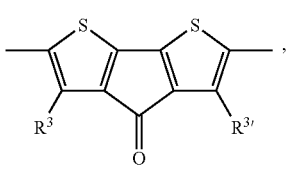
(XIIh-9)
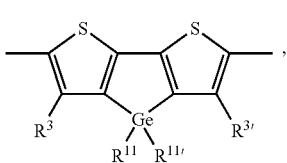
(XIIh-10)
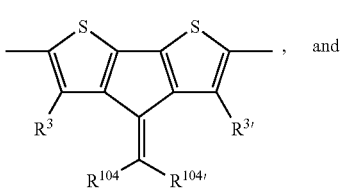
, and (XIIh-11)
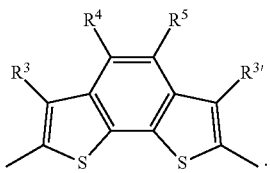
(XIIh-12)
An example of the group of formula
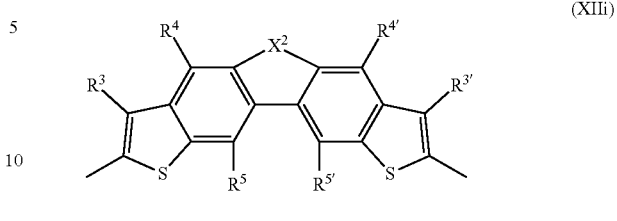
(XIIi)
is a group of formula
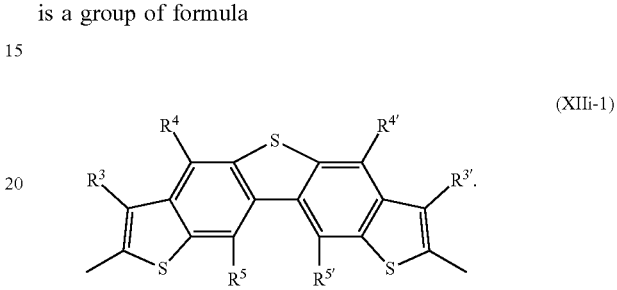
(XIIi-1)
Examples of the group of formula
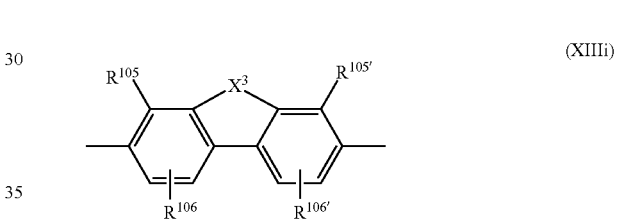
(XIIIi)
are groups of formula
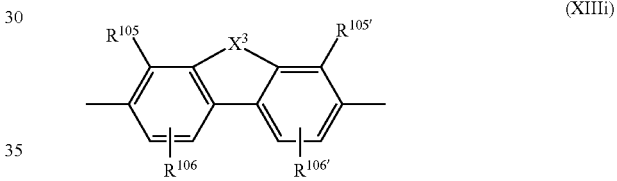
(XVIa)
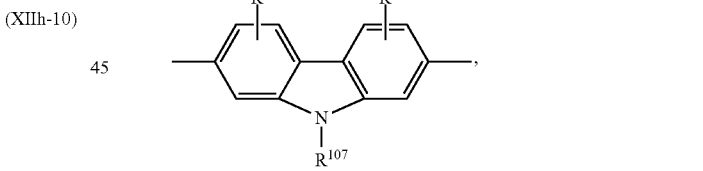
, (XVIb)
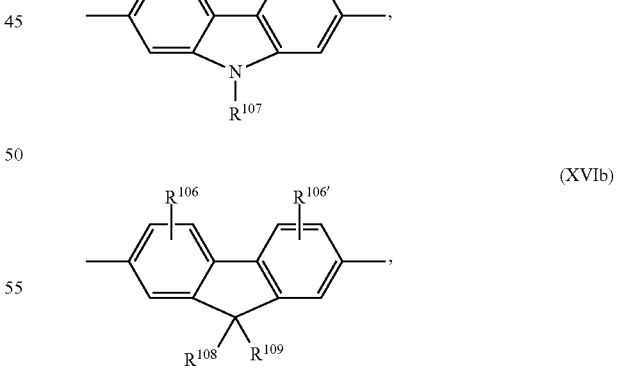
and (XVIc)
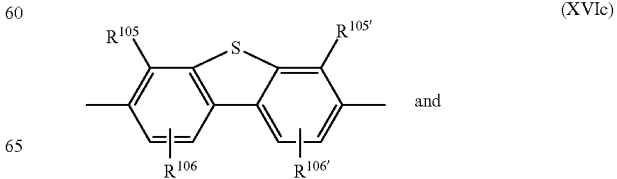

-continued

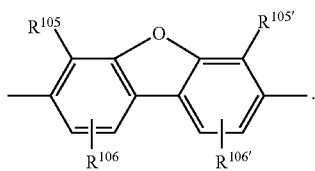
(XVId)

Examples of the group of formula

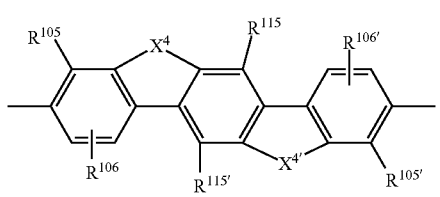
(XIIIj)

are groups of formula

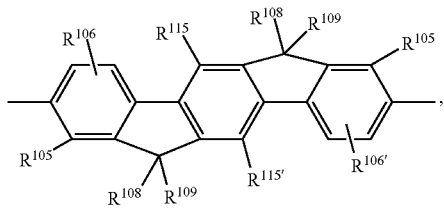
(XIIIj-1)

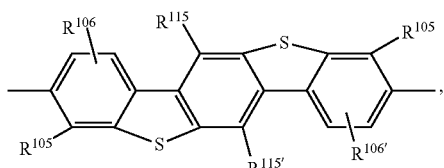
(XIIIj-2)

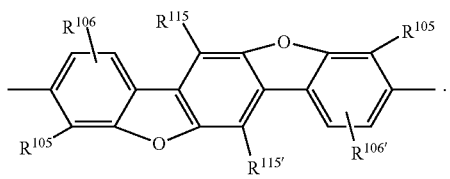
(XIIIj-3)

$Ar^1$, $Ar^{1'}$, $Ar^2$, $Ar^{2'}$, $Ar^3$ and $Ar^{3'}$ are preferabl

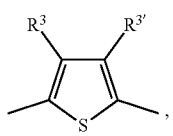
(XIa-1)

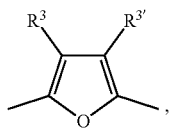
(XIa-2)

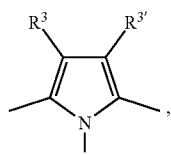
(XIa-3)

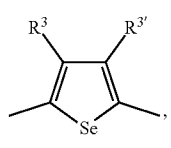
(XIa-4)

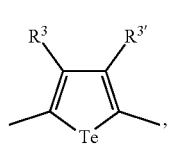
(XIa-5)

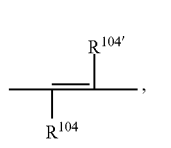
(XId)

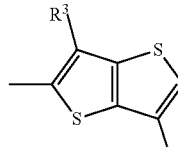
(XIf)

(XIv)

wherein $R^3$ and $R^{3'}$ are independently of each other hydrogen, F, $C_1$-$C_{25}$alkyl, or $C_1$-$C_{25}$alkoxy, $R^8$ is hydrogen, or $C_1$-$C_{25}$alkyl, and $R^{104}$ and $R^{104'}$ are independently of each other hydrogen, cyano, $COOR^{103}$, or a $C_1$-$C_{25}$alkyl group, wherein $R^{103}$ is a $C_1$-$C_{25}$alkyl group, which can optionally be interrupted by —O—, or —S—. Groups of formula (XIa-1), (XIa-2), (XIa-4), (XId), (XIf) and (XIv) are even more preferred.

—Ar—$R^{10}$ and —Ar'—$R^{10'}$ are preferably H, F, cyano, $C_1$-$C_{25}$alkyl, $C_1$-$C_{25}$alkyl substituted with one or more halogen atoms,

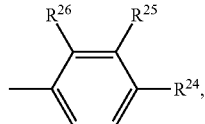 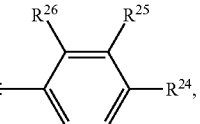

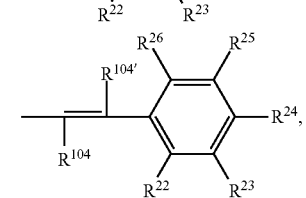 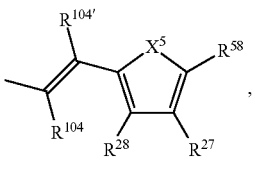

-continued

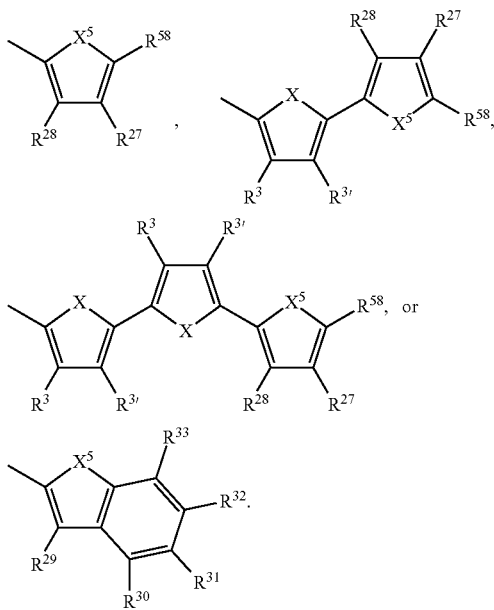

—Ar—R[10] and —Ar'—R[10'] are more preferably H, or

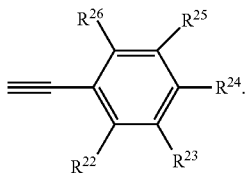

R[3] and R[3'] are independently of each other hydrogen, F, $C_1$-$C_{25}$alkyl, or $C_1$-$C_{25}$alkoxy, R[22], R[23], R[25], R[26], R[27], R[28] and R[29] to R[33] represent independently of each other H, F, cyano, $C_1$-$C_{25}$alkoxy, $C_1$-$C_{25}$alkyl substituted with one or more F, $C_1$-$C_{25}$alkyl interrupted with one or more —O—, or $C_1$-$C_{25}$alkyl, and R[24] is H, F, cyano, $NO_2$, $NR^{112}R^{113}$, phenyl, $C_1$-$C_{25}$alkoxy, $C_1$-$C_{25}$alkylthio, $C_1$-$C_{25}$alkyl substituted with one or more halogen atoms ($CF_3$), $C_1$-$C_{25}$alkyl interrupted with one or more —O—, or $C_1$-$C_{25}$alkyl;

X is O, S, Se, or NR[8], X[5] is O, S, Se, or NR[59],

R[58] is H, F, cyano, phenyl, $C_1$-$C_{25}$alkoxy, $C_1$-$C_{25}$alkylthio, $C_1$-$C_{25}$alkyl substituted with one or more halogen atoms ($CF_3$), or $C_1$-$C_{25}$alkyl;

R[8] and R[59] are hydrogen, $C_6$-$C_{18}$aryl; $C_6$-$C_{18}$aryl which is substituted one to three times by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more F; or $C_7$-$C_{25}$arylalkyl, R[112] and R[113] are independently of each other hydrogen, $C_6$-$C_{18}$aryl; $C_6$-$C_{18}$aryl which is substituted one to three times by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more F; or $C_7$-$C_{25}$arylalkyl.

In a particularly preferred embodiment the present invention is directed to compounds of formula

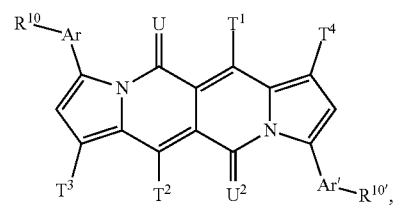

(Ia-1)

wherein $U^1$ and $U^2$ are O, $T^1$ and $T^2$ are H, a $C_1$-$C_{38}$alkyl group which can optionally be interrupted by —O—, —S—, or —NR[60]—, wherein R[60] is $C_1$-$C_{25}$alkyl, or phenyl$C_1$-$C_4$alkyl, which can be substituted one to three times with $C_1$-$C_8$alkyl and/or $C_1$-$C_8$alkoxy, $T^3$ and $T^4$ are H, a $C_1$-$C_{38}$alkyl group which can optionally be interrupted by —O—, —S—, or —NR[60]—, wherein R[60] is $C_1$-$C_{25}$alkyl, or phenyl$C_1$-$C_4$alkyl, which can be substituted one to three times with $C_1$-$C_8$alkyl and/or $C_1$-$C_8$alkoxy, and —Ar—R[10] and —Ar'—R[10'] are independently of each other H, F, cyano, $C_1$-$C_{25}$alkyl substituted with one or more fluorine atoms, $C_1$-$C_{25}$alkyl,

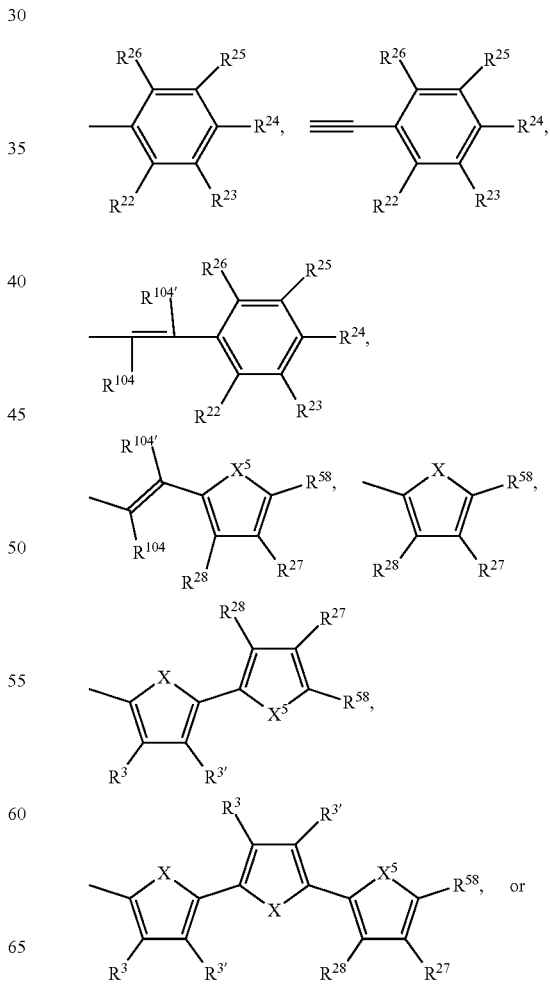

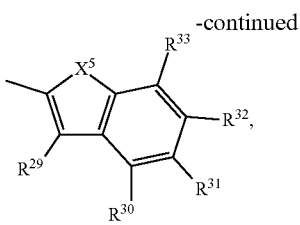

wherein $R^3$ and $R^{3'}$ are independently of each other hydrogen, F, $C_1$-$C_{25}$alkyl, or $C_1$-$C_{25}$alkoxy, $R^{22}$, $R^{23}$, $R^{25}$, $R^{26}$, $R^{27}$, $R^{28}$ and $R^{29}$ to $R^{33}$ represent independently of each other H, F, cyano, $C_1$-$C_{25}$alkoxy, $C_1$-$C_{25}$alkyl substituted with one or more F, $C_1$-$C_{25}$alkyl interrupted with one or more —O—, or $C_1$-$C_{25}$alkyl, and $R^{24}$ is H, F, cyano, $NO_2$, $NR^{112}R^{113}$, $CF_3$, phenyl, $C_1$-$C_{25}$alkoxy, $C_1$-$C_{25}$alkyl substituted with one or more halogen atoms, $C_1$-$C_{25}$alkyl interrupted with one or more —O—, or $C_1$-$C_{25}$alkyl;

X is O, S, Se, or $NR^8$, $X^5$ is O, S, Se, or $NR^{59}$, $R^{58}$ is H, F, cyano, phenyl, $C_1$-$C_{25}$alkoxy, $C_1$-$C_{25}$alkylthio, $C_1$-$C_{25}$alkyl substituted with one or more halogen atoms ($CF_3$), or $C_1$-$C_{25}$alkyl;

$R^8$ and $R^{59}$ are hydrogen, $C_6$-$C_{18}$aryl; $C_6$-$C_{18}$aryl which is substituted one to three times by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more F; or $C_7$-$C_{25}$arylalkyl, and $R^{112}$ and $R^{113}$ are independently of each other hydrogen, $C_6$-$C_8$aryl; $C_6$-$C_{18}$aryl which is substituted one to three times by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more F; or $C_7$-$C_{25}$arylalkyl.

In said embodiment $T^3$ and $T^4$ are preferably H and the present invention is preferably directed to compounds of formula (Ia-1a). $T^1$ and $T^2$ are preferably H, a $C_1$-$C_{38}$alkyl group, or phenyl$C_1$-$C_4$alkyl, which can be substituted one to three times with $C_1$-$C_8$alkyl and/or $C_1$-$C_8$alkoxy.

In another particularly preferred embodiment the present invention is directed to compounds of formula

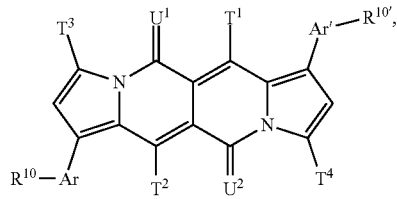

(Ia-2)

wherein
$U^1$ and $U^2$ are O,
$T^1$ and $T^2$ are H, a $C_1$-$C_{38}$alkyl group which can optionally be interrupted by —O—, —S—, or —$NR^{60}$—, wherein $R^{60}$ is $C_1$-$C_{25}$alkyl, or phenyl$C_1$-$C_4$alkyl, which can be substituted one to three times with $C_1$-$C_8$alkyl and/or $C_1$-$C_8$alkoxy, $T^3$ and $T^4$ are H, a $C_1$-$C_{38}$alkyl group can optionally be interrupted by —O—, —S—, or —$NR^{60}$—, wherein $R^{60}$ is $C_1$-$C_{25}$alkyl, or phenyl$C_1$-$C_4$alkyl, which can be substituted one to three times with $C_1$-$C_8$alkyl and/or $C_1$-$C_8$alkoxy, and —Ar—$R^{10}$ and —Ar'—$R^{10'}$ are independently of each other H, F, cyano, $C_1$-$C_{25}$alkyl substituted with one or more fluorine atoms, $C_1$-$C_{25}$alkyl,

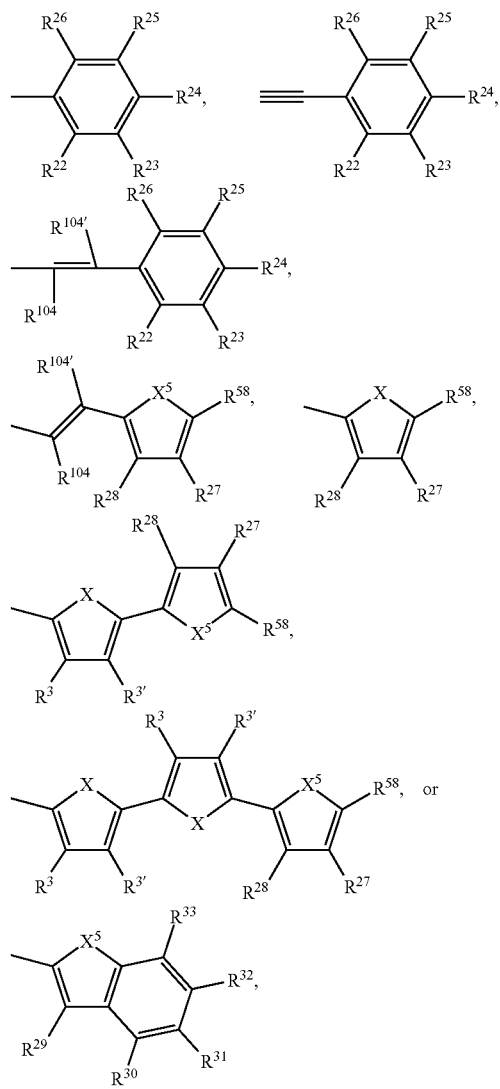

wherein $R^3$ and $R^{3'}$ are independently of each other hydrogen, F, $C_1$-$C_{25}$alkyl, or $C_1$-$C_{25}$alkoxy, $R^{22}$, $R^{23}$, $R^{25}$, $R^{26}$, $R^{27}$, $R^{28}$ and $R^{29}$ to $R^{33}$ represent independently of each other H, F, cyano, $C_1$-$C_{25}$alkoxy, $C_1$-$C_{25}$alkyl substituted with one or more F, $C_1$-$C_{25}$alkyl interrupted with one or more —O—, or $C_1$-$C_{25}$alkyl, and $R^{24}$ is H, F, cyano, $NO_2$, $NR^{112}R^{113}$, $CF_3$, phenyl, $C_1$-$C_{25}$alkoxy, $C_1$-$C_{25}$alkyl substituted with one or more halogen atoms, $C_1$-$C_{25}$alkyl interrupted with one or more —O—, or $C_1$-$C_{25}$alkyl;

X is O, S, Se, or $NR^8$, $X^5$ is O, S, Se, or $NR^{59}$, $R^{58}$ is H, F, cyano, phenyl, $C_1$-$C_{25}$alkoxy, $C_1$-$C_{25}$alkylthio, $C_1$-$C_{25}$alkyl substituted with one or more halogen atoms ($CF_3$), or $C_1$-$C_{25}$alkyl;

$R^8$ and $R^{59}$ are hydrogen, $C_6$-$C_{18}$aryl; $C_6$-$C_{18}$aryl which is substituted one to three times by $C_1$-$C_{18}$alkyl, or $C_1$-$C_1$alkoxy; $C_1$-$C_{25}$alkyl, which may optionally be interrupted by one or more oxygen or sulphur atoms and/or is optionally substituted by one or more F; or $C_7$-$C_{25}$arylalkyl, and $R^{112}$ and $R^{113}$ are independently of each other hydrogen, $C_6$-$C_{18}$aryl; $C_6$-$C_{18}$aryl which is substituted one to three times by $C_1$-$C_{18}$alkyl, or $C_1$-$C_{18}$alkoxy; $C_1$-$C_{25}$alkyl, which may optionally be interrupted by one or more oxygen or sulphur atoms and/or is optionally substituted by one or more F; or $C_7$-$C_{25}$arylalkyl.

In said embodiment $T^1$ and $T^2$ are preferably H and the present invention is preferably directed to compounds of formula (Ia-2a). $T^3$ and $T^4$ are preferably H, a $C_1$-$C_{38}$alkyl group, or phenyl$C_1$-$C_4$alkyl, which can be substituted one to three times with $C_1$-$C_8$alkyl and/or $C_1$-$C_8$alkoxy.

Examples of compounds of formula (I) are compounds (A-1) to (A-15) shown in claim 9 and compounds of formula (A-16)
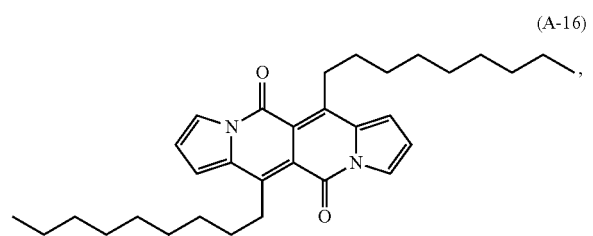

(A-17)
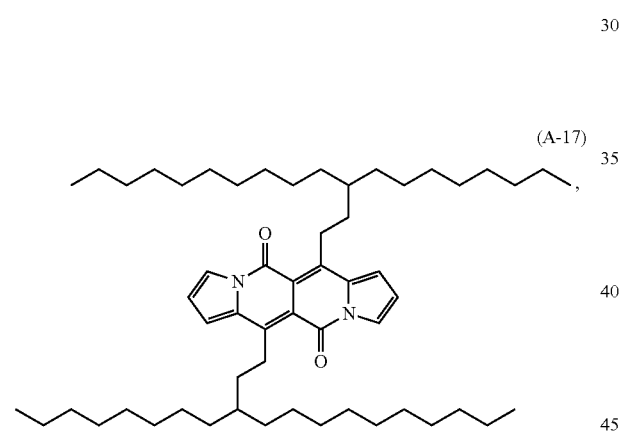

(A-18)
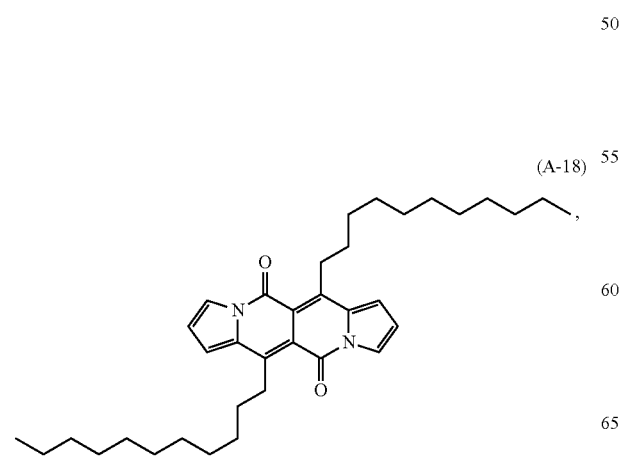

-continued (A-19)
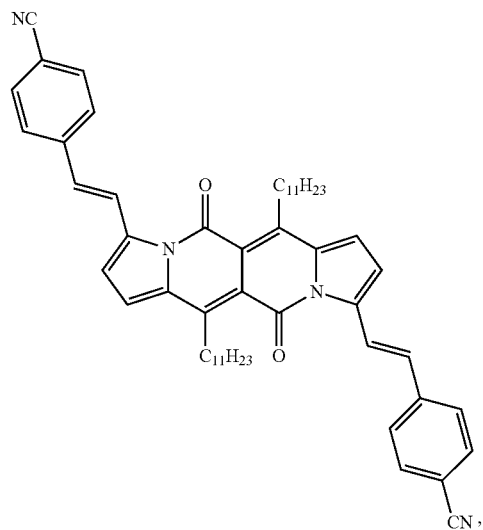

(A-20)
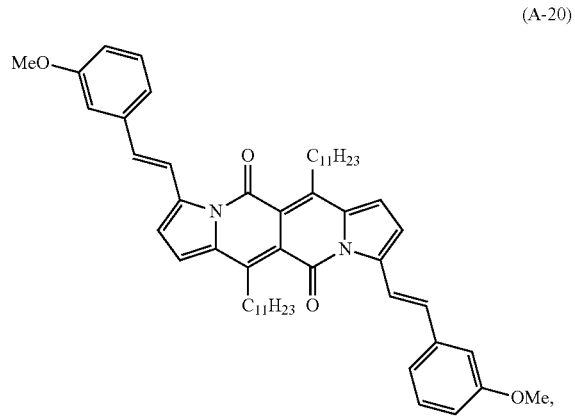

(A-21)
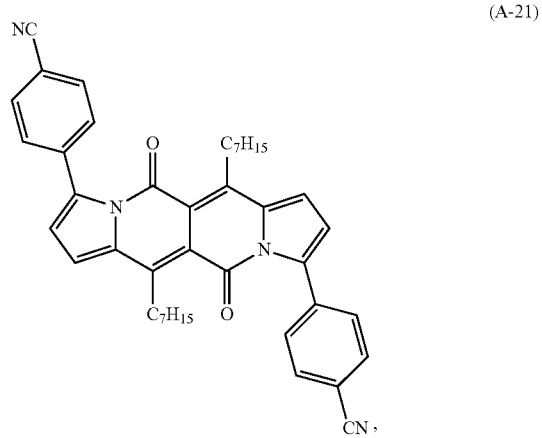

-continued (A-22)
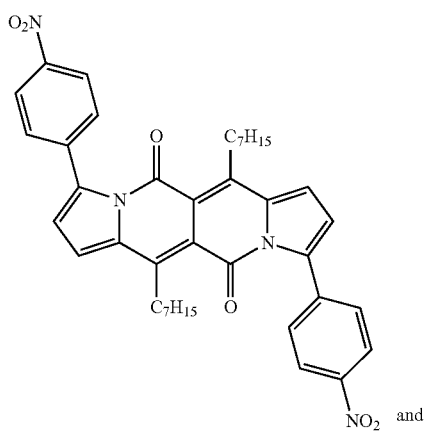
and (A-23)
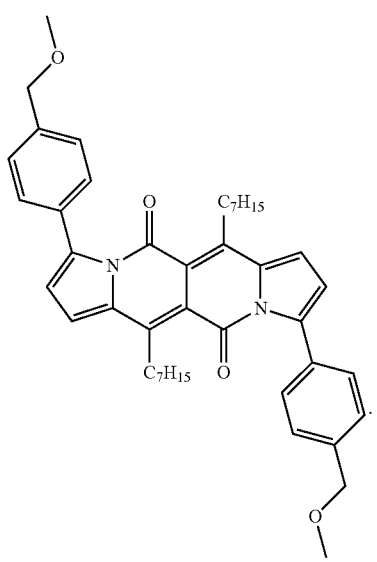

A process for producing compounds of formula (Ia)
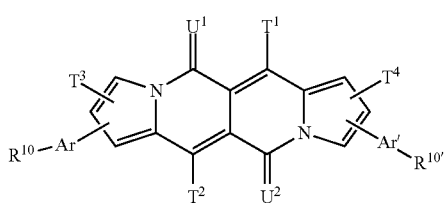

(a) reacting a compound of formula (XI)
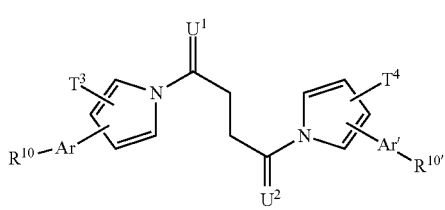

with a compound of formula T¹COOH (XIIa) and T²COOH (XIIb), or T¹COOH (XIIa) in a solvent, such as, for example, dichloromethane, in the presence of an acid and/or an acid anhydride, such as, for example, trifluoroacetic acid and/or trifluoroacetic anhydride, wherein $T^1$, $T^2$, $T^3$, $T^4$, $U^1$, $U^2$, Ar, Ar', $R^{10}$ and $R^{10'}$ are defined above and in case a compound of formula (XI) is reacted only with a compound of formula (XIIa) $T^2$ in formula (Ia) has the meaning of $T^1$. Instead of the acids T¹COOH (XIIa) and T²COOH (XIIb) their anhydrides, $(T^1CO)_2O$ and $(T^2CO)_2O$, may be used.

The compounds of formula (XI), (XIIa) and (XIIb) are commercially available, or can be prepared according to procedures known in the art.

Another process for producing compounds of formula (Ia)
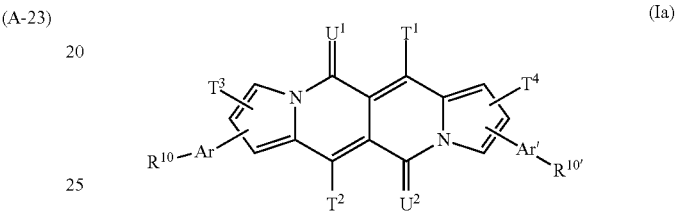

comprises (a) reacting a compound of formula (XIIIa)
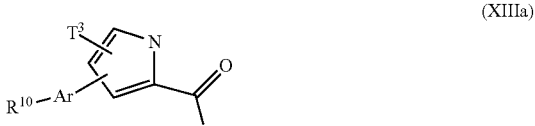
and (XIIIb)
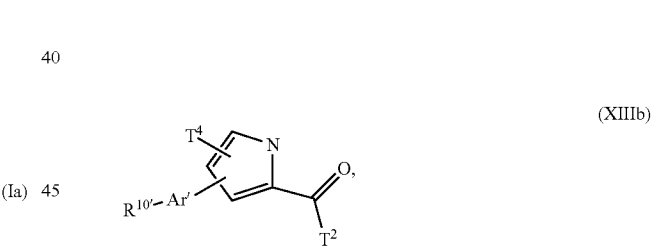

or (XIIIa) with a compound of formula ClCO(CH₂)₂COCl (XIV) in a solvent, such as, for example, dimethylformamide (DMF), or dichloromethane, in the presence of a base, such as, for example, 4-dimethylaminopyridine, trimethylamine, or potassium carbonate, wherein $T^1$, $T^2$, $T^3$, $T^4$, $U^1$, $U^2$, Ar, Ar', $R^{10}$ and $R^{10'}$ are defined above and in case a compound of formula (XIV) is reacted only with a compound of formula (XIIIa) $T^2$ in formula (Ia) has the meaning of $T^1$. The process can be used for the production of compounds of formula (Ia), wherein $T^1$ and $T^2$ are H, such as, for example, compound (A-1).

The compounds of formula (XIIIa), (XIIIa) and (XIV) are commercially available, or can be prepared according to procedures known in the art.

Compound (C-1) can, for example, be prepared starting from the compound (A-3) as shown in the reaction scheme below:

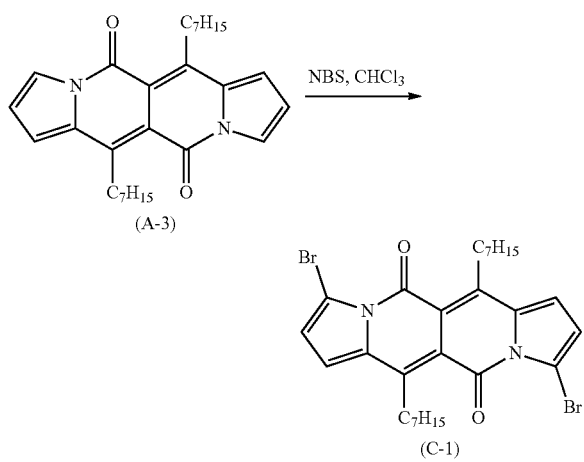

The bromination is carried out in a suitable solvent, like chloroform, using two equivalents of N-bromo-succinimide at a temperature between −30° C. and +50° C., preferably between −10° C. and room temperature, e.g. at 0° C.

Advantageously, the compound of formula I, or an organic semiconductor material, layer or component, comprising the compound of formula I can be used in organic photovoltaics (solar cells) and photodiodes, or in an organic field effect transistor (OFET).

A mixture containing the compound of formula I results in a semi-conducting layer comprising the compound of formula I (typically 0.1% to 99.9999% by weight, more specifically 1% to 99.9999% by weight, even more specifically 5% to 99.9999% by weight, especially 20 to 85% by weight) and at least another material. The other material can be, but is not restricted to another compound of formula I, a polymer of the present invention, a semi-conducting polymer, a non-conductive polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a compound of formula I and to a semiconductor device, comprising a compound of formula I and/or an organic semiconductor material, layer or component.

The semiconductor is preferably used in an organic photovoltaic (PV) device (solar cell), a photodiode, or an organic field effect transistor. The structure and the components of the OFET device has been described in more detail below.

Accordingly, the invention provides organic photovoltaic (PV) devices (solar cells) comprising a compound of the formula I.

The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula I. Preferably, the photoactive layer is made of a compound of the formula I, as an electron donor and an acceptor material, like a fullerene, particularly a functionalized fullerene PCBM, as an electron acceptor. As stated above, the photoactive layer may also contain a polymeric binder. The ratio of the small molecules of formula I to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compounds of formula III, or any semi-conducting polymer, such as, for example, a polymer of formula I, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula I, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride, (c) a photoactive layer,
(d) optionally a smoothing layer,
(e) a middle electrode (such as Au, Al, ZnO, TiO$_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

An OFET device according to the present invention preferably comprises:
a source electrode,
a drain electrode,
a gate electrode,
a semiconducting layer,
one or more gate insulator layers, and
optionally a substrate, wherein the semiconductor layer comprises a compound of formula I.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula I located on the second side of the insulator, and a drain electrode and a source electrode located on the polymer layer.

The present invention is also directed to polymers, comprising a repeating unit of the formula

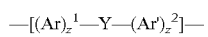

—[(Ar)$_z^1$—Y—(Ar')$_z^2$]— (V), wherein $z^1$ and $z^2$ are independently of each other 0, or 1,
Y, Ar and Ar' are defined above, or below.

The repeating unit of the formula (V) is preferably a repeating unit of formula

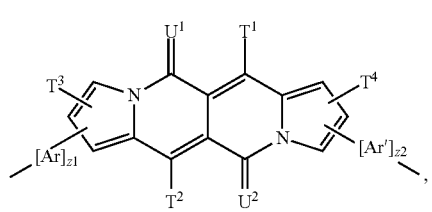

(Va)

$z^1$ and $z^2$ are independently of each other 0, or 1 and $T^1$, $T^2$, $T^3$, $T^4$, $U^1$, $U^2$, Ar and Ar' are defined above, or below.

In a more preferred embodiment the repeating unit of the formula (V) is a repeating unit of formula

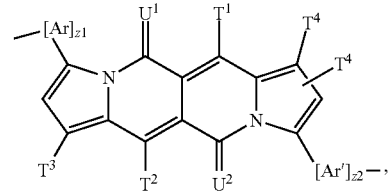

(Va-1)

especially a repeating unit of formula

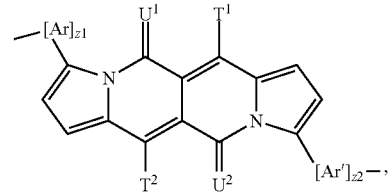

(Va-1a)

wherein z1, z2, $T^1$, $T^2$, $T^3$, $T^4$, $U^1$, $U^2$, Ar and Ar' are defined above and below.

In another more preferred embodiment the repeating unit of the formula (V) is a repeating unit of formula

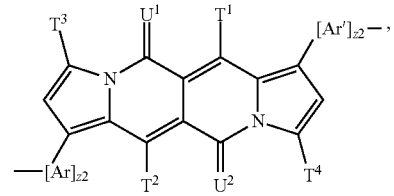

(Va-2)

especially a repeating unit of formula

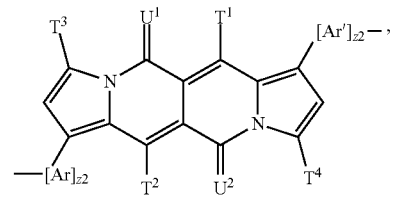

(Va-2a)

wherein z1, z2, $T^1$, $T^2$, $T^3$, $T^4$, $U^1$, $U^2$, Ar and Ar' are defined above and below.

$U^1$ and $U^2$ are preferably O.

Preferably $T^1$, $T^2$, $T^3$ and $T^4$ are independently of each other H, a $C_1$-$C_{38}$alkyl group which can optionally be substituted one or more times with $C_1$-$C_{12}$alkoxy, halogen, $C_5$-$C_{12}$cycloalkyl, or $E_{Si}$; and/or can optionally be interrupted by —O—, or —S—; or a $C_2$-$C_{38}$alkenyl group which can optionally be substituted one or more times with $C_1$-$C_{12}$alkoxy, halogen, $C_5$-$C_{12}$cycloalkyl, or $E_{Si}$; and/or can optionally be interrupted by —O—, or —S—; wherein $E_{Si}$ is —SiR$^{161}$R$^{162}$R$^{163}$. More preferred, $T^1$, $T^2$, $T^3$ and $T^4$ are independently of each other H, a $C_1$-$C_{38}$alkyl group which can optionally be substituted one or more times with $C_1$-$C_{12}$alkoxy, halogen, $C_5$-$C_{12}$cycloalkyl, or $E_{Si}$; and/or can optionally be interrupted by —O—, or —S—, wherein $E_{Si}$ is —SiR$^{161}$R$^{162}$R$^{163}$. Even more preferred, T$^1$, T$^2$, T$^3$ and T$^4$ are independently of each other H, or a C$_1$-C$_{38}$alkyl group, which can optionally be interrupted by —O—, or —S—. Most preferred T$^1$, T$^2$, T$^3$ and T$^4$ are H, or a C$_1$-C$_{38}$alkyl group.

R$^{161}$, R$^{162}$ and R$^{163}$ are independently of each other C$_1$-C$_8$alkyl, C$_5$-C$_6$cycloalkyl, which might optionally be substituted with C$_1$-C$_4$alkyl; C$_1$-C$_8$haloalkyl, C$_2$-C$_8$alkenyl, —O—SiR$^{164}$R$^{165}$R$^{166}$, —(O—SiR$^{164}$R$^{165}$)$_d$—R$^{166}$, or phenyl;

R$^{164}$, R$^{165}$ and R$^{166}$ are independently of each other C$_1$-C$_8$alkyl, C$_1$-C$_8$haloalkyl, C$_2$-C$_8$alkenyl, —O—SiR$^{169}$R$^{170}$R$^{171}$, —(O—SiR$^{169}$R$^{170}$)$_d$—R$^{171}$, or phenyl;

R$^{169}$, R$^{170}$ and R$^{171}$ are independently of each other C$_1$-C$_8$alkyl, C$_1$-C$_8$haloalkyl, C$_2$-C$_8$alkenyl, —O—Si(CH$_3$)$_3$, or phenyl;

d is an integer from 1 to 10.

Preferably, R$^{161}$, R$^{162}$ and R$^{163}$ are independently of each other C$_1$-C$_8$alkyl, —O—SiR$^{164}$R$^{165}$R$^{166}$, or —(O—SiR$^{164}$R$^{165}$)$_d$—R$^{166}$. Preferably, R$^{164}$, R$^{165}$ and R$^{166}$ are independently of each other C$_1$-C$_8$alkyl, —O—SiR$^{169}$R$^{170}$R$^{171}$, or —(O—SiR$^{169}$R$^{170}$)$_d$—R$^{171}$. Preferably, R$^{169}$, R$^{170}$ and R$^{171}$ are independently of each other C$_1$-C$_8$alkyl or —O—Si(CH$_3$)$_3$. d is preferably an integer from 1 to 5.

—Ar— and —Ar'— are preferably a single bond,

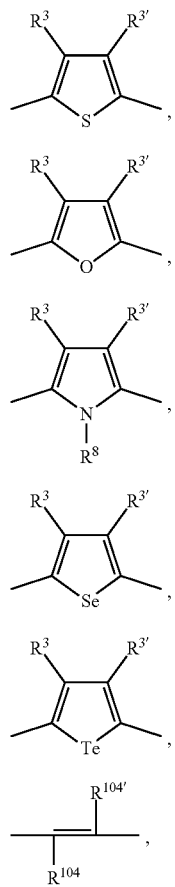

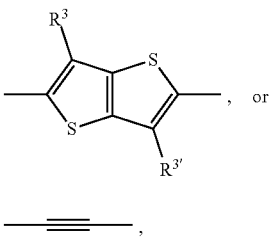

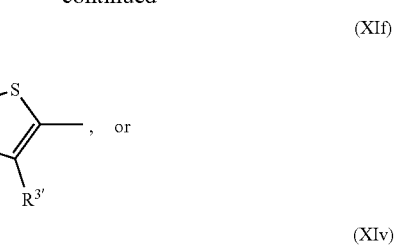

wherein

R$^3$ and R$^{3'}$ are independently of each other hydrogen, F, C$_1$-C$_{25}$alkyl, or C$_1$-C$_{25}$alkoxy, R$^8$ is hydrogen, or C$_1$-C$_{25}$alkyl, and R$^{104}$ and R$^{104'}$ are independently of each other hydrogen, cyano, COOR$^{103}$, or a C$_1$-C$_{25}$alkyl group, wherein R$^{103}$ is a C$_1$-C$_{25}$alkyl group, which can optionally be interrupted by —O—, or —S—. R$^3$ and R$^{3'}$ are preferably hydrogen. Preferably, R$^{104}$ and R$^{104'}$ are independently of each other hydrogen, or cyano, most preferred hydrogen.

Groups of formula (XIa-1), (XIa-2), (XIa-4), (XId), (XIf) and (XIv) are even more preferred.

In another embodiment the present invention is directed to polymers, comprising a repeating unit of the formula *—[—A—]—* and a repeating unit *—[—COM$^1$—]—*, wherein A is a repeating unit of formula (V), and —COM$^1$- is a repeating unit, which has the meaning of Ar$^2$, wherein Ar$^2$ is defined in claim 1, or a group of formula

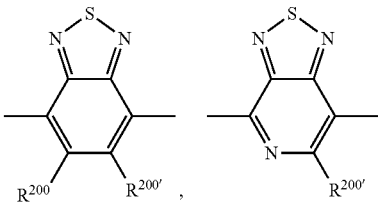

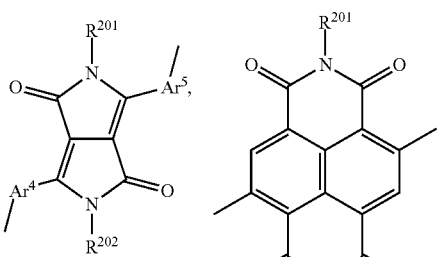

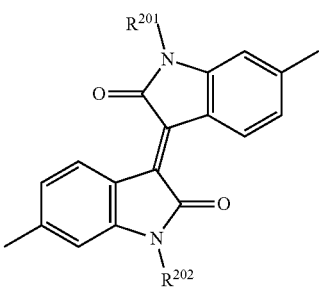

-continued

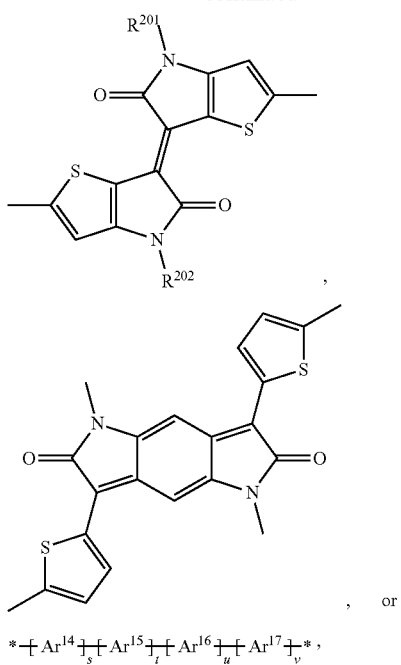

, or

*―⟨Ar¹⁴⟩ₛ―⟨Ar¹⁵⟩ₜ―⟨Ar¹⁶⟩ᵤ―⟨Ar¹⁷⟩ᵥ―*, s is 1, t is 1, u is 0, or 1, v is 0, or 1, and Ar⁴ and Ar⁵ are independently of each other a group of formula

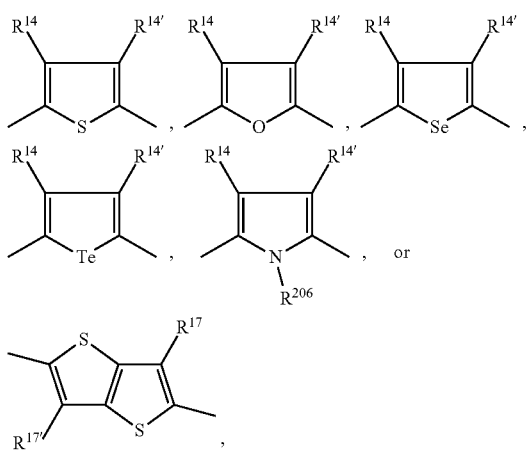

Ar¹⁴, Ar¹⁵, Ar¹⁶ and Ar¹⁷ are independently of each other a group of formula

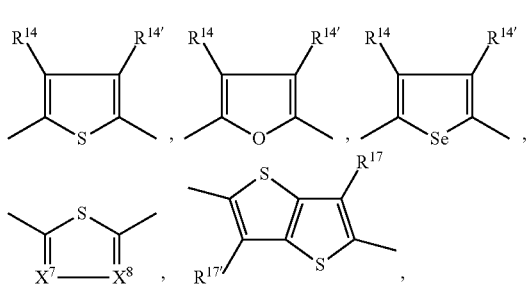

-continued

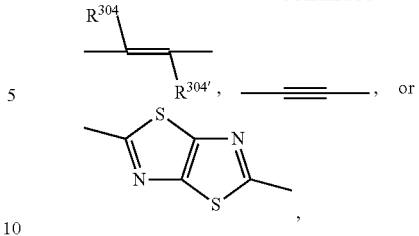

wherein one of $X^7$ and $X^8$ is N and the other is $CR^{14}$, $R^{14}$, $R^{14'}$, $R^{17}$ and $R^{17'}$ are independently of each other H, F, a $C_1$-$C_{25}$alkyl group, or a $C_1$-$C_{25}$alkoxy group, $R^{200}$ and $R^{200'}$ are independently of each other H, or F, $R^{201}$ and $R^{202}$ are independently of each other H, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —NR⁶⁰—, CONR⁶⁰—, NR⁶⁰CO—, —COO—, —CO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —NR⁶⁰—, CONR⁶⁰—, NR⁶⁰CO—, —COO—, —CO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —NR⁶⁰—, CONR⁶⁰—, NR⁶⁰CO—, —COO—, —CO— or —OCO—, a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —NR⁶⁰—, CONR⁶⁰—, NR⁶⁰CO—, —COO—, —CO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$;

a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and $E_{Si}$ is defined in claim 1, $R^{60}$ is hydrogen, $C_1$-$C_{18}$haloalkyl, $C_1$-$C_{25}$alkyl, which may optionally be interrupted by one or more oxygen or sulphur atoms; $C_1$-$C_{18}$alkanoyl, or $C_7$-$C_{25}$arylalkyl, $R^{206}$ is hydrogen, or $C_1$-$C_{25}$alkyl, or $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; and $R^{304}$ and $R^{304'}$ are independently of each other hydrogen, cyano, COOR³⁰⁵, or a $C_1$-$C_{25}$alkyl group, wherein $R^{305}$ is a $C_1$-$C_{25}$alkyl group, which can optionally be interrupted by —O—, or S—.

Ar$^4$ and Ar$^5$ are preferably a group of formula

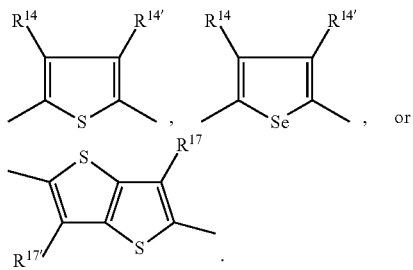

R$^{14}$, R$^{14'}$, R$^{17}$ and R$^{17'}$ are preferably H.

Preferably, Ar$^{14}$, Ar$^{15}$, Ar$^{16}$ and Ar$^{17}$ are independently of each other a group of formula

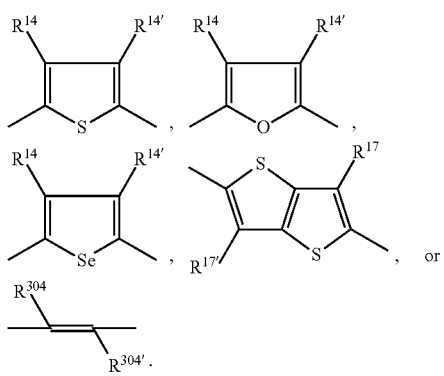

$E_{Si}$ is preferably —SiR$^{161}$R$^{162}$R$^{163}$;

R$^{161}$, R$^{162}$ and R$^{163}$ are independently of each other C$_1$-C$_8$alkyl, C$_5$-C$_6$cycloalkyl, which might optionally be substituted with C$_1$-C$_4$alkyl; C$_1$-C$_8$haloalkyl, C$_2$-C$_8$alkenyl, —O—SiR$^{164}$R$^{165}$R$^{166}$, —(O—SiR$^{164}$R$^{165}$)$_d$—R$^{166}$, or phenyl;

R$^{164}$, R$^{165}$ and R$^{166}$ are independently of each other C$_1$-C$_8$alkyl, C$_1$-C$_8$haloalkyl, C$_2$-C$_8$alkenyl, —O—SiR$^{169}$R$^{170}$R$^{171}$, —(O—SiR$^{169}$R$^{170}$)$_d$—R$^{171}$, or phenyl;

R$^{169}$, R$^{170}$ and R$^{171}$ are independently of each other C$_1$-C$_8$alkyl, C$_1$-C$_8$haloalkyl, C$_2$-C$_8$alkenyl, —O—Si(CH$_3$)$_3$, or phenyl;

d is an integer from 1 to 10.

Preferably, R$^{161}$, R$^{162}$ and R$^{163}$ are independently of each other C$_1$-C$_8$alkyl, —O—SiR$^{164}$R$^{165}$R$^{166}$, or —(O—SiR$^{164}$R$^{165}$)$_d$—R$^{166}$. Preferably, R$^{164}$, R$^{165}$ and R$^{166}$ are independently of each other C$_1$-C$_8$alkyl, —O—SiR$^{169}$R$^{170}$R$^{171}$, or —(O—SiR$^{169}$R$^{170}$)$_d$—R$^{171}$. Preferably, R$^{169}$, R$^{170}$ and R$^{171}$ are independently of each other C$_1$-C$_8$alkyl or —O—Si(CH$_3$)$_3$. d is preferably an integer from 1 to 5. Preferably, R$^{201}$ and R$^{202}$ are independently of each other H, a C$_1$-C$_{50}$alkyl group which can optionally be substituted one or more times with halogen, or $E_{Si}$; and/or can optionally be interrupted by —O—, or —S—; or a C$_2$-C$_{50}$alkenyl group which can optionally be substituted one or more times with halogen, or $E_{Si}$; and/or can optionally be interrupted by —O—, or —S—. More preferred, R$^{201}$ and R$^{202}$ are independently of each other a C$_1$-C$_{50}$alkyl group, which can optionally be interrupted by —O—, or —S—. Most preferred, R$^{201}$ and R$^{202}$ are a C$_1$-C$_{50}$alkyl group. Preferably, R$^{304}$ and R$^{304'}$ are independently of each other hydrogen, or cyano. More preferred R$^{304}$ and R$^{304'}$ are hydrogen.

Examples of polymers, comprising a repeating unit of formula (V) are polymers (P-1) to (P-10) shown in claim 16 and the polymers of formula

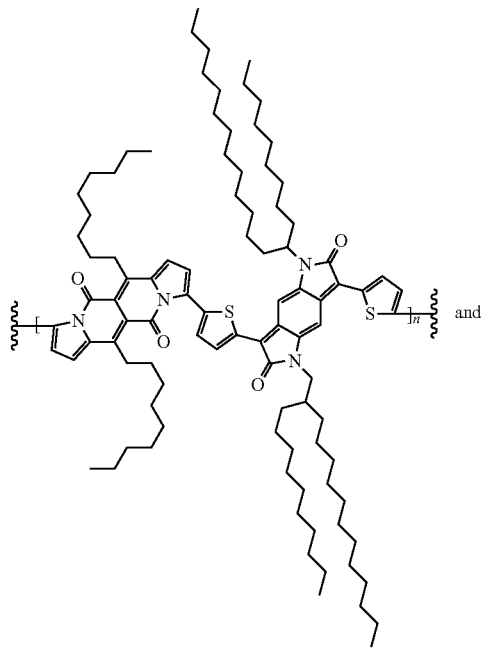

(P-11)

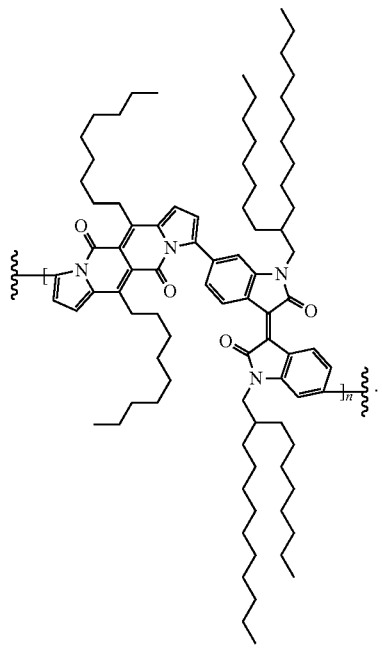

(P-12)

To prepare polymers corresponding to formula -[-[A]-[COM]-]$_n$- (VII) a dihalogenide of formula X$^6$-A-X$^6$ is reacted with an (equimolar) amount of a diboronic acid or diboronate corresponding to formula X$^{6'}$-[-COM$^1$-]-X$^{6'}$; or a dihalogenide of formula X$^6$-[-COM$^1$-]-X$^6$ is reacted with an (equimolar) amount of a diboronic acid or diboronate corresponding to formula X$^{6'}$-A-X$^{6'}$, wherein X$^6$ is halogen, especially Cl, Br, or I, very especially Br, and $X^{6'}$ is independently in each occurrence —$B(OH)_2$, —$B(OY^1)_2$,

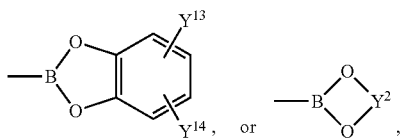

wherein $Y^1$ is independently in each occurrence a $C_1$-$C_{10}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —$C(CH_3)_2C(CH_3)_2$—, —$CH_2C(CH_3)_2CH_2$—, or —$C(CH_3)_2CH_2C(CH_3)_2$—, and $Y^{13}$ and $Y^{14}$ are independently of each other hydrogen, or a $C_1$-$C_{10}$alkyl group, under the catalytic action of Pd and triphenylphosphine. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252. Control of molecular weight is possible by using either an excess of dibromide, diboronic acid, or diboronate, or a chain terminator.

The process described in WO2010/136352 can, for example, be used for the preparation of polymers of formula (VII). The polymerisation is carried out in presence of
 a) a catalyst/ligand system comprising a palladium catalyst and an organic phosphine or phosphonium compound,
 b) a base,
 c) a solvent or a mixture of solvents.

Preferred organic phosphines are selected from trisubstituted phosphines of formula

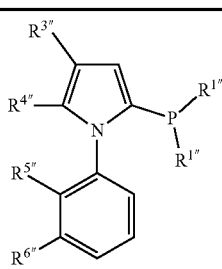

| Cpd. | $R^{1''}$ | $R^{5''}$ | $R^{6''}$ | $R^{3''}$ | $R^{4''}$ |
|---|---|---|---|---|---|
| PN-1 | H₃C-C(CH₃)₂-CH₃ (tert-butyl) | H | H | H | H |
| PN-2 | cyclohexyl | H | H | H | H |
| PN-3 | phenyl | H | H | H | H |

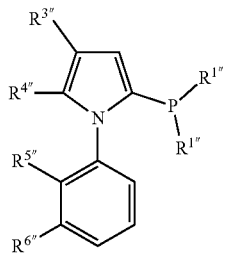

| Cpd. | $R^{1''}$ | $R^{5''}$ | $R^{6''}$ | $R^{3''}$ | $R^{4''}$ |
|---|---|---|---|---|---|
| PN-4 | adamantyl | H | H | H | H |
| PN-5 | cyclohexyl | —OCH₃ | H | H | H |
| PN-6 | cyclohexyl | 1) | 1) | H | H |
| PN-7 | tert-butyl | 1) | 1) | H | H |
| PN-8 | phenyl | 1) | 1) | H | H |
| PN-9 | adamantyl | 1) | 1) | H | H |
| PN-10 | cyclohexyl | H | H | 2) | 2) |
| PN-11 | tert-butyl | H | H | 2) | 2) |
| PN-12 | phenyl | H | H | 2) | 2) |
| PN-13 | adamantyl | H | H | 2) | 2) |

1) $R^{5''}$ and $R^{6''}$ together form a ring 

2) $R^{3''}$ and $R^{4''}$ together form a ring 

Examples of preferred catalysts include the following compounds:

palladium(II) acetylacetonate, palladium(0) dibenzylidene-acetone complexes, palladium(II) propionate, $Pd_2(dba)_3$: [tris(dibenzylideneacetone) dipalladium(0)], $Pd(dba)_2$: [bis(dibenzylideneacetone) palladium(0)], $Pd(PR_3)_2$, wherein $PR_3$ is a trisubstituted phosphine of formula VI, $Pd(OAc)_2$: [palladium(II) acetate], palladium(II) chloride, palladium(II) bromide, lithium tetrachloropalladate(II), $PdCl_2(PR_3)_2$; wherein $PR_3$ is a trisubstituted phosphine of formula VI; palladium(0) diallyl ether complexes, palladium(II) nitrate, $PdCl_2(PhCN)_2$: [dichlorobis(benzonitrile) palladium(II)], $PdCl_2(CH_3CN)$: [dichlorobis(acetonitrile) palladium(II)], and $PdCl_2(COD)$: [dichloro(1,5-cyclooctadiene) palladium (II)].

Especially preferred are $PdCl_2$, $Pd_2(dba)_3$, $Pd(dba)_2$, $Pd(OAc)_2$, or $Pd(PR_3)_2$. Most preferred are $Pd_2(dba)_3$ and $Pd(OAc)_2$.

The palladium catalyst is present in the reaction mixture in catalytic amounts. The term "catalytic amount" refers to an amount that is clearly below one equivalent of the (hetero)aromatic compound(s), preferably 0.001 to 5 mol-%, most preferably 0.001 to 1 mol-%, based on the equivalents of the (hetero)aromatic compound(s) used.

The amount of phosphines or phosphonium salts in the reaction mixture is preferably from 0.001 to 10 mol-%, most preferably 0.01 to 5 mol-%, based on the equivalents of the (hetero)aromatic compound(s) used. The preferred ratio of Pd:phosphine is 1:4.

The base can be selected from all aqueous and nonaqueous bases and can be inorganic, or organic. It is preferable that at least 1.5 equivalents of said base per functional boron group is present in the reaction mixture. Suitable bases are, for example, alkali and alkaline earth metal hydroxides, carboxylates, carbonates, fluorides and phosphates such as sodium and potassium hydroxide, acetate, carbonate, fluoride and phosphate or also metal alcoholates. It is also possible to use a mixture of bases. The base is preferably a lithium salt, such as, for example, lithium alkoxides (such as, for example, lithium methoxide and lithium ethoxide), lithium hydroxide, carboxylate, carbonate, fluoride and/or phosphate.

The at present most preferred base is aqueous LiOHx$H_2$O (monohydrate of LiOH) and (waterfree) LiOH.

The reaction is typically conducted at about 0° C. to 180° C., preferably from 20 to 160° C., more preferably from 40 to 140° C. and most preferably from 40 to 120° C. A polymerization reaction may take 0.1, especially 0.2 to 100 hours.

In a preferred embodiment of the present invention the solvent is THF, the base is LiOH*$H_2$O and the reaction is conducted at reflux temperature of THF (about 65° C.).

The solvent is for example selected from toluene, xylenes, anisole, THF, 2-methyltetrahydrofuran, dioxane, chlorobenzene, fluorobenzene or solvent mixtures comprising one or more solvents like e.g. THF/toluene and optionally water. Most preferred is THF, or THF/water.

Advantageously, the polymerisation is carried out in presence of
a) palladium(II) acetate, or $Pd_2(dba)_3$, (tris(dibenzylideneacetone)dipalladium(0)) and an organic phosphine PN-1 to PN-8,
b) LiOH, or LiOHx$H_2$O; and
c) THF, and optionally water. If the monohydrate of LiOH is used, no water needs to be added.

The palladium catalyst is present in an amount of preferably about 0.5 mol-%, based on the equivalents of the (hetero)aromatic compound(s) used. The amount of phosphines or phosphonium salts in the reaction mixture is preferably about 2 mol-%, based on the equivalents of the (hetero)aromatic compound(s) used. The preferred ratio of Pd:phosphine is about 1:4.

Preferably the polymerization reaction is conducted under inert conditions in the absence of oxygen. Nitrogen and more preferably argon are used as inert gases.

The process described in WO2010/136352 is suitable for large-scale applications, is readily accessible and convert starting materials to the respective polymers in high yield, with high purity and high selectivity. The process can provide polymers having weight average molecular weights of at least 10,000, more preferably at least 20,000, most preferably at least 30,000. The at present most preferred polymers have a weight average molecular weight of 30,000 to 80,000 Daltons. Molecular weights are determined according to high-temperature gel permeation chromatography (HT-GPC) using polystyrene standards. The polymers preferably have a polydispersibility of 1.01 to 10, more preferably 1.1 to 3.0, most preferred 1.5 to 2.5.

If desired, a monofunctional aryl halide or aryl boronate, such as, for example,

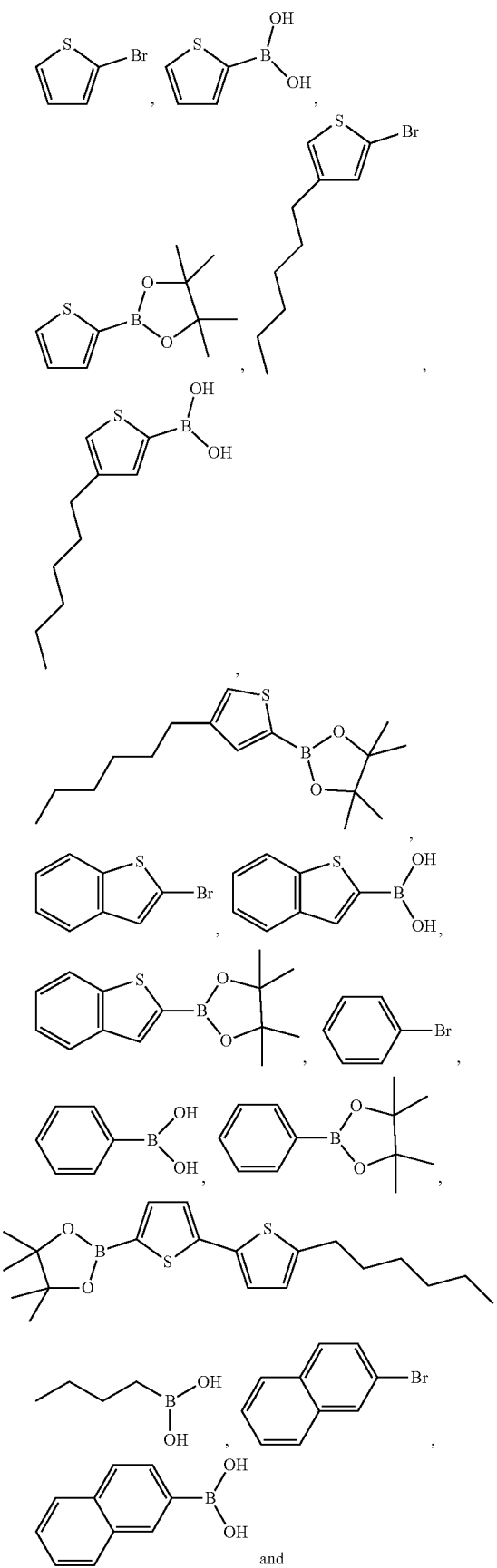

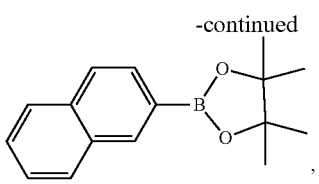
, may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula VII a dihalogenide of formula $X^6$-A-$X^6$ is reacted with a compound of formula $X^{6'}$—[$COM^1$]—$X^{6'}$, or a dihalogenide of formula $X^6$—[$COM^1$]—$X^6$ is reacted with a compound of formula $X^{6'}$-A-$X^{6'}$, wherein $X^{6'}$ is a group —$SnR^{207}R^{208}R^{209}$ and $X^6$ is as defined above, in an inert solvent at a temperature in range from 0° C. to 200° C. in the presence of a palladium-containing catalyst, wherein $R^{207}$, $R^{208}$ and $R^{209}$ are identical or different and are H or $C_1$-$C_6$alkyl, wherein two groups optionally form a common ring and these radicals are branched or unbranched. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tertbutanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using a zinc reagent A-$(ZnX^{12})_2$, wherein $X^{12}$ is halogen and halides, and $COM^1$-$(X^{6'})_2$, wherein $X^{6'}$ is halogen or triflate, or using A-$(X^{6'})_2$ and $COM^1$-$(ZnX^{12})_2$. Reference is, for example, made to E. Negishi et al., Heterocycles 18 (1982) 117-22.

Alternatively, the polymers of the present invention can also be synthesized by the Hiyama reaction using a organosilicon reagent A-$(SiR^{210}R^{211}R^{212})_2$, wherein $R^{210}$, $R^{211}$ and $R^{212}$ are identical or different and are halogen, or $C_1$-$C_6$alkyl, and $COM^1$-$(X^{6'})_2$, wherein $X^{6'}$ is halogen or triflate, or using A-$(X^{6'})_2$ and $COM^1$-$(SiR^{210}R^{211}R^{212})_2$. Reference is, for example, made to T. Hiyama et al., Pure Appl. Chem. 66 (1994) 1471-1478 and T. Hiyama et al., Synlett (1991) 845-853.

Alternatively, the polymers of the present invention can also be synthesized by the direct arylation polymerization reaction using a monomer A-$(H)_2$, and $COM^1$-$(X^{6'})_2$, wherein $X^{6'}$ is halogen, or using A-$(X^{6'})_2$ and $COM^1$-$(H)_2$ wherein $X^{6'}$ is halogen. Reference is, for example, made to P. Homyak et al., Macromolecules 2015, 48, 6978-6986, T. Nakanishi et al., J. Mater. Chem. A, 2015, 3, 4229-4238, or J. Kuwabara, Journal of Polymer Science, Part A: Polymer Chemistry 2016, 54, 2337-2345.

In another embodiment the present invention is directed to homopolymers of the type $(A)_n$. Homopolymers of the type $(A)_n$ can be obtained via Yamamoto coupling of dihalides $X^6$-A-$X^6$, where $X^6$ is halogen, especially Cl, Br, or I, very especially Br. Alternatively homopolymers of the type $(A)_n$ can be obtained via oxidative polymerization of units $X^6$-A-$X^6$, where $X^6$ is hydrogen, e.g. with $FeCl_3$ as oxidizing agent.

Compounds of formula $X^6$—Ar—Y—Ar'—$X^{6'}$ (X) are new, intermediates in the production of the polymer of the present invention and form a further subject of the present invention.

Y, Ar and Ar' are defined in claim 1, and $X^6$ and $X^{6'}$ are independently of each other halogen, especially Cl, Br, or I, very especially Br, or I, $ZnX^{12}$, —$SnR^{207}R^{208}R^{209}$, wherein $R^{207}$, $R^{208}$ and $R^{209}$ are identical or different and are H, or $C_1$-$C_6$alkyl, wherein two radicals optionally form a common ring and these radicals are optionally branched or unbranched and $X^{12}$ is a halogen atom; or —$OS(O)_2CF_3$, —$OS(O)_2$-aryl, —$OS(O)_2CH_3$, —$B(OH)_2$, —$B(OY^1)_2$,

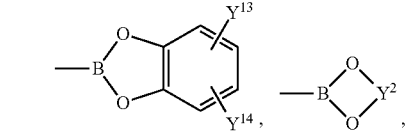

—$BF_4Na$, or —$BF_4K$, wherein $Y^1$ is independently in each occurrence a $C_1$-$C_{10}$alkyl group, and $Y^2$ is independently in each occurrence a $C_2$-$C_{10}$alkylene group, which can optionally be substituted by one, or more $C_1$-$C_8$alkyl groups, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —$C(CH_3)_2C(CH_3)_2$—, —$CH_2C(CH_3)_2CH_2$—, or —$C(CH_3)_2CH_2C(CH_3)_2$—, and $Y^{13}$ and $Y^{14}$ are independently of each other hydrogen, or a $C_1$-$C_{10}$alkyl group.

Examples of compounds of formula (X) are compounds (C-1) to (C-5) shown in claim 23 and the compound of formula

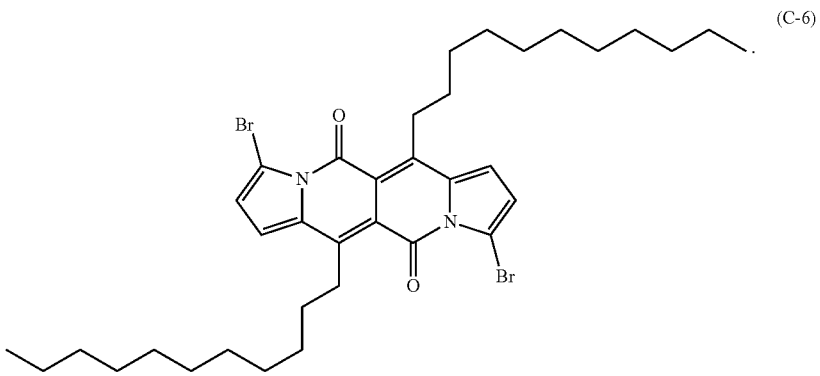 [SMILES: CCCCCCCCCCCc1c2c(=O)n3c(Br)ccc3c(CCCCCCCCCCC)c2c(=O)n2c(Br)ccc12]

(C-6)

In the context of the present invention, the terms halogen, $C_1$-$C_{25}$alkyl ($C_1$-$C_{18}$alkyl), $C_2$-$C_{25}$alkenyl ($C_2$-$C_{18}$alkenyl), $C_{2-25}$alkynyl ($C_{2-18}$alkynyl), aliphatic groups, aliphatic hydrocarbon groups, alkylene, alkenylene, cycloaliphatic hydrocarbon groups, cycloalkyl, cycloalkenyl groups, $C_1$-$C_{25}$alkoxy ($C_1$-$C_{18}$alkoxy), $C_1$-$C_{18}$perfluoroalkyl, carbamoyl groups, $C_6$-$C_{24}$aryl ($C_6$-$C_{18}$aryl), $C_7$-$C_{25}$aralkyl and heteroaryl are each defined as follows—unless stated otherwise:

Halogen is fluorine, chlorine, bromine and iodine, especially fluorine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

Halogenated $C_1$-$C_{25}$alkyl ($C_1$-$C_{25}$haloalkyl) is a $C_1$-$C_{25}$alkyl group, where a part or all of the hydrogen atoms are replaced by halogen atoms, such as, for example, $CF_3$.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-25}$alkynyl ($C_{2-18}$alkynyl) is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_{1-25}$alkanoyl ($C_{2-18}$alkanoyl) refers to a group $R^w$—(C=O)—, with $R^w$ is $C_{1-25}$alkyl ($C_{1-18}$alkyl). Specific examples thereof include an acetyl group, a n-propanoyl group, an isopropanoyl group, a n-butyroyl group, and a tert-butyroyl group.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

A cycloalkyl-alkyl group is an alkyl group substituted by a cycloalkyl group, e.g. cyclohexyl-methyl.

A group of the formula IV wherein two groups $R^{22}$ to $R^{26}$ which are in the neighborhood of each other, together represent alkylene or alkenylene having up to 8 carbon atoms, thereby forming a ring, is e.g. a group of the formula

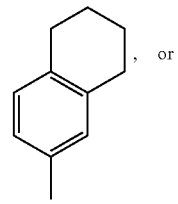

(XXXII)

, or

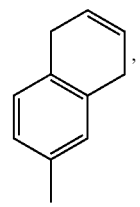

(XXXIII)

, wherein in the group of the formula XXXII $R^{23}$ and $R^{24}$ together represent 1,4-butylene and in the group of the formula XXXIII $R^{23}$ and $R^{24}$ together represent 1,4-but-2-en-ylene.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "$C_1$-$C_{25}$alkylthio group" means the same groups as the alkoxy groups, except that the oxygen atom of the ether linkage is replaced by a sulfur atom.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3$ $CF_3$, and —$C(CF_3)_3$.

A $C_3$-$C_{12}$cycloalkyl, or $C_4$-$C_{12}$cycloalkyl group is typically a $C_5$-$C_{12}$cycloalkyl group, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

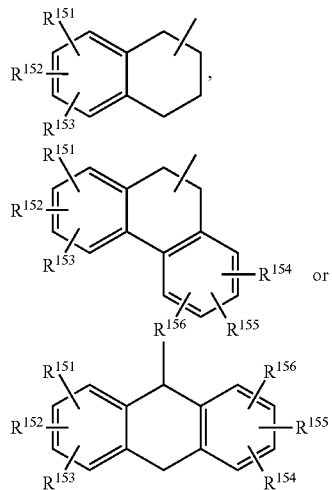

in particular

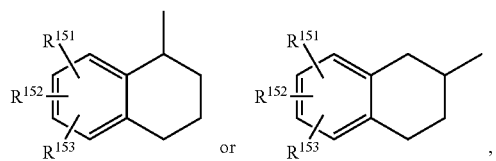

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl ($C_6$-$C_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, thienothienyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{25}$alkyl interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H.

$C_1$-$C_{25}$alkyl interrupted by one or more S is, for example, $(CH_2CH_2S)_{1-9}$—$R^x$, where $R^x$ is H or $C_1$-$C_{10}$alkyl, $CH_2$—$CH(SR^{y'})$—$CH_2$—S—$R^y$, where $R^y$ is $C_1$-$C_{18}$alkyl, and $R^{y'}$ embraces the same definitions as $R^y$ or is H.

If a substituent, such as, for example $T^3$, occurs more than one time in a group, it can be different in each occurrence.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

The polymers of the present invention can be blended with compounds of formula (I) according to the present invention, or small molecules described, for example, in WO2009/047104, WO2010108873, WO009/047104, U.S. Pat. No. 6,690,029, WO2007082584, and WO2008107089.

The polymer can contain a small molecule, or a mixture of two, or more small molecule compounds.

Accordingly, the present invention also relates to an organic semiconductor material, layer or component, comprising a polymer according to the present invention.

The polymers of the invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radiofrequency identification (RFID) tags, backplanes for flexible displays (for use in, for example, personal computers, cell phones, or handheld devices), smart cards, medical devices, memory devices, sensors (e.g. light-, image-, bio-, chemo-, mechanical- or temperature sensors), especially photodiodes, or security devices and the like.

A further aspect of the present invention is an organic semiconductor material, layer or component comprising one or more polymers of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 μm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
  a source electrode,
  a drain electrode,
  a gate electrode,
  a semiconducting layer,
  one or more gate insulator layers, and
  optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably, the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the person skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, $ZnO$ etc.), conductive particles (Au, Ag etc.), and insulator materials like the ones described for the gate dielectric (PET, PS etc.). As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
  (a) a cathode (electrode),
  (b) optionally a transition layer, such as an alkali halogenide, especially lithium fluoride,
  (c) a photoactive layer,
  (d) optionally a smoothing layer,
  (e) an anode (electrode),
  (f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. As stated above, the photoactive layer may also contain a polymeric binder. The ratio of the polymers of formula (V) to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA).

For heterojunction solar cells the active layer comprises preferably a mixture of a polymer of the present invention and a fullerene, such as [60]PCBM (=6,6-phenyl-$C_{61}$-butyric acid methyl ester), or [70]PCBM, in a weight ratio of 1:1 to 1:3. The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of any semi-conducting polymer, such as, for example, a polymer of the present invention, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a polymer of the present invention as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

The following examples are included for illustrative purposes only and do not limit the scope of the claims. Unless otherwise stated, all parts and percentages are by weight.

Weight-average molecular weight (Mw) and polydispersity (Mw/Mn=PD) are determined by Heat Temperature Gel Permeation Chromatography (HT-GPC) [Apparatus: GPC PL 220 from Polymer laboratories (Church Stretton, UK; now Varian) yielding the responses from refractive index (RI), Chromatographic conditions: Column: 3 "PLgel Olexis" column from Polymer Laboratories (Church Stretton, UK); with an average particle size of 13 im (dimensions 300×8 mm I.D.) Mobile phase: 1,2,4-trichlorobenzene purified by vacuum distillation and stabilised by butylhydroxytoluene (BHT, 200 mg/l), Chromatographic temperature: 150° C.; Mobile phase flow: 1 ml/min; Solute concentration: about 1 mg/ml; Injection volume: 200 il; Detection: RI, Procedure of molecular weight calibration: Relative calibration is done by use of a set of 10 polystyrene calibration standards obtained from Polymer Laboratories (Church Stretton, UK) spanning the molecular weight range from 1,930,000 Da-5,050 Da, i.e., PS 1,930,000, PS 1,460,000, PS 1,075,000, PS 560,000, PS 330,000, PS 96,000, PS 52,000, PS 30,300, PS 10,100, PS 5,050 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

Synthesis of dipyrrolo[1,2-b:1,2'-g][2,6]naphthyridine-5,11-dione (1a (A-1)) by the Condensation of 2-fromylpyrrole and succinyl chloride

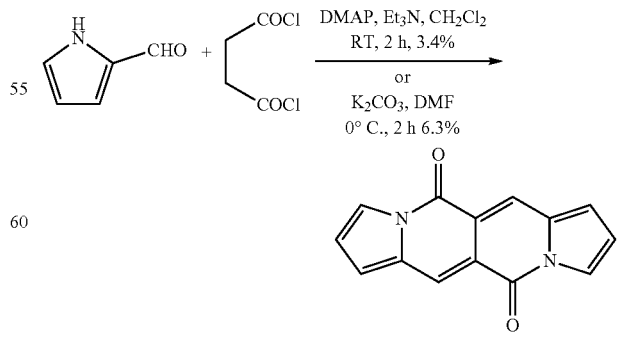

Procedure 1.

2-Formylpyrrole (1.14 g, 12.0 mmol) and 4-dimethylaminopyridine (DMAP, 98 mg, 0.80 mmol) were dissolved in 25 ml of dry dichloromethane. The mixture was stirred under an argon atmosphere and triethylamine (2.2 ml, 15.8 mmol) was added. Then succinyl chloride (0.44 ml, 4.0 mmol) was added dropwise. The stirring was continued for 2 h at room temperature. Reaction mixture contained a large amount of a black tar, which was removed by filtration through Celite. Celite was then washed with dichloromethane. To the combined filtrates water was added and the layers were separated. Aqueous layer was extracted three times with dichloromethane. Combined organic layers were washed twice with water and dried over $Na_2SO_4$. The drying agent was filtered off and the solvents were evaporated. The product was purified by column chromatography (silica, dichloromethane:acetone 19:1) and recrystallized by slow addition of pentane to the solution of product in small amount of hot chloroform. Compound 1a (32 mg, 3.4% yield) was obtained as brown powder. Mp. >280° C. (decomposition). $^1$H NMR (500 MHz, $CDCl_3$) δ 7.97 (s, 1H, CH (6-membered ring)), 7.81 (dd, J=3.1, 0.7 Hz, 1H, pyrrole: 5-H), 6.80 (dd, J=3.6, 1.2 Hz, 1H, pyrrole: 3-H), 6.54 (t, J=3.4 Hz, 1H, pyrrole: 4-H). $^{13}$C NMR (126 MHz, $CDCl_3$) δ 158.4, 131.7, 125.2, 123.6, 120.3, 118.4, 116.2. HRMS (EI) calcd for $C_{14}H_8N_2O_2(M^+)$: 236.0586; found: 236.0580. Elemental analysis calcd (%) for $C_{14}H_8N_2O_2$: C, 71.18, H, 3.41, N, 11.86; found: C, 71.19, H, 3.60, N, 11.65.

In addition to the dye 1a, unreacted 2-formylpyrrole (0.74 g, 65% of the initial amount) was also separated from the reaction mixture.

Procedure 2.

A mixture consisting of 2-formylpyrrole (238 mg, 2.5 mmol), powdered potassium carbonate (1.38 g, 10.0 mmol) and 10 ml of dry DMF was stirred under an argon atmosphere at 0° C. The solution of succinyl chloride (110 μl, 1.0 mmol) in 1.0 ml of dry dichloromethane was added dropwise. The stirring was continued for 2 h at 0° C. The reaction mixture was then diluted with water and passed through Celite, which was washed twice with water. Then two portions of ethanol and three portions of chloroform were passed through Celite in order to recover the product. These filtrates were combined and washed twice with water and dried over $Na_2SO_4$. The drying agent was filtered off and the solvents were evaporated. The product was recrystallized by slow addition of pentane to its solution in small amount of hot chloroform. Compound 1a (15 mg, 6.4% yield) was obtained as a brown powder. The product was identified by the comparison with previously synthesized sample.

Example 2

Synthesis of dipyrrolo[1,2-b:1',2'-g][2,6]naphthyridine-5,11-dione (1a (A-1)) by the Vilsmeier-Haack Formylation of 1,4-di(pyrrol-1-yl)butane-1,4-dione (3)

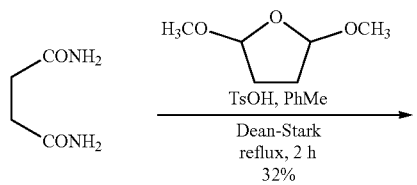

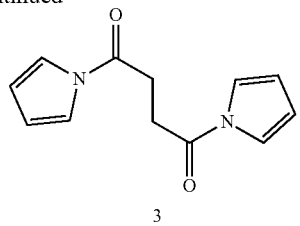

A mixture of succinamide (1.16 g, 10 mmol), 2,5-dimethoxytetrahydrofuran (3.9 ml, 30 mmol), para-toluenesulfonic acid monohydrate (190 mg, 1.0 mmol) and 25 ml of toluene was refluxed for 2 h under the Dean-Stark apparatus. The reaction mixture was cooled and the black precipitate, which was formed in the reaction, was filtered off and washed with chloroform. The filtrates were washed with water three times and dried over $Na_2SO_4$. Solvents were evaporated and the product was purified by the column chromatography (silica, hexanes:dichloromethane 1:2). The product was recrystallized from ethanol. Compound 3 (632 mg, 29% yield) was obtained as a white powder. Mp. 162-164° C. $^1$H NMR (500 MHz, $CDCl_3$) δ 7.36 (br s, 4H, pyrrole: 2-H and 5-H), 6.36-6.27 (m, 4H, pyrrole: 3-H and 4-H), 3.34 (s, 4H, $CH_2CH_2$). $^{13}$C NMR (126 MHz, $CDCl_3$) δ 168.2, 119.0, 113.5, 28.9. HRMS (EI) calcd for $C_{12}H_{12}N_2O_2$ ($M^+$): 216.0899; found: 216.0910. Elemental analysis calcd (%) for $C_{12}H_{12}N_2O_2$: C, 66.65, H, 5.59, N, 12.96; found: C, 66.86, H, 5.73, N, 12.92.

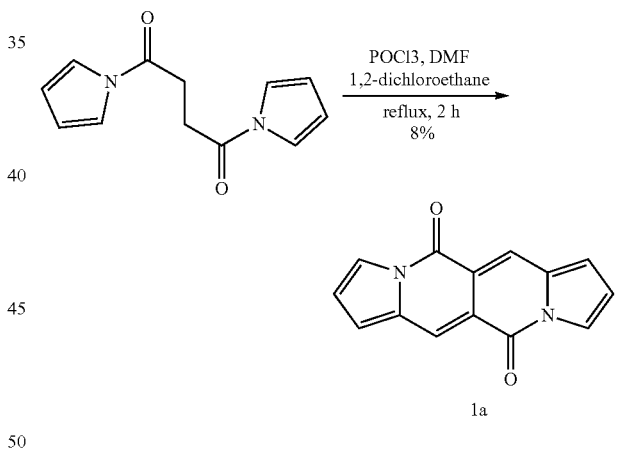

Under an argon atmosphere, to the solution of compound 3 (432 mg, 2.0 mmol) in 10 ml of dry 1,2-dichloroethane was added DMF (390 μl, 5.0 mmol). Then phosphorus(V) oxychloride (480 μl, 5.2 mmol) was added dropwise and the mixture was refluxed for 2 h. The reaction was quenched by the addition of saturated aqueous solution of sodium bicarbonate (10 ml). The resulting mixture was stirred for 5 min and diluted with dichloromethane and water. Layers were separated and the aqueous layer was extracted three times with dichloromethane. The combined organic layers were washed with water and dried over $Na_2SO_4$. The products were separated by column chromatography (silica, dichloromethane:acetone 19:1). Dye 1a was recrystallized by slow addition of pentane to its solution in small amount of hot chloroform. The product was obtained as a brown powder (39 mg, 8.3% yield) and identified by the comparison with previously synthesized sample. In addition to compound 1a, 2-formylpyrrole (127 mg, 33% yield) was also obtained.

Example 3

Acylation of Compound 3 (A-2) with Acetic Acid

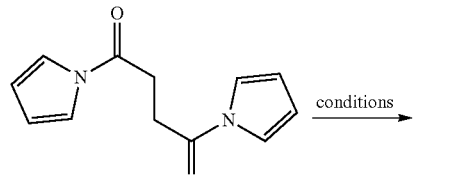

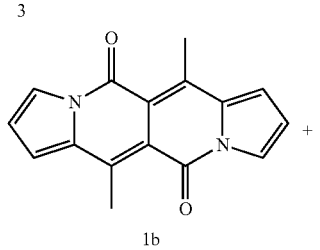

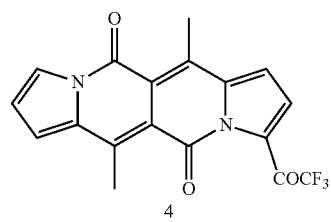

Compound 3 (216 mg, 1.0 mmol) was dissolved in 4.5 ml of dry dichloromethane under an argon atmosphere, and the solution was cooled to 0° C. Trifluoroacetic anhydride (3.0 ml, 22 mmol) and acetic acid (460 μl, 8.0 mmol) were added and the resulting mixture was stirred at 0° C. for 10 min and then at room temperature for 4 h. The reaction mixture was then poured into a beaker containing 20 ml of saturated aqueous $NaHCO_3$ and mixed ($CO_2$ gas evolved). When the evolution of carbon dioxide was no longer observed, layers were separated. Aqueous layer was extracted three times with chloroform, and the combined organic layers were washed with water and dried over $Na_2SO_4$. Obtained mixture was separated using column chromatography (silica, hexanes:dichloromethane 1:2→pure dichloromethane) to give two crude products, compounds 4 and 1b, which were recrystallized by slow addition of methanol to a hot solution of the dye in small amount of chloroform.

6,12-Dimethyl-3-trifluoroacetyldipyrrolo[1,2-b:1',2'-g][2,6]naphthyridine-5,11-dione (4)

Compound 4 (34 mg, 9.4% yield) was obtained as a dark brown powder. Mp. >180° C. (decomposition). $^1$H NMR (500 MHz, $CDCl_3$) δ 7.84 (d, J=1.9 Hz, 1H, DPND: 9-H), 7.19 (d, J=3.9 Hz, 1H, DPND: 1-H), 6.97 (d, J=3.1 Hz, 1H, DPND: 7-H), 6.89 (d, J=4.0 Hz, 1H, DPND: 2-H), 6.56 (t, J=3.4 Hz, 1H, DPND: 8-H), 2.86 (s, 3H, $CH_3$), 2.81 (s, 3H, $CH_3$). $^{13}$C NMR (126 MHz, $CDCl_3$) δ 174.1-173.5 (m), 158.4, 143.3, 139.4, 137.8, 133.4, 128.4, 124.3, 124.3, 123.9, 119.1, 118.9, 116.0, 116.1 (q, J=290 Hz), 114.80, 114.54, 18.27, 17.81. HRMS (ESI) calcd for $C_{18}H_{11}F_3N_2O_3Na$ (M+Na$^+$): 383.0619; found: 383.0606. Elemental analysis calcd (%) for $C_{18}H_{11}F_3N_2O_3$: C, 60.01, H, 3.08, N, 7.78; found: C, 59.92, H, 3.02, N, 7.68.

6,12-Dimethyldipyrrolo[1,2-b:1',2'-g][2,6]naphthyridine-5,11-dione (1b)

Compound 1b (33 mg, 12% yield) was obtained as a dark brown powder. Mp. >280° C. (decomposition). $^1$H NMR (500 MHz, $CDCl_3$) δ 7.84 (d, J=1.7 Hz, 2H, pyrrole: 5-H), 6.95-6.85 (m, 2H, pyrrole: 3-H), 6.54 (t, J=3.3 Hz, 2H, pyrrole: 4-H), 2.85 (s, 6H, $CH_3$). $^{13}$C NMR (126 MHz, $CDCl_3$) δ 159.1, 140.5, 133.7, 122.7, 117.1, 115.6, 115.0, 18.3. HRMS (ESI) calcd for $C_{16}H_{12}N_2O_2Na$ (M+Na$^+$): 287.0796; found: 287.0786. Elemental analysis calcd (%) for $C_{16}H_{12}N_2O_2$: C, 72.72, H, 4.58, N, 10.60; found: C, 72.79, H, 4.50, N, 10.62.

Example 4

General Procedure for the Preparation of 6,12-Disubstituted DPND Derivatives (1b-1e)

Compound 3 (108 mg, 0.50 mmol) was dissolved in 3.0 ml of dry dichloromethane under an argon atmosphere, and the solution was cooled to 0° C. Subsequently, to the reaction flask were slowly added: carboxylic acid (3.0 mmol), trifluoroacetic anhydride (830 μl, 6.0 mmol) and trifluoroacetic acid (230 μl, 3.0 mmol). The resulting mixture was stirred at room temperature for given time. The reaction mixture was then slowly poured into a beaker containing 20 ml of vigorously stirred saturated aqueous $NaHCO_3$ ($CO_2$ evolved). When the evolution of carbon dioxide was no longer observed, the mixture was diluted with chloroform and layers were separated. Aqueous layer was extracted four times with chloroform, and the combined organic layers were washed with water and dried over $Na_2SO_4$. The product was purified by column chromatography and recrystallized (see below for details).

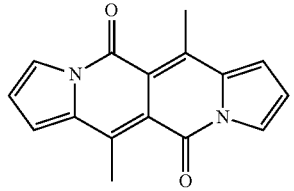 [SMILES: Cc1c2c(=O)n3cccc3c(C)c2c(=O)n2cccc12]

6,12-Dimethyldipyrrolo[1,2-b:1',2'-g][2,6]naphthyridine-5,11-dione (1b (A-2))

Carboxylic acid used: acetic acid (172 μl, 3.0 mmol). Reaction time: 5 h. Product was purified using column chromatography (silica, dichloromethane) and recrystallized by slow addition of methanol to a hot solution of the dye in small amount of chloroform. Compound 1b (23 mg, 17% yield) was obtained as a dark brown powder and identified by the comparison with previously synthesized sample.

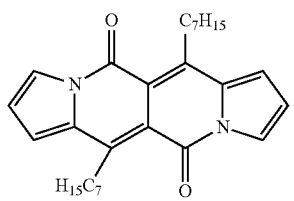

6,12-Diheptyldipyrrolo[1,2-b:1',2'-g][2,6]naphthyridine-5,11-dione (1c (A-3))

Carboxylic acid used: caprylic acid (475 μl, 3.0 mmol). Reaction time: 3 h. Product was purified using column chromatography (silica, hexanes:dichloromethane 2:1→1:1) and recrystallized by slow addition of methanol to a solution of the dye in small amount of dichloromethane. Compound 1c (63 mg, 29% yield) was obtained as a red solid. Mp. 107-109° C. $^1$H NMR (500 MHz, CDCl$_3$) δ 7.84 (dd, J=3.0, 1.3 Hz, 2H, pyrrole: 5-H), 6.87 (dd, J=3.7, 1.3 Hz, 2H, pyrrole: 3-H), 6.54 (t, J=3.4 Hz, 2H, pyrrole: 4-H), 3.35-3.22 (m, 4H, CH$_2$(CH$_2$)$_5$CH$_3$), 1.76-1.62 (m, 4H, CH$_2$(CH$_2$)$_5$CH$_3$), 1.58-1.47 (m, 4H, CH$_2$(CH$_2$)$_5$CH$_3$), 1.44-1.35 (m, 4H, CH$_2$(CH$_2$)$_5$CH$_3$), 1.35-1.23 (m, 8H, CH$_2$(CH$_2$)$_5$CH$_3$), 0.89 (t, J=6.9 Hz, 6H, CH$_2$(CH$_2$)$_5$CH$_3$). $^{13}$C NMR (126 MHz, CDCl$_3$) δ 158.6, 145.6, 133.4, 122.6, 116.7, 115.6, 114.6, 32.1, 31.2, 30.6, 30.5, 29.4, 22.8, 14.3. HRMS (ESI) calcd for C$_{28}$H$_{37}$N$_2$O$_2$ (M+H$^+$): 433.2855; found: 433.2848. Elemental analysis calcd (%) for C$_{28}$H$_{36}$N$_2$O$_2$: C, 77.74, H, 8.39, N, 6.48; found: C, 77.48, H, 8.48, N, 6.33.

The synthesis of compound 1c was repeated in 10-times larger scale, using the same procedure and following amounts of reagents: compound 3 (1.08 g, 5.00 mmol), caprylic acid (4.75 ml, 30 mmol), trifluoroacetic anhydride (8.3 ml, 60 mmol), trifluoroacetic acid (2.30 ml, 30 mmol) and dichloromethane (30 ml) as a solvent. After 3.5 h of the reaction at room temperature 525 mg of product 1c was obtained (23% yield).

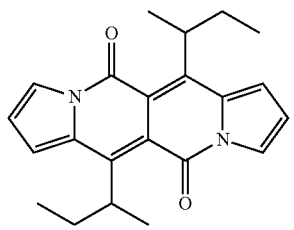 [SMILES: CCC(C)c1c2c(=O)n3cccc3c(C(C)CC)c2c(=O)n2cccc12]

6,12-Di-sec-butyldipyrrolo[1,2-b:1',2'-g][2,6]naphthyridine-5,11-dione (1d (A-4))

Carboxylic acid used: 2-methylbutyric acid (330 μl, 3.0 mmol). Reaction time: 6 h. Product was purified using column chromatography (silica, hexanes:dichloromethane 1:1) and recrystallized by slow addition of methanol to a solution of the dye in small amount of dichloromethane. Compound 1d (36 mg, 21% yield) was obtained as red crystals. Mp. 176-178° C. $^1$H NMR (500 MHz, CDCl$_3$) δ 7.79 (dd, J=2.9, 1.0 Hz, 2H, pyrrole: 5-H), 7.01 (d, J=3.0 Hz, 2H, pyrrole: 3-H), 6.50 (t, J=3.4 Hz, 2H, pyrrole: 4-H), 4.74 (br s, 2H, C—(CH$_3$)CH$_2$CH$_3$), 2.00-1.90 (m, 2H, CH(CH$_3$)CH$_2$CH$_3$), 1.90-1.79 (m, 2H, CH(CH$_3$)CH$_2$CH$_3$), 1.46 (dd, J=7.1, 1.7 Hz, 6H, CH(CH$_3$)CH$_2$CH$_3$), 0.96 (t, J=7.4 Hz, 6H, CH(CH$_3$)CH$_2$CH$_3$). $^{13}$C NMR (126 MHz, CDCl$_3$) δ 159.7, 150.7, 130.3, 121.6, 118.7, 116.8, 115.2, 35.9, 30.6, 20.5, 13.1. HRMS (ESI) calcd for C$_{22}$H$_{24}$N$_2$O$_2$Na (M+Na$^+$): 371.1735; found: 371.1724. Elemental analysis calcd (%) for C$_{22}$H$_{24}$N$_2$O$_2$: C, 75.83, H, 6.94, N, 8.04; found: C, 75.63, H, 6.89, N, 7.94.

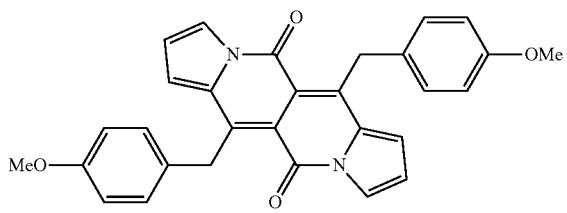 [SMILES: COc1ccc(Cc2c3c(=O)n4cccc4c(Cc4ccc(OC)cc4)c3c(=O)n3cccc23)cc1]

6,12-Bis(4-methoxybenzyl)dipyrrolo[1,2-b:1',2'-g][2,6]naphthyridine-5,11-dione (1e (A-5))

Carboxylic acid used: 4-methoxyphenylacetic acid (499 mg, 3.0 mmol). Reaction time: 6 h. Product was purified using column chromatography (silica, dichloromethane→dichloromethane:ethyl acetate 19:1) and recrystallized by slow addition of methanol to a solution of the dye in small amount of chloroform. Compound 1e (25 mg, 10.5% yield) was obtained as red crystals. Mp. >270° C. (decomposition). $^1$H NMR (500 MHz, CDCl$_3$) δ 7.82 (dd, J=3.0, 1.2 Hz, 2H, pyrrole: 5-H), 7.24-7.18 (AA'BB', 4H, benzene: 2-H and 6-H), 6.91 (dd, J=3.7, 1.2 Hz, 2H, pyrrole: 3-H), 6.83-6.78 (AA'BB', 4H, benzene: 3-H and 5-H), 6.52 (t, J=3.4 Hz, 2H, pyrrole: 4-H), 4.69 (s, 4H, CH$_2$Ar), 3.75 (s, 6H, OCH$_3$). $^{13}$C NMR (126 MHz, CDCl$_3$) δ 158.2, 158.0, 142.4, 133.6, 130.8, 129.3, 123.1, 118.2, 115.8, 115.3, 113.9, 55.2, 34.7. HRMS (ESI) calcd for C$_{30}$H$_{24}$N$_2$O$_4$Na (M+Na$^+$): 499.1634; found: 499.1624. Elemental analysis calcd (%) for C$_{30}$H$_{24}$N$_2$O$_4$: C, 75.62, H, 5.08, N, 5.88 found: C, 75.65, H, 5.10, N, 5.92.

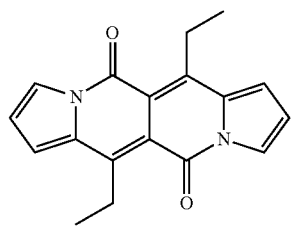 [SMILES: CCc1c2c(=O)n3cccc3c(CC)c2c(=O)n2cccc12]

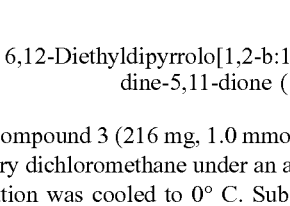

6,12-Diethyldipyrrolo[1,2-b:1',2'-g][2,6]naphthyridine-5,11-dione (1f (A-6))

Compound 3 (216 mg, 1.0 mmol) was dissolved in 6.0 ml of dry dichloromethane under an argon atmosphere, and the solution was cooled to 0° C. Subsequently, to the reaction flask were slowly added: propionic anhydride (380 μl, 3.0 mmol), trifluoroacetic anhydride (1.10 ml, 7.9 mmol) and trifluoroacetic acid (920 μl, 12.0 mmol). The resulting mixture was stirred at room temperature for 2 h. The reaction mixture was then slowly poured into a beaker containing 20 ml of vigorously stirred saturated aqueous NaHCO$_3$ (CO$_2$ evolved). When the evolution of carbon dioxide was no longer observed, the mixture was diluted with chloroform and layers were separated. Aqueous layer was extracted four times with chloroform, and the combined organic layers were washed with water and dried over Na$_2$SO$_4$. The product was purified by column chromatography (silica, toluene) and recrystallized by slow addition of methanol to the solution of product in small amount of dichloromethane. Compound 1f (67 mg, 23%) was obtained as dark red crystals. Mp. 226-229° C. $^1$H NMR (500 MHz, CDCl$_3$) δ 7.84 (dd, J=3.0, 1.3 Hz, 2H, pyrrole: 5-H), 6.89 (dd, J=3.6, 1.3 Hz, 2H, pyrrole: 3-H), 6.55 (t, J=3.4 Hz, 2H, pyrrole: 4-H), 3.33 (q, J=7.4 Hz, 4H, CH$_2$CH$_3$), 1.35 (t, J=7.4 Hz, 6H, CH$_2$OCH$_3$). $^{13}$C NMR (126 MHz, CDCl$_3$) δ 158.5, 146.8, 133.0, 122.7, 116.7, 115.7, 114.5, 24.4, 14.5. HRMS (ESI) calcd for C$_{18}$H$_{16}$N$_2$O$_4$Na (M+Na$^+$): 315.1109; found: 315.1097.

Synthesis of Various 6,12-Disubstituted DPND Derivatives.[a]

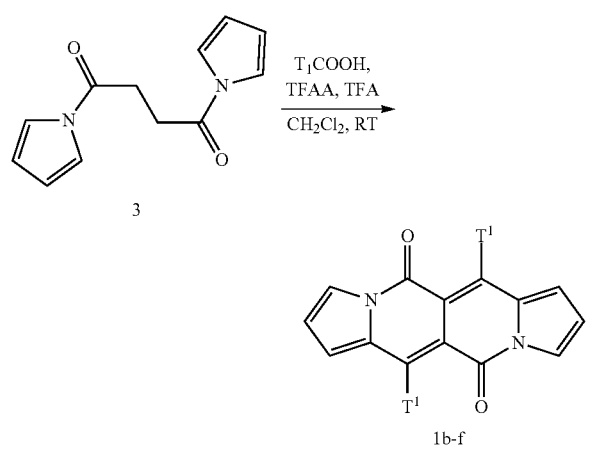

Example 4

3,9-Dibromo-6,12-diheptyldipyrrolo[1,2-b:1',2'-g][2,6]naphthyridine-5,11-dione (5 (C-1))

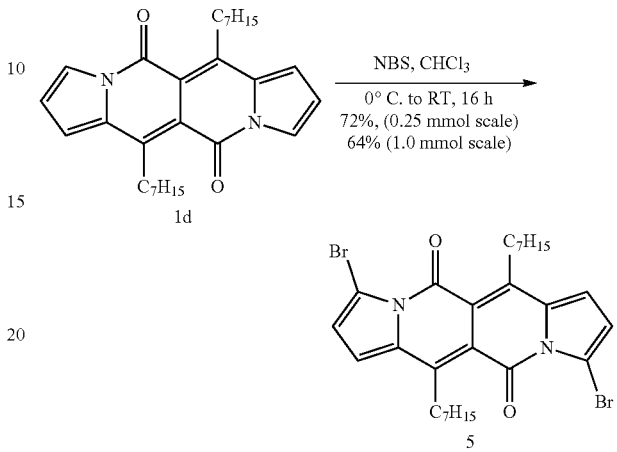

A solution of compound 1c (108 mg, 0.25 mmol) in 5 ml of chloroform was stirred at 0° C. (water-ice bath). Freshly recrystallized N-bromosuccinimide (93 mg, 0.52 mmol) was added and the obtained mixture was stirred in the darkness (protection with aluminium foil) for 16 h. During this time ice in the ice bath melted and the reaction mixture warmed to the room temperature. The reaction mixture was diluted with chloroform, washed with water three times, and dried over Na$_2$SO$_4$. The product was purified using column chromatography (silica, hexanes:dichloromethane 3:1→2:1) and recrystallized by slow addition of methanol to a solution of the dye in small amount of dichloromethane. Compound 5 (107 mg, 72% yield) was obtained as a red solid. Mp. 133-135° C. $^1$H NMR (500 MHz, CDCl$_3$) δ 6.81 (d, J=4.0 Hz, 2H, pyrrole: 3-H), 6.59 (d, J=4.0 Hz, 2H, pyrrole: 4-H), 3.24-3.05 (m, 4H, CH$_2$(CH$_2$)$_5$CH$_3$), 1.71-1.59 (m, 4H, CH$_2$(CH$_2$)$_5$CH$_3$), 1.55-1.46 (m, 4H, CH$_2$(CH$_2$)$_5$CH$_3$), 1.41-1.23 (m, 12H, CH$_2$(CH$_2$)$_5$CH$_3$), 0.89 (t, J=6.8 Hz, 6H, CH$_2$(CH$_2$)$_5$ CH$_3$). $^{13}$C NMR (126 MHz, CDCl$_3$) δ 158.9, 143.3,

| Carboxylic acid | Reaction time | Product | T$^1$ | Yield |
|---|---|---|---|---|
| CH$_3$CO$_2$H | 5 h | 1b (A-2) | CH$_3$ | 17% |
| C$_7$H$_{15}$CO$_2$H | 3 h[c] | 1c (A-3) | C$_7$H$_{15}$ | 29%[c] |
|  | 3.5 h[d] |  |  | 23%[d] |
|  | 6 h | 1d (A-4) | sec-butyl | 21% |
| 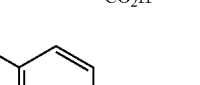 | 6 h | 1e (A-5) | 4-methoxybenzyl | 10.5% |
| (C$_2$H$_5$CO)$_2$O [b] | 2 h | 1f (A-6) | C$_2$H$_5$ | 23% |

[a] Reagents proportions: 3 (0.5 mmol), carboxylic acid (3 mmol), TFAA (6 mmol), TFA (3 mmol).
[b] Propionic anhydride used instead of carboxylic acid.
[c] 0.5 mmol scale.
[d] 5.0 mmol scale.

135.0, 120.5, 115.8, 115.4, 106.6, 31.9, 30.3, 30.2 (2 signals), 29.2, 22.7, 14.1. HRMS (ESI) calcd for $C_{28}H_{34}Br_2N_2O_2$ ($M^+$): 588.0987; found: 588.0985. Elemental analysis calcd (%) for $C_{28}H_{34}Br_2N_2O_2$: C, 56.96, H, 5.80, N, 4.74; found: C, 56.98, H, 5.77, N, 4.76.

The synthesis of compound 5 was repeated in 4-times larger scale, using the same procedure and following amounts of reagents: compound 1c (433 mg, 1.00 mmol), N-bromosuccinimide (374 mg, 2.10 mmol) and chloroform (15 ml) as a solvent. 379 mg of the product 5 was obtained (64% yield).

Example 5

3,9-Dicyano-6,12-diheptyldipyrrolo[1,2-b:1',2'-g][2,6]naphthyridine-5,11-dione (6 (A-7))

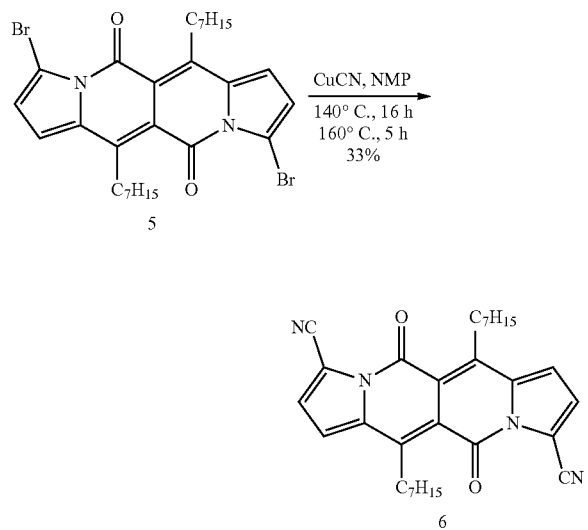

A mixture of compound 5 (59 mg, 0.10 mmol), copper(I) cyanide (20 mg, 0.22 mmol) and 2 ml of dry NMP was stirred under argon at 140° C. for 16 h and at 160° C. for 5 h. The mixture was diluted with water and passed through Celite, which was washed with water. Then the product was extracted from Celite with one portion of ethanol and three portions of chloroform. The organic filtrates were combined, washed with water twice and dried over $Na_2SO_4$. Product was purified by column chromatography (silica, hexanes: dichloromethane 2:3). After evaporation of eluent 16 mg of product was obtained (33% yield), which was recrystallized by slow addition of methanol to warm solution of the dye in small amount of chloroform. Compound 6 (11 mg, 23% yield) was obtained as red crystals. Mp. 222-225° C. $^1$H NMR (500 MHz, $CDCl_3$) δ 7.19 (d, J=4.0 Hz, 2H, pyrrole: 3-H), 6.92 (d, J=4.0 Hz, 2H, pyrrole: 4-H), 3.43-3.15 (m, 4H, $CH_2(CH_2)_5CH_3$), 1.76-1.62 (m, 4H, $CH_2(CH_2)_5CH_3$), 1.59-1.47 (m, 4H, $CH_2(CH_2)_5CH_3$), 1.42-1.25 (m, 12H, $CH_2(CH_2)_5CH_3$), 0.90 (t, J=6.8 Hz, 6H, $CH_2(CH_2)_5CH_3$). $^{13}$C NMR (126 MHz, $CDCl_3$) δ 156.8, 146.6, 136.2, 127.0, 116.9, 116.0, 112.5, 106.4, 31.8, 31.1, 30.2, 30.1, 29.1, 22.7, 14.1. HRMS (ESI) calcd for $C_{30}H_{34}N_4O_2Na$ ($M+Na^+$): 505.2579; found: 505.2574.

Example 6

General Procedure for the Sonogashira Coupling of Compound 5 (C-1) with Para-Substituted Phenylacetylenes—Synthesis of Compounds 7a-d

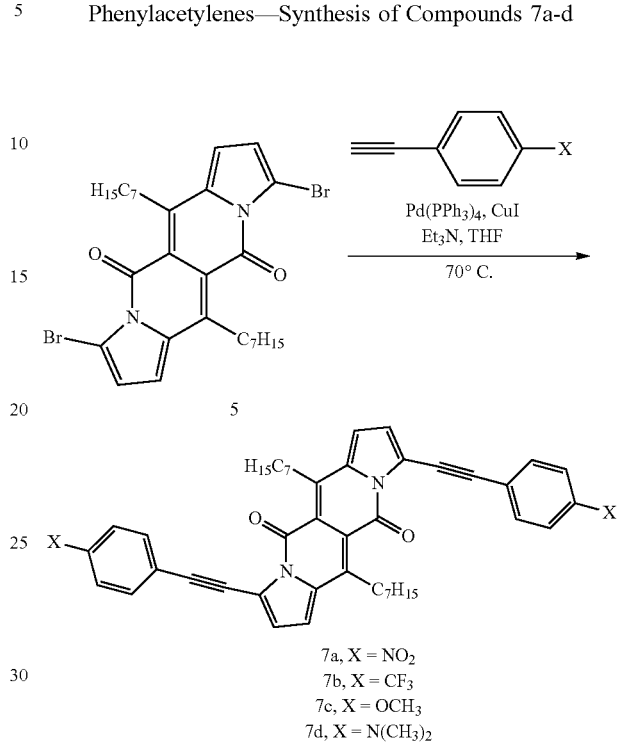

7a, X = $NO_2$
7b, X = $CF_3$
7c, X = $OCH_3$
7d, X = $N(CH_3)_2$

In a Schlenck flask containing a magnetic stirring bar were placed: bromoderivative 5 (0.10 mmol, 59 mg), copper (I) iodide (1.9 mg, 0.010 mmol), tetrakis(triphenylphosphine)palladium(0) (5.8 mg, 0.005 mmol), and para-substituted phenylacetylene (0.30 mmol). The vessel was evacuated and backfilled with argon (3 times) and anhydrous, degassed THF was added (3 ml) followed by dry triethylamine (56 µl, 0.40 mmol). The vessel was tightly closed and again carefully evacuated (until the mixture start to boil) and backfilled with argon (3 times). The content of the flask was stirred for 20 h at 70° C. (above the boiling point). Solvents were evaporated and the product was purified as described below.

6,12-Diheptyl-3,9-bis((4-nitrophenyl)ethynyl)dipyrrolo[1,2-b:1',2'-g][2,6]naphthyridine-5,11-dione (7a (A-8))

Prepared from 4-nitrophenylacetylene (44 mg, 0.30 mmol). Product was purified using column chromatography (silica, hexanes:dichloromethane 1:1→1:2) and recrystallized from toluene. Compound 7a (56 mg, 78% yield) was obtained as a dark violet powder. Mp. >400° C. $^1$H NMR (500 MHz, $CDCl_3$, 50° C.) δ 8.26-8.18 (AA'BB', 4H, benzene: 3-H and 5-H), 7.77-7.67 (AA'BB', 4H, benzene: 2-H and 6-H), 6.89 (s, 4H, pyrrole: 3-H and 4-H), 3.34-3.27 (m, 4H, $CH_2(CH_2)_5CH_3$), 1.80-1.69 (m, 4H, $CH_2(CH_2)_5 CH_3$), 1.61-1.54 (m, 4H, $CH_2(CH_2)_5CH_3$), 1.44-1.23 (m, 12H, $CH_2(CH_2)_5CH_3$), 0.90 (t, J=6.9 Hz, 6H, $CH_2(CH_2)_5 CH_3$). $^{13}$C NMR (126 MHz, $CDCl_3$, 50° C.) δ 158.4, 147.5, 144.3, 135.5, 132.2, 130.3, 123.8, 118.6, 116.9, 116.3, 96.2, 88.1, 32.1, 31.0, 30.5 (2 signals), 29.2, 22.8, 14.2. Elemental analysis calcd (%) for $C_{44}H_{42}N_4O_6$: C, 73.11, H, 5.86, N, 7.75; found: C, 73.20, H, 5.93, N, 7.71.

6,12-Diheptyl-3,9-bis((4-(trifluoromethyl)phenyl)ethynyl)dipyrrolo[1,2-b:1',2'-g][2,6]naphthyridine-5,11-dione (7b (A-9))

Prepared from 4-(trifluoromethyl)phenylacetylene (51 mg, 0.30 mmol). Product was purified using column chromatography (silica, hexanes:dichloromethane 4:1→3:7) and recrystallized by slow addition of methanol to hot solution of the dye in small amount of chloroform. Compound 7b (44 mg, 57% yield) was obtained as a dark green powder. Mp. 200-203° C. $^1$H NMR (500 MHz, CDCl$_3$) δ 7.76-7.67 (AA'BB', 4H, benzene: 3-H and 5-H), 7.67-7.58 (AA'BB', 4H, benzene: 2-H and 6-H), 6.89 (d, J=4.0 Hz, 2H, pyrrole: 3-H), 6.87 (d, J=4.0 Hz, 2H, pyrrole: 4-H), 3.34-3.23 (m, 4H, CH$_2$(CH$_2$)$_5$CH$_3$), 1.77-1.68 (m, 4H, CH$_2$(CH$_2$)$_5$CH$_3$), 1.59-1.52 (m, 4H, CH$_2$(CH$_2$)$_5$CH$_3$), 1.48-1.40 (m, 4H, CH$_2$(CH$_2$)$_5$CH$_3$), 1.38-1.29 (m, 8H, CH$_2$(CH$_2$)$_5$CH$_3$), 0.89 (t, J=7.0 Hz, 6H, CH$_2$(CH$_2$)$_5$CH$_3$). $^{13}$C NMR (126 MHz, CDCl$_3$) δ 158.5, 144.0, 135.1, 131.8, 125.5, 125.4, 123.4, 118.8, 116.6, 116.1, 96.5, 85.2, 32.1, 30.9, 30.5, 29.9, 29.2, 22.8, 14.3 (signals of CF$_3$ group and adjacent carbon atom were not identified due to low intensities caused by $^{13}$C-$^{19}$F coupling). HRMS (ESI) calcd for $C_{46}H_{42}F_6N_2O_2$(M$^+$): 768.3150; found: 768.3153.

6,12-Diheptyl-3,9-bis((4-methoxyphenyl)ethynyl)dipyrrolo[1,2-b:1',2'-g][2,6]naphthyridine-5,11-dione (7c (A-10))

Prepared from 4-methoxyphenylacetylene (40 mg, 0.30 mmol). Product was purified using column chromatography (silica, hexanes:dichloromethane 3:2→5:4) and recrystallized by slow addition of methanol to solution of the dye in small amount of dichloromethane. Compound 7c (33 mg, 48% yield) was obtained as a dark violet powder. Mp. 185-187° C. $^1$H NMR (500 MHz, CDCl$_3$) δ 7.64-7.48 (AA'BB', 4H, benzene: 2-H and 6-H), 6.95-6.87 (AA'BB', 4H, benzene: 3-H and 5-H), 6.84 (d, J=4.0 Hz, 2H, pyrrole: 3-H), 6.77 (d, J=3.9 Hz, 2H, pyrrole: 4-H), 3.85 (s, 6H, OCH$_3$), 3.34-3.21 (m, 4H, CH$_2$(CH$_2$)$_5$CH$_3$), 1.78-1.66 (m, 4H, CH$_2$(CH$_2$)$_5$CH$_3$), 1.60-1.51 (m, 4H, CH$_2$(CH$_2$)$_5$CH$_3$), 1.48-1.39 (m, 4H, CH$_2$(CH$_2$)$_5$CH$_3$), 1.39-1.27 (m, 8H, CH$_2$(CH$_2$)$_5$CH$_3$), 0.90 (t, J=6.5 Hz, 6H, CH$_2$(CH$_2$)$_5$CH$_3$). $^{13}$C NMR (126 MHz, CDCl$_3$) δ 160.0, 158.6, 143.3, 134.3, 133.2, 122.1, 119.7, 116.0, 115.8, 115.5, 114.1, 98.3, 81.9, 55.3, 32.0, 30.7, 30.3, 29.0, 22.7, 14.2. HRMS (ESI) calcd for $C_{46}H_{48}N_2O_4$Na (M+Na$^+$): 715.3512; found: 715.3506.

3,9-Bis((4-(dimethylamino)phenyl)ethynyl)-6,12-diheptyldipyrrolo[1,2-b:1',2'-g][2,6]naphthyridine-5,11-dione (7d (A-11))

Prepared from 4-(dimethylamino)phenylacetylene (44 mg, 0.30 mmol). Product was purified using column chromatography (silica, hexanes:dichloromethane 1:1→1:3) and recrystallized by slow addition of methanol to solution of the dye in small amount of dichloromethane. Compound 7d (40 mg, 56% yield) was obtained as a black powder. Mp. 235-239° C. $^1$H NMR (500 MHz, CDCl$_3$) δ 7.57-7.46 (AA'BB', 4H, benzene: 2-H and 6-H), 6.83 (d, J=4.0 Hz, 2H, pyrrole: 3-H), 6.74 (d, J=4.0 Hz, 2H, pyrrole: 4-H), 6.73-6.59 (m, 4H, benzene: 3-H and 5-H), 3.32-3.23 (m, 4H, CH$_2$(CH$_2$)$_5$CH$_3$), 3.02 (s, 12H, NCH$_3$), 1.77-1.68 (m, 4H, CH$_2$(CH$_2$)$_5$CH$_3$), 1.59-1.52 (m, 4H, CH$_2$(CH$_2$)$_5$CH$_3$), 1.47- 1.40 (m, 4H, CH$_2$(CH$_2$)$_5$CH$_3$), 1.37-1.30 (m, 8H, CH$_2$(CH$_2$)$_5$CH$_3$), 0.90 (t, J=6.8 Hz, 6H, CH$_2$(CH$_2$)$_5$CH). $^{13}$C NMR (126 MHz, CDCl$_3$) δ 158.7, 150.2, 142.8, 134.0, 132.9, 121.5, 120.2, 115.8, 111.9, 99.9, 81.8, 40.3, 32.1, 30.7, 30.4, 29.1, 22.7, 14.2. HRMS (ESI) calcd for $C_{48}H_{55}N_4O_2$ (M+H$^+$): 719.4325; found: 719.4325. Elemental analysis calcd (%) for $C_{48}H_{54}N_4O_2$: C, 80.19, H, 7.57, N, 7.79; found: C, 80.08, H, 7.50, N, 7.72.

Example 7

Synthesis of 1,4-di(pyrrol-1-yl)butane-1,4-dione (3), Modified Procedure

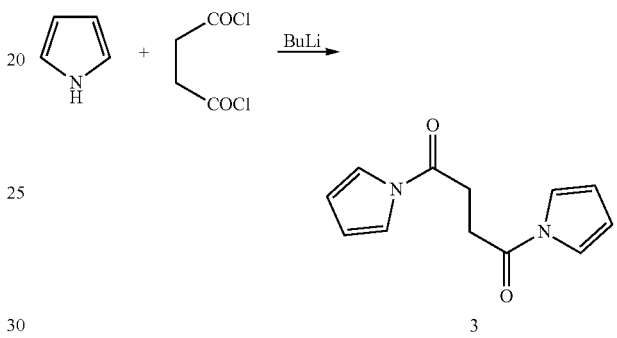

To a solution of pyrrole (0.54 mL, 7.74 mmol) in THF (20 mL) was added n-butyllithium (2.94 mL, 2.7 M in hexane, 7.94 mmol) at −40° C. After stirring for 15 min at 0° C. the solution was again cooled to −40° C. and succinylchloride (0.43 mL, 3.91 mmol) was added dropwise. The reaction mixture was stirred at room temperature for 3 h, quenched with water (10 mL) and then poured onto water (150 mL). The product precipitated as a beige powder and was used in the next step without further purification.

Synthesis of 6,12-Dinonyldipyrrolo[1,2-b:1',2'-g][2,6]naphthyridine-5,11-dione (1g (A-16))

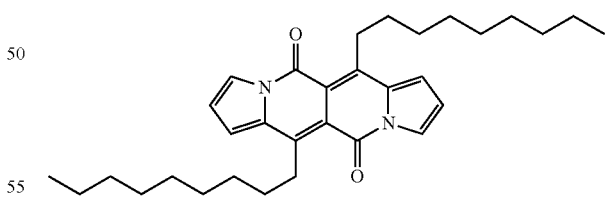

Compound 1g was made according to the general procedure given for compounds 1a-1e: compound 3 (3.00 g, 14 mmol), decanoic acid (14.34 g, 83.0 mmol), trifluoroacetic anhydride (34.97 g, 166 mmol), trifluoroacetic acid (9.49 g, 83 mmol), methylenechloride 90 ml. Reaction time: 15 h. Product was purified using column chromatography over silica gel. Compound 1g was obtained as a red solid. $^1$H NMR (300 MHz, CDCl$_3$) δ 7.84 (dd, 2H), 6.88 (dd, 2H), 6.54 (t, 2H), 3.35-3.25 (m, 4H), 1.71-1.61 (m, 4H), 1.58-1.45 (m, 4H), 1.42-1.12 (m, 20H), 0.93-0.80 (t, 6H).

Example 8

Synthesis of Compound (1h (A-17))

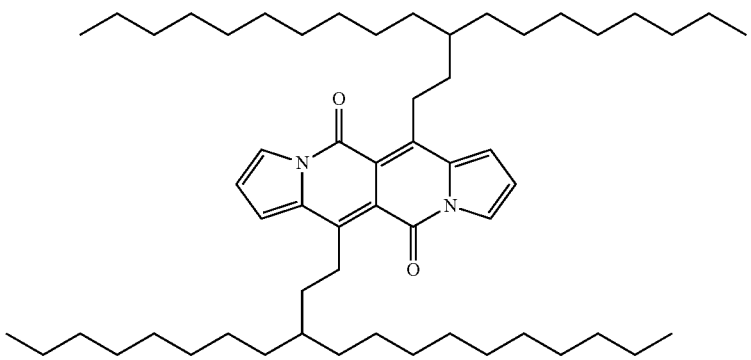 [SMILES: CCCCCCCCCCC(CCCCCCCC)CCc1c2c(=O)n3cccc3c(CCC(CCCCCCCC)CCCCCCCCCC)c2c(=O)n2cccc12]

Compound 1h was made according to the general procedure given for compounds 1a-1e from compound 3, 4-octyl-tetradecanoic acid [1448593-51-8], trifluoroacetic anhydride, trifluoroacetic acid. Reaction time: 15 h. Product was purified using column chromatography over silica gel.

Example 9

Synthesis of Compound (1i (A-18))

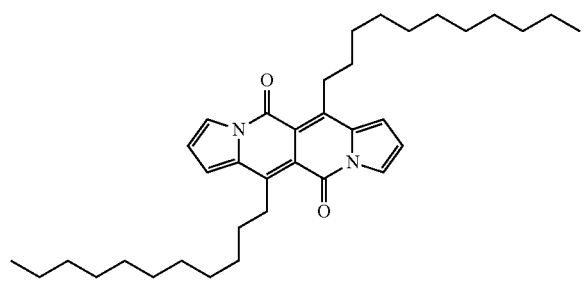 [SMILES: CCCCCCCCCCCc1c2c(=O)n3cccc3c(CCCCCCCCCCC)c2c(=O)n2cccc12]

Compound 1i was made according to the general procedure given for compounds 1a-1e from compound 3, dodecanoic acid, trifluoroacetic anhydride, trifluoroacetic acid. Reaction time: 15 h. Product was purified using column chromatography over silica gel.

Example 10

Synthesis of Compound (5a (C-6))

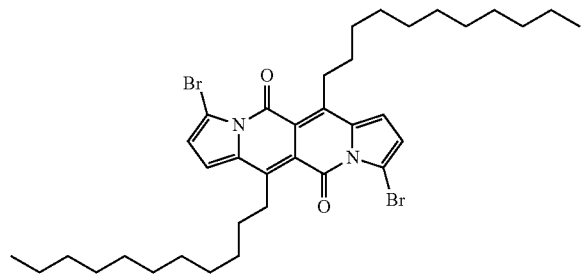 [SMILES: CCCCCCCCCCCc1c2c(=O)n3c(Br)ccc3c(CCCCCCCCCCC)c2c(=O)n2c(Br)ccc12]

Compound 5a was made according to the general procedure given for compounds 5 from compound 1i, and NBS. Product was purified using column chromatography over silica gel.

Example 11

General Procedure for the Synthesis of Compounds 8a and 8b

In a Schlenck flask containing a magnetic stirring bar were placed: compound 5a (C-6) (0.1 mmol, 72.6 mg, 1.0 eq), palladium(II) acetate (2.2 mg, 0.01 mmol, 10 mol %), tri(o-tolyl)phosphine (6.1 mg, 0.02 mmol, 20 mol %). The vessel was evacuated and backfilled with argon (3 times) and anhydrous, degassed DMF was added (6 ml) followed by argonated (i-Pr)$_2$NEt (Hünig's base) (0.1 mL) and styrene (0.4 mmol, 4.0 eq). The vessel was tightly closed and again carefully evacuated and backfilled with argon (3 times). The content of the flask was stirred at 90° C. for 24 h. All volatiles were evaporated and the product was purified as described below.

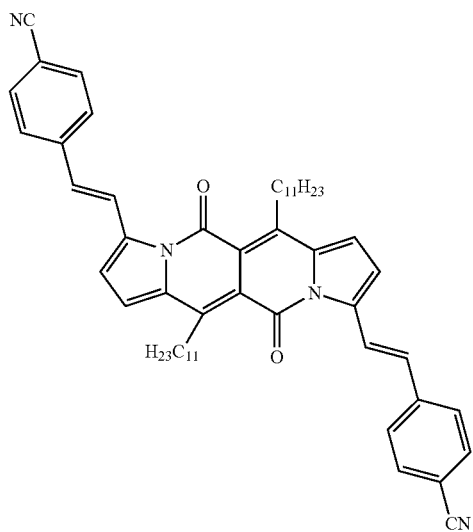

3,9-Bis((E)-4-cyanostyryl)-6,12-diundecyl-5H,11H-dipyrrolo[1,2-b:1',2'-g][2,6]naphthyridine-5,11-dione (8a (A-19))

Prepared from 4-cynanostyrene (51.7 mg, 0.4 mmol). Product was purified using column chromatography (SiO$_2$, cyclohexane:dichloromethane 1:1 then 1:2) and recrystallized by slow addition of methanol to hot solution of the dye in small amount of chloroform. Compound 8a (44.7 mg, 56% yield) was obtained as a dark brown crystals. $^1$H NMR (500 MHz, CDCl$_3$) δ 8.50 (d, 2H, J=13.2 Hz), 7.63 (m, 8H), 7.06 (d, 2H, J=16.4 Hz), 6.95 (d, 2H, J=4.0 Hz), 6.91 (d, 2H, J=4.1 Hz), 3.25 (t, 4H, J=7.7 Hz), 1.69 (m, 4H), 1.56 (m, 4H+H$_2$O in CDCl$_3$), 1.41 (m, 4H,) 1.30 (m, 24H+solvents residues), 0.88 (t, 6H, J=6.5 Hz). $^{13}$C NMR (125 MHz, CDCl$_3$) δ 160.7, 143.3, 141.7, 138.9, 135.5, 132.5, 128.9, 127.1, 123.4, 119.0, 116.7, 115.8, 114.9, 110.7, 31.9, 30.7, 30.5, 30.3, 29.7, 29.7, 29.5, 29.4, 22.7, 14.1. HRMS (EI) calcd for C$_{54}$H$_{62}$N$_4$O$_2$ 798.4873 [M$^{1+}$], found 798.4851.

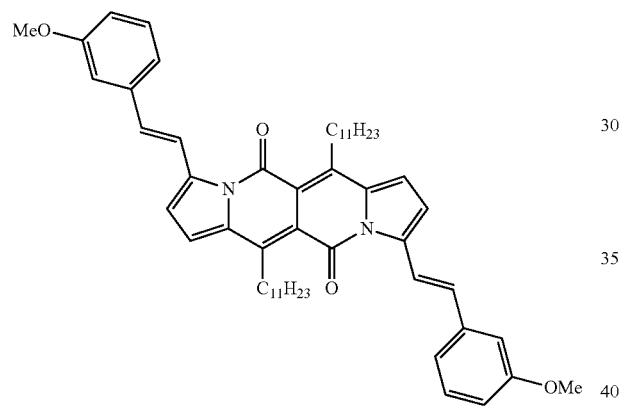

3,9-Bis((E)-3-methoxystyryl)-6,12-diundecyl-5H,11H-dipyrrolo[1,2-b:1',2'-g][2,6]naphthyridine-5,11-dione (8b (A-20))

Prepared from 3-methoxystyrene (53.7 mg, 0.4 mmol, 55.5 μL). Product was purified using column chromatography (SiO$_2$, cyclohexane:dichloromethane 3:2). The obtained fraction was washed with methanol until the washings were colorless to give sufficiently pure compound. Compound 8b (41.3 mg, 51% yield) was obtained as a dark brown crystals.

$^1$H NMR (500 MHz, CD$_2$Cl$_2$) δ 8.35 (d, 2H, J=13.2 Hz), 7.30 (t, 2H, J=6.0 Hz), 7.17 (d, 2H, J=6.0 Hz), 7.08 (t, 4H, J=8.7 Hz), 6.92 (m, 4H), 7.08 (d, 2H, J=6.4 Hz), 3.80 (s, 6H), 3.26 (t, 4H, J=6.0 Hz), 1.70 (m, 4H), 1.55 (m, 4H), 1.40 (m, 4H,) 1.28 (m, 24H+solvents residues), 0.88 (t, 6H, J=5.6 Hz). $^{13}$C NMR (125 MHz, CD$_2$Cl$_2$) δ 171.9, 161.3, 160.5, 143.1, 140.0, 139.2, 135.4, 131.2, 130.0, 120.8, 119.7, 116.8, 115.9, 114.3, 113.9, 112.5, 55.6, 32.3, 31.0, 30.9, 30.7, 30.1, 30.1, 29.9, 29.8, 23.1, 14.3. HRMS (EI) calcd for C$_{54}$H$_{68}$N$_2$O$_4$ 808.5179 [M$^{1+}$], found 808.5165.

Example 12

General Procedure for the Direct Coupling of DPND and Bromoarenes

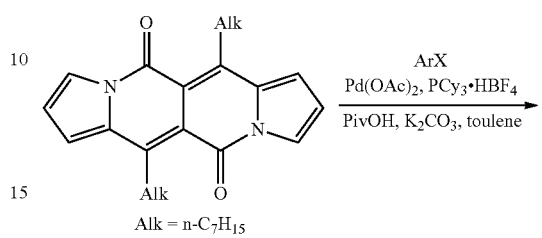

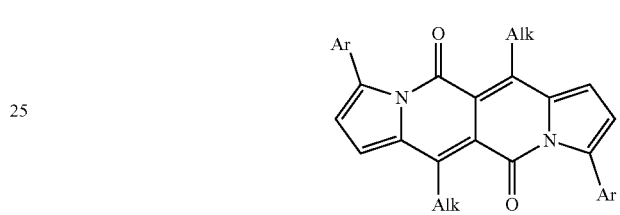

In a Schlenk flask containing a magnetic stirring bar were placed: compound 1c (A-3) (0.1 mmol, 43.3 mg, 1.0 eq), palladium(II) acetate (1.1 mg, 0.005 mmol, 5 mol %), PCy$_3$.HBF$_4$ (3.7 mg, 0.01 mmol, 10 mol %), pivalic acid (3.1 mg, 0.03 mmol, 30% mol), K$_2$CO$_3$ (55.2 mg, 0.4 mmol, 4.0 eq) and, if a solid, the bromoarene (0.25 mmol, 2.5 eq). The vessel was evacuated and backfilled with argon (3 times). If the bromoarene (0.25 mmol, 2.5 eq) was a liquid, it was added next using a syringe followed by anhydrous, degassed toluene (3 mL). The vessel was tightly closed and again carefully evacuated and backfilled with argon (3 times). The content of the flask was stirred at 120° C. for typically 24-72 h. After indicated time the flask was cooled down to room temperature and extracted three times with dichloromethane (3×25 mL), then dried over magnesium sulphate. All solvents were evaporated off and the residue was purified by column chromatography.

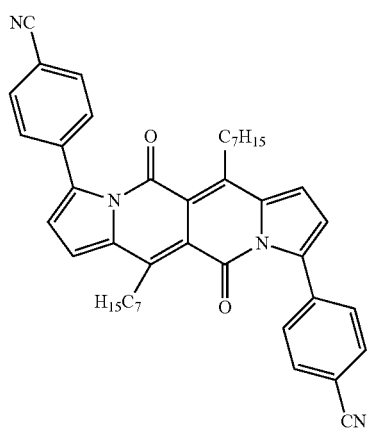

4,4'-(6,12-diheptyl-5,11-dioxo-5H,11H-dipyrrolo[1,2-b:1',2'-g][2,6]naphthyridine-3,9-diyl)dibenzonitrile (9a (A-21))

Prepared using 4-bromocyanobenzene (45.5 mg, 0.25 mmol). Product was purified using column chromatography (SiO$_2$, n-hexane:dichloromethane 1:3) and recrystallized by slow addition of methanol to hot solution of the dye in small amount of chloroform. Compound (47.8 mg, 64% yield) was obtained as a dark brown crystals. R$_f$=0.42 (SiO$_2$, n-hexane/DCM, 1:3). $^1$H NMR (500 MHz, CDCl$_3$) δ 7.68 (d, 4H, J=8.5 Hz), 7.56 (d, 4H, J=8.5 Hz), 6.92 (d, 2H, J=3.5 Hz), 6.59 (d, 2H, J=4.0 Hz), 3.20-3.17 (m, 4H), 1.71-1.67 (m, 4H), 1.50-1.44 (m, 4H,) 1.37-1.29 (m, 12H), 0.88 (t, 6H, J=6.5 Hz). $^{13}$C NMR (125 MHz, CDCl$_3$) δ 159.4, 144.2, 137.9, 137.3, 136.0, 131.4, 129.2, 119.5, 118.9, 116.0, 115.9, 111.2, 31.8, 30.5, 30.4, 30.1, 29.1, 22.7, 14.1. HRMS (ESI) calcd for C$_{42}$H$_{43}$N$_4$O$_2$ 635.3386 [M+H$^+$], found 635.3383.

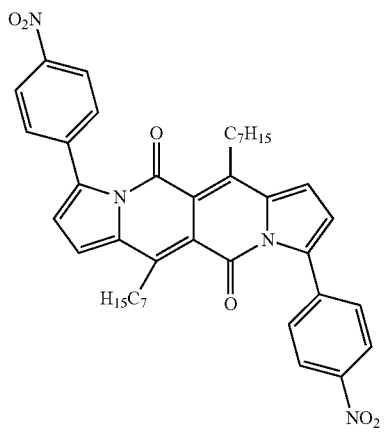

6,12-diheptyl-3,9-bis(4-nitrophenyl)-5H,11H-dipyrrolo[1,2-b:1',2'-g][2,6]naphthyridine-5,11-dione (9b (A-22))

Prepared using 4-bromonitrobenzene (43.3 mg, 0.25 mmol). Product was purified using column chromatography (SiO$_2$, cyclohexane:dichloromethane 1:1) and recrystallized from toluene. Compound (42.2 mg, 62% yield) was obtained as a dark brown crystals. R$_f$=0.30 (SiO$_2$, cyclohexane/DCM, 1:1). $^1$H NMR (500 MHz, CDCl$_3$) δ 8.26 (d, 4H, J=8.5 Hz), 7.62 (d, 4H, J=7.2 Hz), 6.94 (d, 2H, J=4.0 Hz), 6.64 (d, 2H, J=3.5 Hz), 3.22-3.20 (m, 4H), 1.68-1.62 (m, 4H), 1.50-1.44 (m, 4H,) 1.37-1.25 (m, 12H), 0.87 (t, 6H, J=6.5 Hz). $^{13}$C NMR (125 MHz, CDCl$_3$) δ 159.3, 147.0, 144.4, 139.2, 137.5, 136.2, 129.3, 123.0, 119.8, 116.1, 116.1, 31.8, 30.6, 30.4, 30.1, 29.1, 22.7, 14.1.

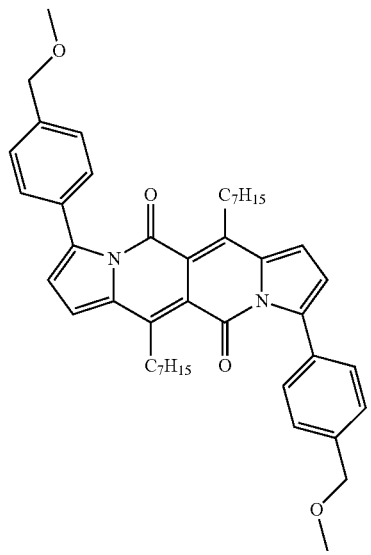

6,12-diheptyl-3,9-bis(4-(methoxymethyl)phenyl)-5H,11H-dipyrrolo[1,2-b:1',2'-g][2,6]naphthyridine-5,11-dione (9c (A-23))

Prepared from 1-bromo-4-(methoxymethyl)benzene (43.3 mg, 0.25 mmol, 36.0 µL). Product was purified using two column chromatographies (SiO$_2$, dichloromethane). Compound (14.8 mg, 22% yield) was obtained as a dark brown crystals with copper luster. R$_f$=0.32 (SiO$_2$, DCM, 1:1). $^1$H NMR (500 MHz, CDCl$_3$) δ 7.47 (d, 4H, J=8.0 Hz), 7.36 (d, 4H, J=8.0 Hz), 6.85 (d, 2H, J=3.5 Hz), 6.50 (d, 2H, J=3.5 Hz), 4.52 (s, 4H), 3.45 (s, 6H), 3.21-3.18 (m, 4H), 1.69-1.63 (m, 4H), 1.49-1.43 (m, 4H) 1.37-1.25 (m, 12H), 0.88 (t, 6H, J=6.5 Hz). $^{13}$C NMR (125 MHz, CDCl$_3$) δ 159.7, 143.3, 139.8, 137.9, 135.3, 132.3, 128.7, 126.9, 118.2, 115.8, 115.5, 74.5, 58.3, 31.8, 30.5, 30.2, 29.7, 29.2, 22.7, 14.1. HRMS (ESI) calcd for C$_{44}$H$_{53}$N$_2$O$_4$ 673.4005 [M+H$^+$], found 673.3992.

Example 13

Synthesis of Polymer (P-9)

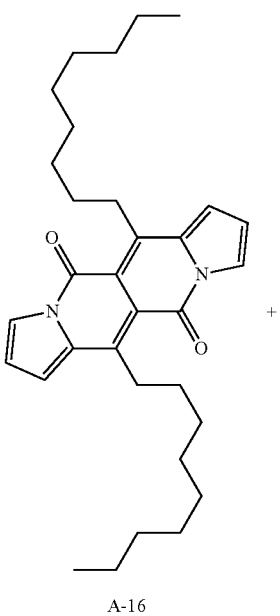

A-16

-continued

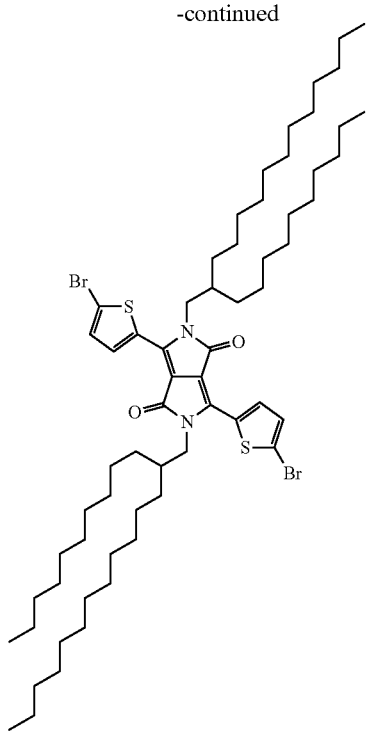

[1224430-28-7]

P-9

Compound A-16 (100.0 mg, 0.205 mmol), DPP [1224430-28-7] (231.5 mg, 0.205 mmol), pivalic acid (20.1 mg, 0.205 mmol), K$_2$CO$_3$ (113.1 mg, 0.818 mmol), Pd(OAc)$_2$ (2.3 mg, 0.01 mmol, 5 mol %) and PCy$_3$.HBF$_4$ (7.5 mg, 0.02 mol, 10 mol %) were placed in a Schlenk flask. The vessel was evacuated and backfilled with nitrogen (3 times), and anhydrous, degassed toluene was added via syringe. The Schlenk flask was closed and stirred at 120° C. for 48 h. The reaction mixture was cooled down to room temperature and poured into MeOH (150 mL). After filtration, the obtained solid was subjected to Soxhlet extraction (successively with heptane and toluene). Removing the solvent from the toluene fraction gave a bluish polymer. HT-GPC of the crude polymer: M$_n$=29,446 Da; M$_w$=77,720 Da; PD=2.64. The UV-Vis spectra of the polymer was recorded in toluene, which showed a strong absorption in the NIR with $\lambda_{max}$ at 866 nm.

Example 14

Synthesis of Polymer (P-10)

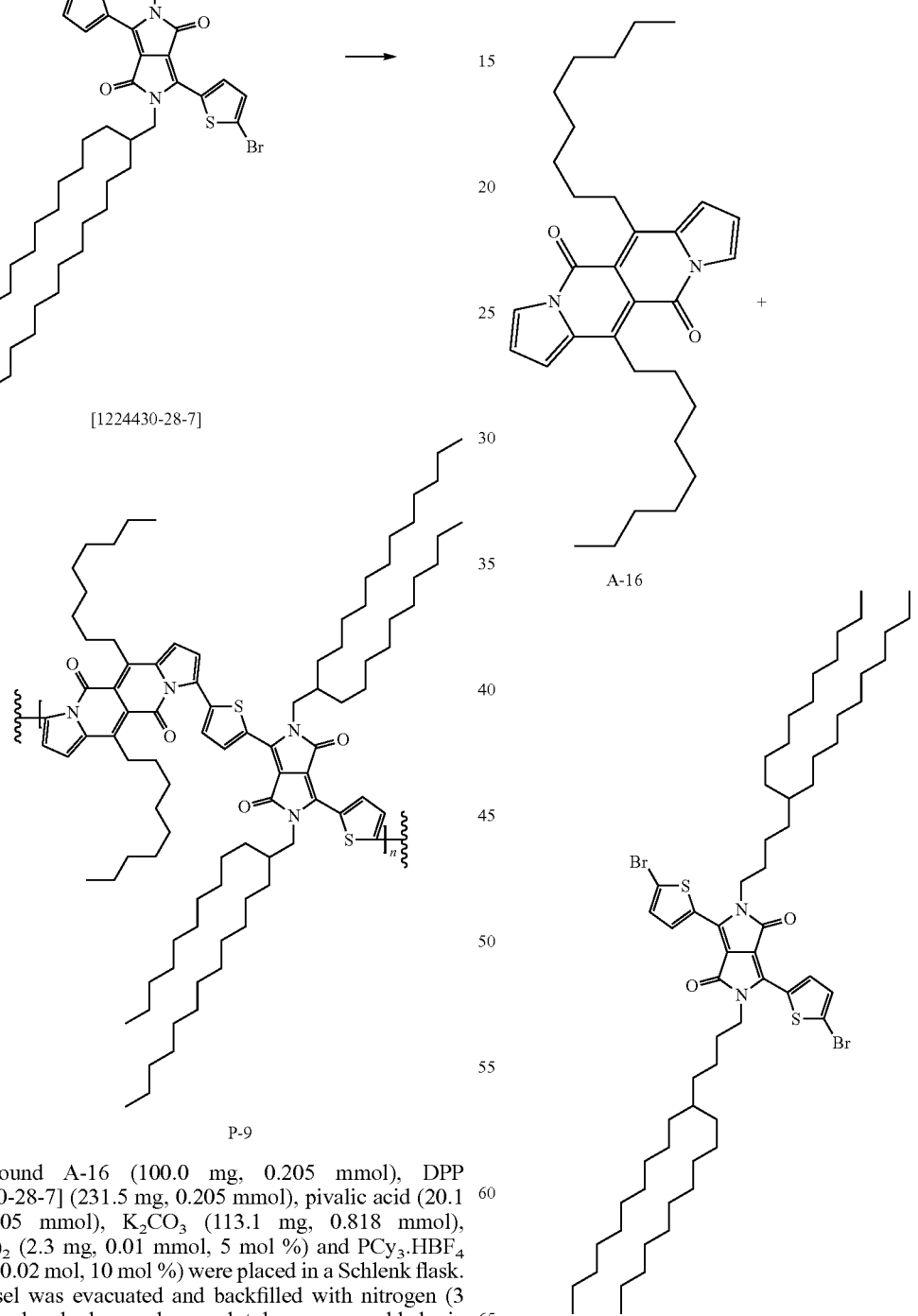

A-16

[1801150-23-1]

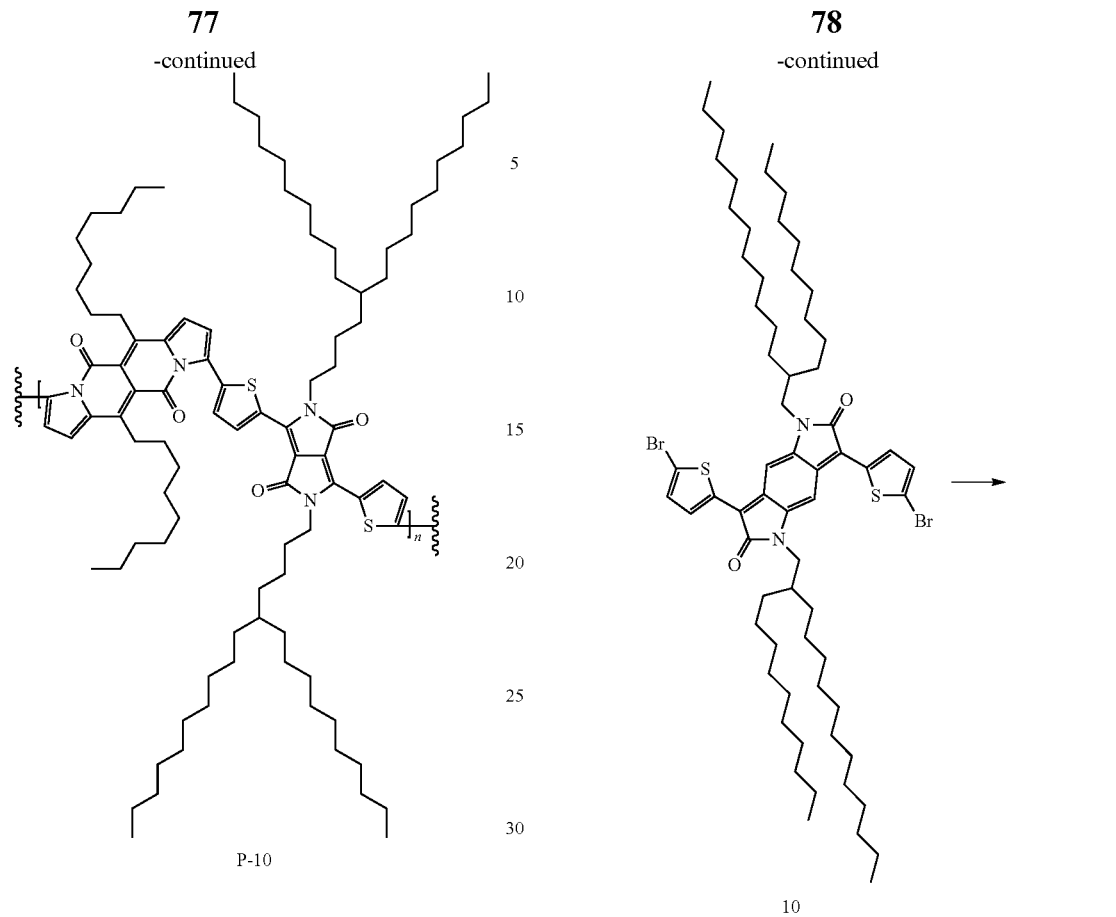
P-10
Polymer P10 was made according to the procedure given for polymer P9 from compound A-16 and DPP [1801150-23-1]. $M_n$=19,717 Da; $M_w$=58,259 Da; PD=2.96.
Example 15
Synthesis of Polymer (P-11)
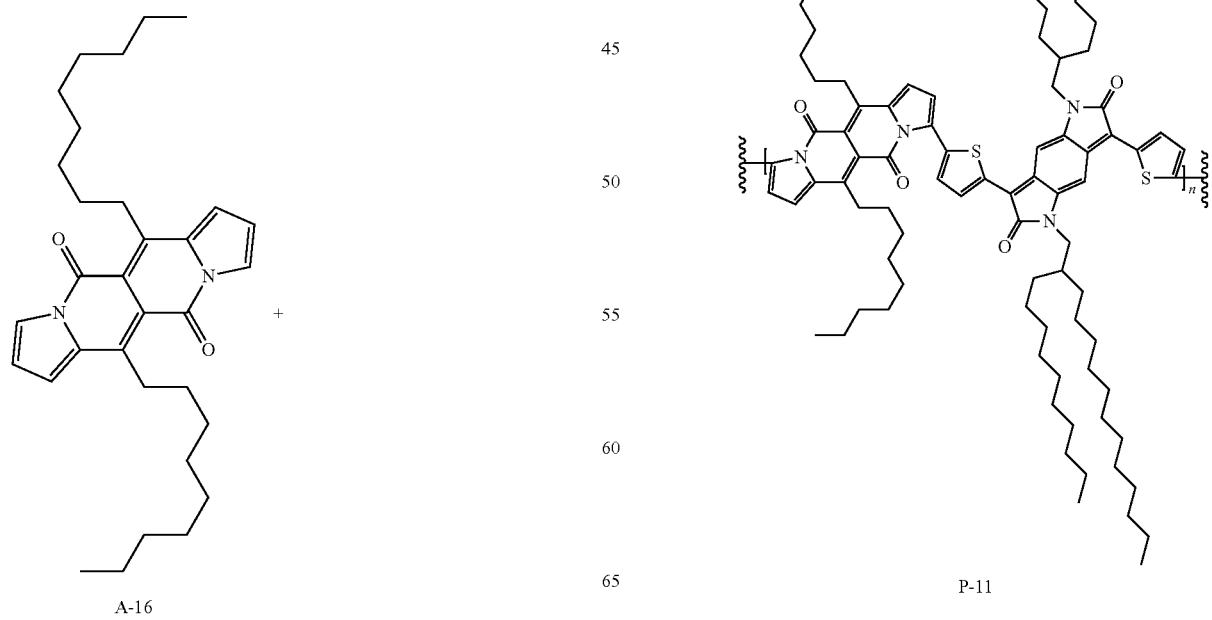
A-16
P-11

Polymer P11 was made according to the procedure given for polymer P9 from compound A-16 and compound 10. Mn=7,265 Da; $M_w$=15,068 Da; PD=2.07.

Example 16

Synthesis of Polymer (P-12)

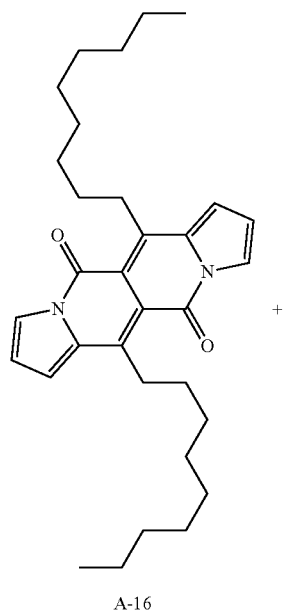

A-16

+

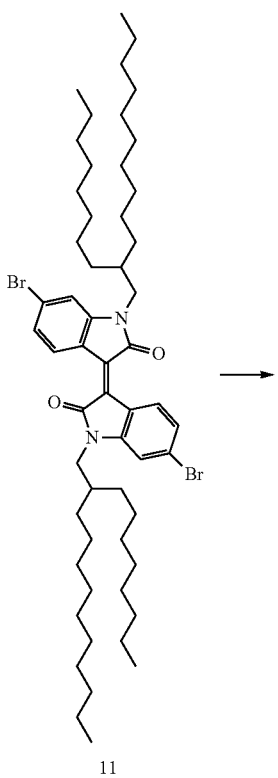

11

-continued

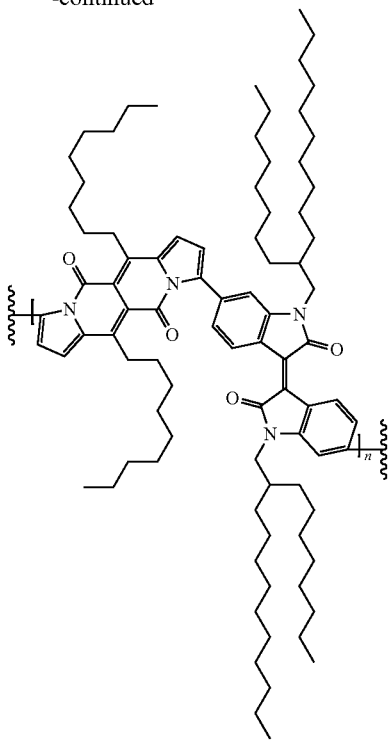

P-12

Polymer P12 was made according to the procedure given for polymer P9 from compound A-16 and compound 11. $M_n$=8,577 Da; $M_w$=21,864 Da; PD=2.55.

Application Example A1

Fabrication and Electrical Characterization of an Organic Field-Effect Transistor (OFET) Based on Polymer P9

Preparation of Back-Contact, Top-Gate FETs

The compound is dissolved at a concentration of 0.75 wt % in chlorobenzene and subsequently spincoated (1200 rpm, 15 s) onto a PET-substrate with lithographically prepatterned gold contacts, serving as Source and Drain contact of the FET. After the coating is completed, the respective substrate is immediately transferred onto a preheated hotplate and heated for 30 s at 90° C. Next the gate dielectric layer consisting of Cytop CTL-809 M is spincoated on top of the organic semiconductor (1200 rpm, 30 s). After pincoating, the substrate is again transferred to the hotplate and annealed for another 30 Min at 90° C. The thickness of the dielectric layer is 620 nm measured by profilometer. Finally 70 nm thick shadow-mask patterned silver gate electrodes are deposited by vacuum evaporation to complete FETs in the BCTG-configuration.

Electrical Characterization

The mobility μ is calculated from the root representation of the transfer characteristic curve (solid grey curve) in the saturation region. The slope m is determined from the dashed black line in the FIGURE. The dashed black line in the FIGURE is fitted to a region of the square root representation of the Drain current ID such that a good correlation to the linear slope of the root representation is obtained.

The threshold voltage $U_{Th}$ can be taken from the intersection of black dashed line in the FIGURE with the X-axis portion ($V_{GS}$).

In order to calculate the electrical properties of the OFET, the following equations are employed:

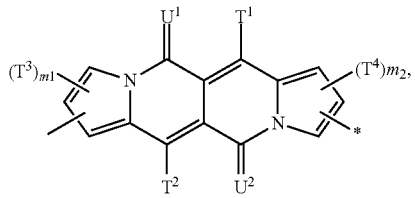

where $\varepsilon_0$ is the vacuum permittivity of $8.85 \times 10^{-12}$ As/Vm. $\varepsilon_r = 2.1$ for Cytop and d is the thickness of the dielectric. The width over length ratio W/L is 25.

The following mobilities, threshold voltage and ON/OFF Ratio have been calculated for the respective polymer from an average of 27 TFTs:

| Compound | Field-effect mobility $\mu$ [cm$^2$/Vs] | Threshold voltage $U_{TH}$ [V] | ON/OFF ratio |
|---|---|---|---|
| P9 | 0.013 | −7.5 | 2E4 |

The invention claimed is:
1. A compound of formula

$$R^{10}\text{—}Ar\text{—}Y\text{—}Ar'\text{—}R^{10'} \qquad (I),$$

wherein
Ar is a group of formula —[Ar$^3$]$_c$—[Ar$^2$]$_b$—[Ar$^1$]$_a$—**,
Ar' is a group of formula **—[Ar$^{1'}$]$_{a'}$—[Ar$^{2'}$]$_{b'}$—[Ar$^{3'}$]$_{c'}$—,
Y is a group of formula

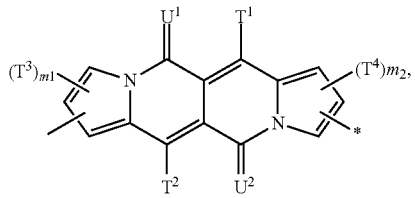

wherein
** indicates the bonding to Y,
a is 0, 1, 2, or 3;
a' is 0, 1, 2, or 3;
b is 0, 1, 2, or 3;
b' is 0, 1, 2, or 3;
c is 0, 1, 2, or 3;
c' is 0, 1, 2, or 3;
m1 is 0, 1, or 2;
m2 is 0, 1, or 2;
U$^1$ is O, or S;
U$^2$ is O, or S;
T$^1$, T$^2$, T$^3$ and T$^4$ are independently of each other:
  a hydrogen, halogen, cyano, —COOR$^{103}$, —OCOR$^{103}$, —NR$^{112}$COR$^{103}$, —CONR$^{112}$R$^{113}$, —OR$^{103'}$, —SR$^{103'}$, —SOR$^{103'}$, —SO$_2$R$^{103'}$, —NR$^{112}$SO$_2$R$^{103'}$, —NR$^{112}$R$^{113}$, —NO$_2$, C$_7$-C$_{25}$arylalkyl, which can be substituted one to three times with C$_1$-C$_8$alkyl and/or C$_1$-C$_8$alkoxy;
  a C$_1$-C$_{100}$alkyl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, C$_2$-C$_{20}$heteroaryl, or E$_{Si}$; and/or can optionally be interrupted by —O—, —S—, —NR$^{60}$—, CONR$^{60}$—, NR$^{60}$CO—, —COO—, —CO— or —OCO—,
  a C$_2$-C$_{100}$alkenyl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, C$_2$-C$_{20}$heteroaryl, or E$_{Si}$; and/or can optionally be interrupted by —O—, —S—, —NR$^{60}$—, CONR$^{60}$—, NR$^{60}$CO—, —COO—, —CO— or —OCO—,
  a C$_2$-C$_{100}$alkinyl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, C$_2$-C$_{20}$heteroaryl, or E$_{Si}$; and/or can optionally be interrupted by —O—, —S—, —NR$^{60}$—, CONR$^{60}$—, NR$^{60}$CO—, —COO—, —CO— or —OCO—,
  a C$_3$-C$_{12}$cycloalkyl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, C$_2$-C$_{20}$heteroaryl, or E$_{Si}$; and/or can optionally be interrupted by —O—, —S—, —NR$^{60}$—, CONR$^{60}$—, NR$^{60}$CO—, —COO—, —CO— or —OCO—,
  a C$_6$-C$_{24}$aryl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, C$_2$-C$_{20}$heteroaryl, or E$_{Si}$;
  a C$_2$-C$_{20}$heteroaryl group which can optionally be substituted one or more times with C$_1$-C$_{12}$alkyl, C$_1$-C$_{12}$alkoxy, halogen, C$_5$-C$_{12}$cycloalkyl, nitro, cyano, vinyl, allyl, C$_6$-C$_{24}$aryl, C$_2$-C$_{20}$heteroaryl, or E$_{Si}$;
  a —CO—C$_1$-C$_{18}$alkyl group, a —CO—C$_5$-C$_{12}$cycloalkyl group, or —COO—C$_1$-C$_{18}$alkyl group;
Ar$^1$ and Ar$^{1'}$ are independently of each other

(XIa)

(XIb)

(XIc)

(XId)

(XIe)

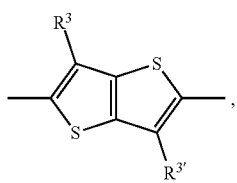
(XIf)
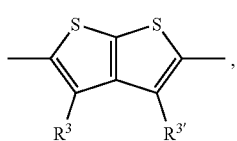
(XIg)
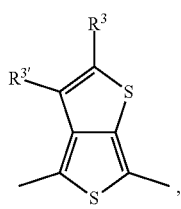
(XIh)
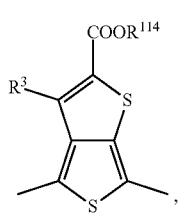
(XIi)
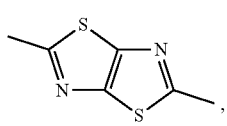
(XIj)
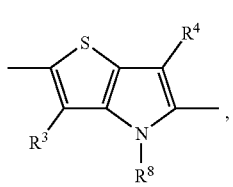
(XIk)
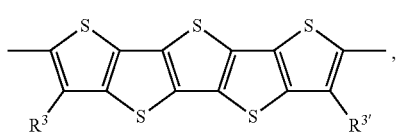
(XIl)
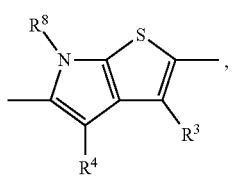
(XIm)
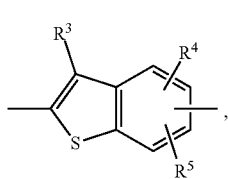
(XIn)
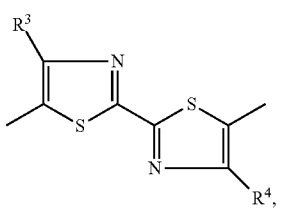
(XIo)
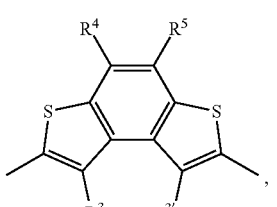
(XIp)
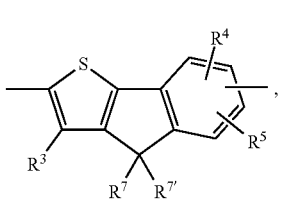
(XIq)
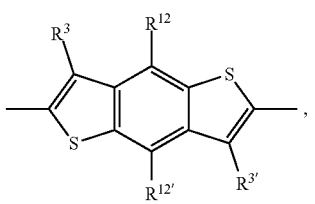
(XIr)
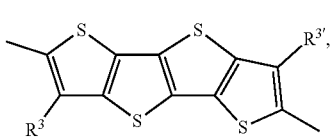
(XIs)
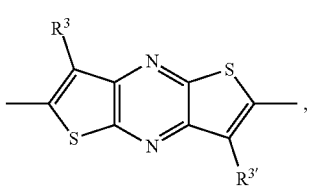
(XIt)
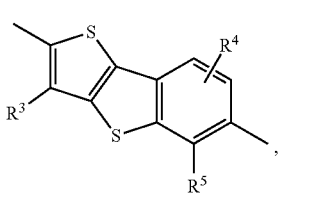
(XIu)
(XIv)
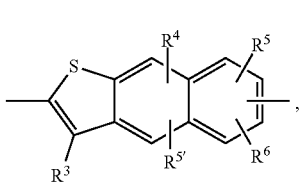
(XIw)

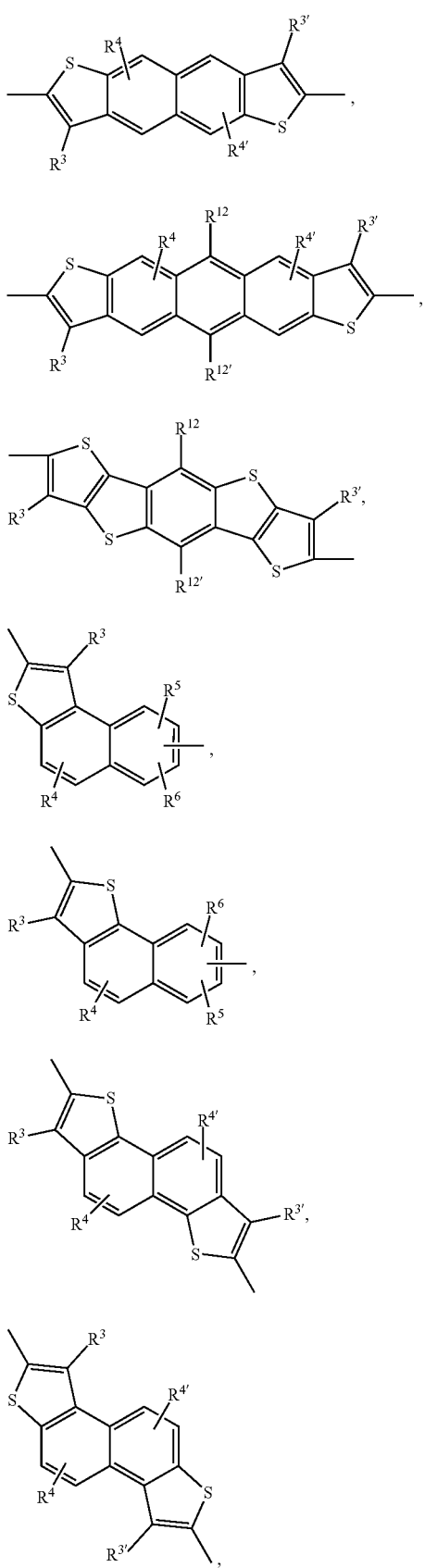
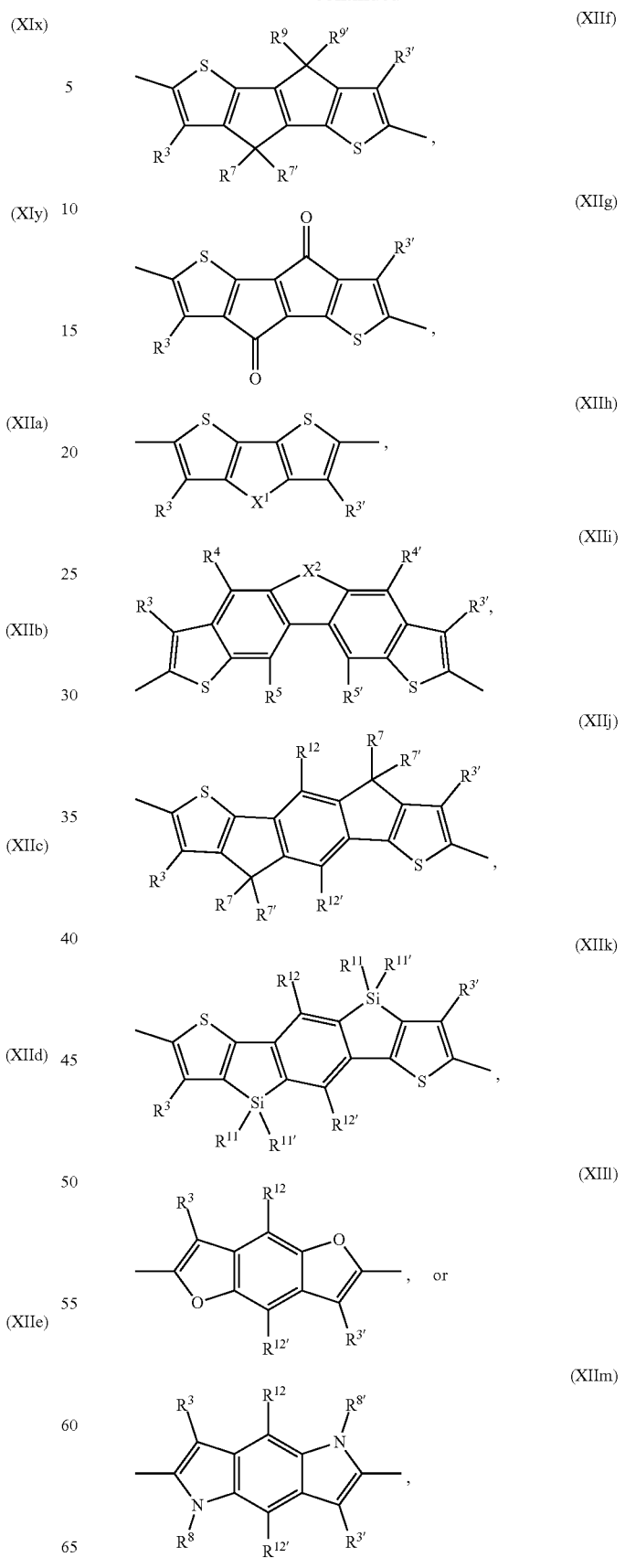

Ar², Ar²′, Ar³ and Ar³′ have independently of each other the meaning of Ar¹, or are independently of each other (XIIIa)
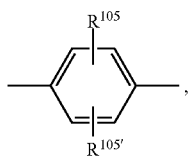, (XIIIb)
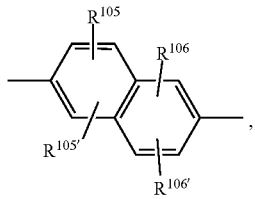, (XIIIc)
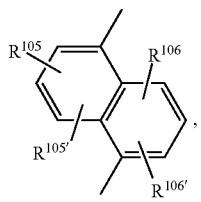, (XIIId)
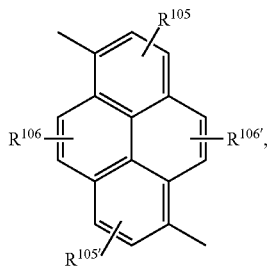

(XIIIe)
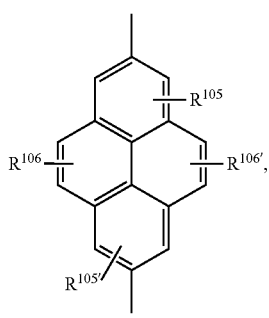

(XIIIf)
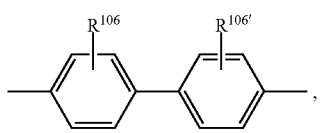, (XIIIg)
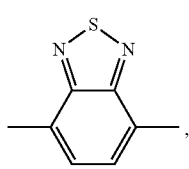,

-continued (XIIIh)
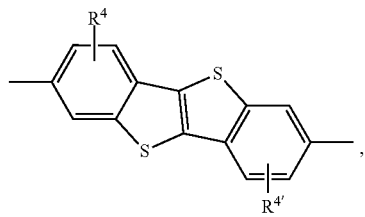, (XIIIi)
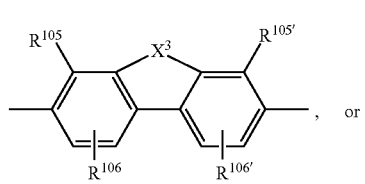, or (XIIIj)
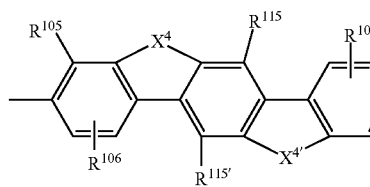, wherein
X is O, S, Se, Te, or NR⁸,
X′ is O, or S,
X¹, X² and X³ are independently of each other S, O, NR¹⁰⁷—, —Si(R¹¹⁷)(R¹¹⁷′)—, —Ge(R¹¹⁷)(R¹¹⁷′)—, —C(R¹⁰⁸)(R¹⁰⁹)—, —C(=O)—, —C(=CR¹¹⁰R¹¹¹)—,

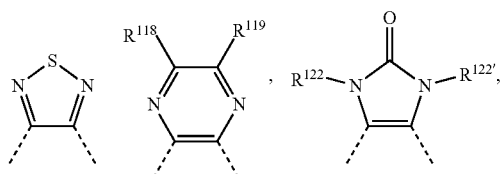

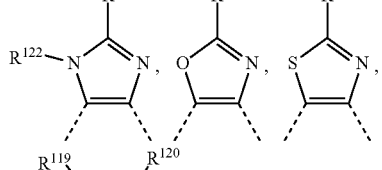

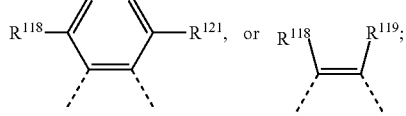

X⁴ and X⁴′ are independently of each other S, O, NR¹⁰⁷—, —Si(R¹¹⁷)(R¹¹⁷′)—, —Ge(R¹¹⁷)(R¹¹⁷′)—, —C(R¹⁰⁸)(R¹⁰⁹)—, —C(=O)—, —C(=CR¹¹⁰R¹¹¹)—,
R³ and R³′ are independently of each other hydrogen, halogen, halogenated $C_1$-$C_{25}$alkyl, cyano, $C_1$-$C_{25}$alkyl, which may optionally be interrupted by one or more oxygen or sulphur atoms, $C_7$-$C_{25}$arylalkyl, or $C_1$-$C_{25}$alkoxy;
R⁴, R⁴′, R⁵, R⁵′, R⁶, and R⁶′ are independently of each other hydrogen, halogen, halogenated C$_1$-C$_{25}$alkyl, cyano, C$_1$-C$_{25}$alkyl, which may optionally be interrupted by one or more oxygen or sulphur atoms, C$_7$-C$_{25}$arylalkyl, or C$_1$-C$_{25}$ alkoxy;

R$^7$, R$^{7'}$, R$^9$ and R$^{9'}$ are independently of each other hydrogen, C$_1$-C$_{25}$alkyl, which may optionally be interrupted by one or more oxygen or sulphur atoms, or C$_1$-C$_{25}$arylalkyl;

R$^8$ and R$^{8'}$ are independently of each other hydrogen, C$_6$-C$_{18}$aryl, C$_6$-C$_{18}$aryl which is substituted by C$_1$-C$_{18}$alkyl or C$_1$-C$_{18}$alkoxy, or C$_1$-C$_{25}$alkyl, which may optionally be interrupted by one or more oxygen or sulphur atoms, or C$_7$-C$_{25}$ arylalkyl;

R$^{10}$ and R$^{10'}$ are independently of each other hydrogen, halogen, NO$_2$, NR$^{112}$R$^{113}$, cyano, C$_1$-C$_{25}$ alkyl, C$_1$-C$_{25}$alkyl which is substituted one or more times by E and/or interrupted one or more times by D,

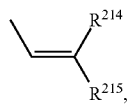

COO—C$_1$-C$_{18}$alkyl, C$_4$-C$_{18}$cycloalkyl group, C$_4$-C$_{18}$cycloalkyl group, which is substituted by G, C$_2$-C$_{18}$alkenyl, C$_2$-C$_{18}$alkynyl, C$_1$-C$_{18}$ alkylthio, C$_1$-C$_{18}$alkoxy, C$_1$-C$_{18}$alkoxy which is substituted by E and/or interrupted by D, C$_7$-C$_{25}$aralkyl, C$_7$-C$_{25}$aralkyl, which is substituted by G, or a group of formulae IVa to IVk, (IVa)
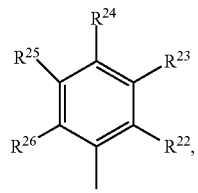

(IVb)
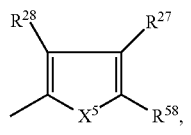

(IVc)
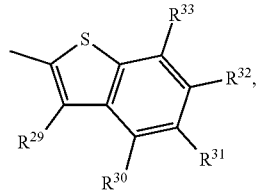

(IVd)
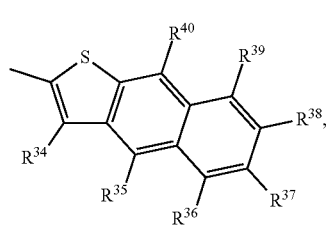

(IVe)
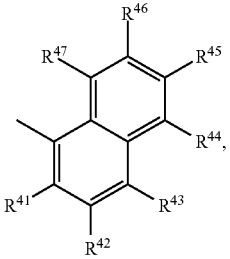

(IVf)
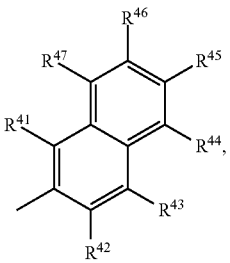

(IVg)
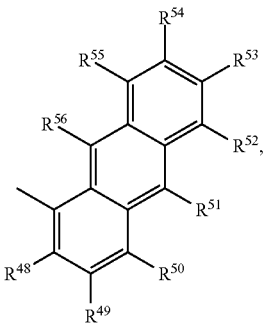

(IVh)
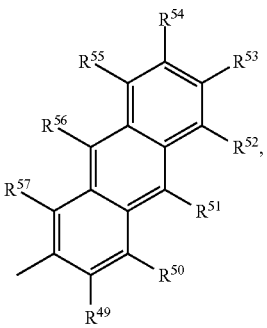

(IVi)
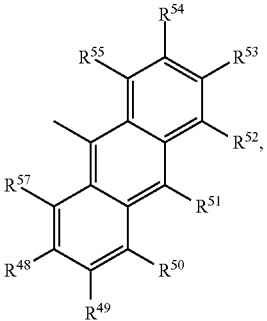

-continued

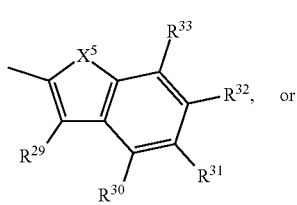
(IVj)

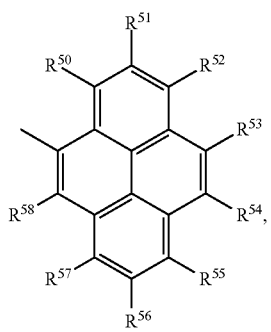
(IVk)

wherein $X^5$ is O, S, Se, Te, or $NR^{59}$, $R^{11}$ and $R^{11'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_5$alkoxy;

$R^{12}$ and $R^{12'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

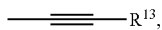—$R^{13}$, $R^{13}$ is a $C_1$-$C_8$alkyl group, or a tri($C_1$-$C_8$alkyl)silyl group; $R^{22}$ to $R^{26}$ and $R^{29}$ to $R^{58}$ represent independently of each other H, halogen, cyano, $NO_2$, $NR^{112}R^{113}$, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{25}$alkylthio, $C_1$-$C_{25}$alkoxy, $C_1$-$C_{25}$alkoxy which is substituted by E and/or interrupted by D, $C_7$-$C_{25}$aralkyl, or $C_7$-$C_{25}$aralkyl, which is substituted by G, $R^{27}$ and $R^{28}$ are independently of each other hydrogen, $C_1$-$C_{25}$alkyl, halogen, cyano or $C_7$-$C_{25}$ aralkyl, or $R^{27}$ and $R^{28}$ together represent alkylene or alkenylene which may be both bonded via oxygen and/or sulfur to the thienyl residue and which may both have up to 25 carbon atoms, $R^{59}$ is hydrogen, $C_6$-$C_{18}$aryl; $C_6$-$C_{15}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms, or $C_7$-$C_{25}$arylalkyl, $R^{60}$ is hydrogen, $C_1$-$C_{18}$haloalkyl, $C_1$-$C_{25}$alkyl, which may optionally be interrupted by one or more oxygen or sulphur atoms, $C_1$-$C_{18}$alkanoyl, or $C_7$-$C_{25}$arylalkyl, $R^{103}$ and $R^{103'}$ are independently of each other hydrogen, $C_1$-$C_{100}$alkyl, $C_1$-$C_{25}$alkyl substituted by E and/or interrupted with D, $C_2$-$C_{25}$alkenyl, $C_2$-$C_{25}$alkenyl substituted by E and/or interrupted with D, $C_7$-$C_{25}$arylalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^{104}$ and $R^{104'}$ are independently of each other hydrogen, CN, $C_1$-$C_{18}$alkyl, $C_6$-$C_{10}$aryl, which may optionally be substituted by G, or $C_2$-$C_8$heteroaryl, which may optionally be substituted by G, $R^{105}$, $R^{105'}$, $R^{106}$ and $R^{106'}$ are independently of each other hydrogen, halogen, cyano, $C_1$-$C_{25}$alkyl, which may optionally be interrupted by one or more oxygen or sulphur atoms; $C_7$-$C_{25}$arylalkyl, or $C_1$-$C_{18}$alkoxy, $R^{107}$ is hydrogen, $C_7$-$C_{25}$arylalkyl, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$perfluoroalkyl; $C_1$-$C_{25}$alkyl, which may be interrupted by —O—, or —S—; or —$COOR^{103}$; $R^{103}$ is as defined above;

$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{108}$ and $R^{109}$ together form a group of formula =$CR^{110}R^{111}$, wherein $R^{110}$ and $R^{111}$ are independently of each other H, $C_1$-$C_8$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, wherein D is —CO—, —COO—, —S—, —O—, or —$NR^{112}$—, E is $C_1$-$C_8$alkylthio, $C_1$-$C_8$alkoxy, CN, —$NR^{112}R^{113}$, —$CONR^{112}R^{113}$, or halogen, G is E, or $C_1$-$C_{18}$alkyl, and $R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{114}$ is $C_1$-$C_{25}$alkyl, which may optionally be interrupted by one, or more oxygen, or sulphur atoms, $R^{115}$ and $R^{115'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or

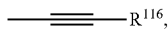—$R^{116}$, $R^{116}$ is a $C_1$-$C_8$alkyl group, or a tri($C_1$-$C_8$alkyl)silyl group;

$R^{117}$ and $R^{117'}$ are independently of each other $C_1$-$C_{25}$alkyl group, which can be substituted one to three times with $C_1$-$C_8$alkyl and/or $C_1$-$C_8$alkoxy;

$R^{118}$, $R^{119}$, $R^{120}$ and $R^{121}$ are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$aryl, $C_6$-$C_{18}$aryl which is substituted by $C_1$-$C_{18}$alkyl or $C_1$-$C_{18}$alkoxy, or $C_1$-$C_{25}$alkyl, which may optionally be interrupted by one or more oxygen or sulphur atoms, or $C_7$-$C_{25}$arylalkyl; and $E_{Si}$ is —$SiR^{161}R^{162}R^{163}$ or —O—$SiR^{161}R^{162}R^{163}$, wherein $R^{161}$, $R^{162}$ and $R^{163}$ are independently of each other hydrogen, $C_1$-$C_{25}$alkyl, $C_3$-$C_{12}$cycloalkyl which might optionally be substituted with $C_1$-$C_4$alkyl, $C_1$-$C_{25}$haloalkyl, $C_2$-$C_{25}$alkenyl, —O—$SiR^{164}R^{165}R^{166}$, —(O—$SiR^{164}R^{165})_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170})_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—Si($CH_3$)$_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$alkyl, halogen, cyano or $C_1$-$C_{25}$alkoxy;

$R^{167}$ and $R^{168}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50;

$R^{214}$ and $R^{215}$ are independently of each other hydrogen, $C_1$-$C_{18}$alkyl, $C_6$-$C_{24}$aryl, $C_2$-$C_{20}$heteroaryl, —CN or $COOR^{216}$; and $R^{216}$ is $C_1$-$C_{25}$alkyl, $C_1$-$C_{25}$haloalkyl, $C_7$-$C_{25}$ arylalkyl, $C_6$-$C_{24}$aryl or $C_2$-$C_{20}$heteroaryl.

2. The compound according to claim 1, which is a compound of formula

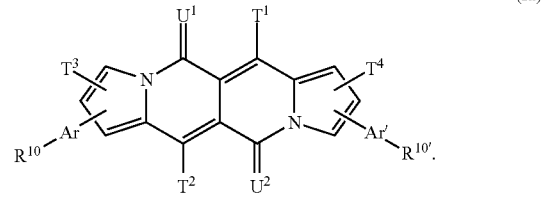

(Ia)

3. The compound according to claim 1, which is a compound of formula

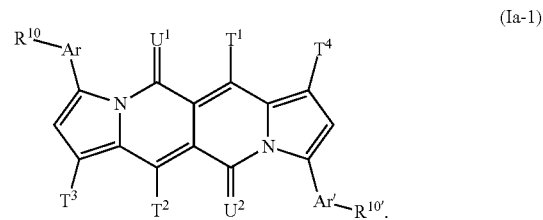

(Ia-1)

4. The compound according to claim 1, wherein $U^1$ and $U^2$ are O.

5. The compound according to claim 1, wherein $T^1$, $T^2$, $T^3$ and $T^4$ are H, a $C_1$-$C_{38}$alkyl group which can optionally be substituted one or more times with $C_1$-$C_{12}$alkoxy, halogen, $C_5$-$C_{12}$cycloalkyl, cyano, or $E_{Si}$; and/or can optionally be interrupted by —O—, —S—, or —$NR^{60}$—, wherein $R^{60}$ is $C_1$-$C_{25}$alkyl, or phenyl$C_1$-$C_4$alkyl, which can be substituted one to three times with $C_1$-$C_8$alkyl and/or $C_1$-$C_8$alkoxy, wherein $E_{Si}$ is —$SiR^{161}R^{162}R^{163}$;

$R^{161}$, $R^{162}$ and $R^{163}$ are independently of each other $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—$SiR^{164}R^{165}R^{166}$, —(O—$SiR^{64}R^{165})_d$—$R^{166}$, or phenyl;

$R^{164}$, $R^{165}$ and $R^{166}$ are independently of each other $C_1$-$C_8$alkyl, $C_1$-$C_8$haloalkyl, $C_2$-$C_8$alkenyl, —O—$SiR^{169}R^{170}R^{171}$, —(O—$SiR^{169}R^{170})_d$—$R^{171}$, or phenyl;

$R^{169}$, $R^{170}$ and $R^{171}$ are independently of each other $C_1$-$C_8$alkyl, $C_1$-$C_8$haloalkyl, $C_2$-$C_8$alkenyl, —O—Si($CH_3$)$_3$, or phenyl; and d is an integer from 1 to 10.

6. The compound according to claim 1, wherein —Ar—$R^{10}$ and —Ar'—$R^{10'}$ are independently of each other H, F, cyano, $C_1$-$C_{25}$alkyl, $C_1$-$C_{25}$alkyl substituted with one or more halogen atoms,

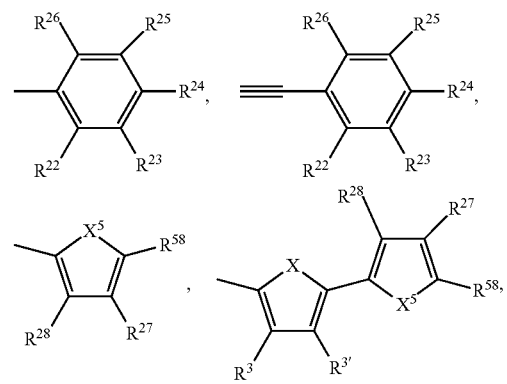

-continued

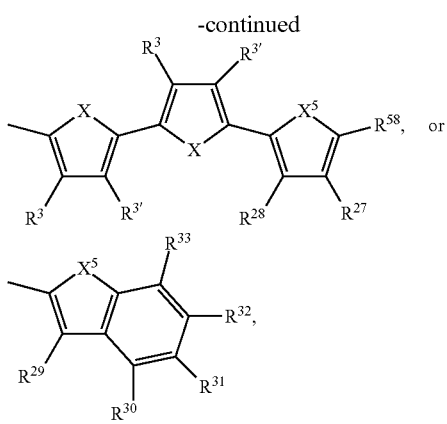

wherein
$R^3$ and $R^{3'}$ are independently of each other hydrogen, F, $C_1-C_{25}$alkyl, or $C_1-C_{25}$alkoxy,
$R^{22}$, $R^{23}$, $R^{25}$, $R^{26}$, $R^{27}$, $R^{28}$ and $R^{29}$ to $R^{33}$ represent independently of each other H, F, cyano, $C_1-C_{25}$alkoxy, $C_1-C_{25}$alkyl substituted with one or more F, or $C_1-C_{25}$alkyl, and
$R^{24}$ is H, F, cyano, $NO_2$, $NR^{112}R^{113}$, phenyl, $C_1-C_{25}$alkoxy, $C_1-C_{25}$alkylthio, $C_1-C_{25}$alkyl substituted with one or more halogen atoms, or $C_1-C_{25}$alkyl;
X is O, S, Se, or $NR^8$,
$X^5$ is O, S, Se, or $NR^{59}$,
$R^{58}$ is H, F, cyano, phenyl, $C_1-C_{25}$alkoxy, $C_1-C_{25}$alkylthio, $C_1-C_{25}$alkyl substituted with one or more halogen atoms, or $C_1-C_{25}$alkyl;
$R^8$ and $R^{59}$ are hydrogen, $C_6-C_{18}$aryl; $C_6-C_{18}$aryl which is substituted one to three times by $C_1-C_{18}$alkyl, or $C_1-C_{18}$alkoxy; $C_1-C_{25}$alkyl, which may optionally be interrupted by one or more oxygen or sulphur atoms and/or is optionally substituted by one or more F; or $C_7-C_{25}$arylalkyl, and
$R^{112}$ and $R^{113}$ are independently of each other hydrogen, $C_6-C_{18}$aryl; $C_6-C_{18}$aryl which is substituted one to three times by $C_1-C_{18}$alkyl, or $C_1-C_{18}$alkoxy; $C_1-C_{25}$alkyl, which may optionally be interrupted by one or more oxygen or sulphur atoms and/or is optionally substituted by one or more F; or $C_7-C_{25}$arylalkyl.

7. The compound according to claim 1, which is a compound of formula

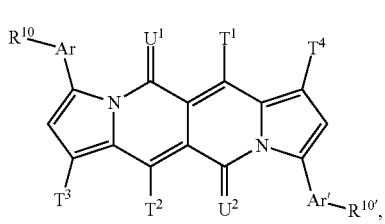

(Ia-1)

wherein
$U_1$ and $U^2$ are O,
$T^1$ and $T^2$ are H, a $C_1-C_{38}$alkyl group which can optionally be interrupted by —O—, —S—, or —$NR^1$—, wherein $R^{60}$ is $C_1-C_{25}$alkyl, or phenyl$C_1-C_4$alkyl, which can be substituted one to three times with $C_1-C_8$alkyl and/or $C_1-C_8$alkoxy,
$T^3$ and $T^4$ are H, a $C_1-C_{38}$alkyl group can optionally be interrupted by —O—, —S—, or —$NR^{60}$—, wherein $R^{60}$ is $C_1-C_{25}$alkyl, or phenyl$C_1-C_4$alkyl, which can be substituted one to three times with $C_1-C_8$alkyl and/or $C_1-C_8$alkoxy, and —Ar—$R^{10}$ and —Ar'—$R^{10'}$ are independently of each other H, F, cyano, $C_1-C_{25}$alkyl substituted with one or more fluorine atoms, $C_1-C_{25}$alkyl,

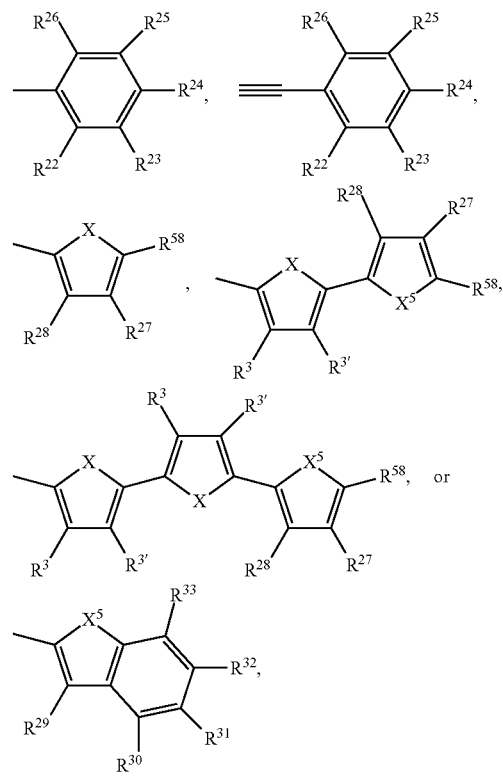

wherein
$R^3$ and $R^{3'}$ are independently of each other hydrogen, F, $C_1-C_{25}$alkyl, or $C_1-C_{25}$alkoxy,
$R^{22}$, $R^{23}$, $R^{25}$, $R^{26}$, $R^{27}$, $R^{28}$ and $R^{29}$ to $R^{33}$ represent independently of each other H, F, cyano, $C_1-C_{25}$alkoxy, $C_1-C_{25}$alkyl substituted with one or more F, or $C_1-C_{25}$alkyl, and
$R^{24}$ is H, F, cyano, $NO_2$, $NR^{112}R^{113}$, $CF_3$, phenyl, $C_1-C_{25}$alkoxy, $C_1-C_{25}$alkyl substituted with one or more halogen atoms, or $C_1-C_{25}$alkyl;
X is O, S, Se, or $NR^8$,
$X^5$ is O, S, Se, or $NR^{59}$,
$R^{58}$ is H, F, cyano, phenyl, $C_1-C_{25}$alkoxy, $C_1-C_{25}$alkylthio, $C_1-C_{25}$alkyl substituted with one or more halogen atoms, or $C_1-C_{25}$alkyl;
$R^8$ and $R^{59}$ are hydrogen, $C_6-C_{18}$aryl, $C_6-C_{18}$aryl which is substituted one to three times by $C_1-C_{18}$alkyl or $C_1-C_{18}$alkoxy, $C_1-C_{25}$alkyl, which may optionally be interrupted by one or more oxygen or sulphur atoms and/or is optionally substituted by one or more F, or $C_7-C_{25}$arylalkyl, and
$R^{112}$ and $R^{113}$ are independently of each other hydrogen, $C_6-C_{18}$aryl, $C_6-C_{18}$aryl which is substituted one to three times by $C_1-C_{18}$alkyl, or $C_1-C_{18}$alkoxy, $C_1-C_{25}$alkyl, which may optionally be interrupted by one or more oxygen or sulphur atoms and/or is optionally substituted by one or more F, or $C_7-C_{25}$arylalkyl.

8. The compound according to claim 1, which is a compound of formula

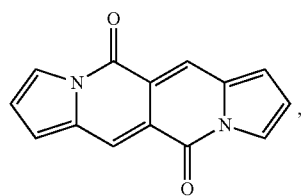 (A-1)
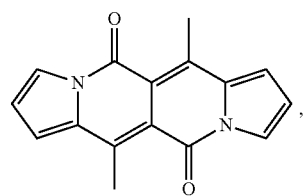 (A-2)
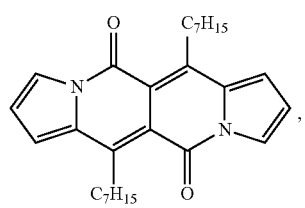 (A-3)
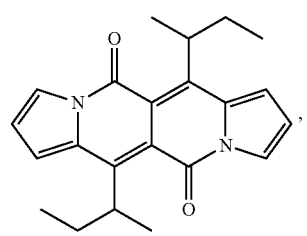 (A-4)
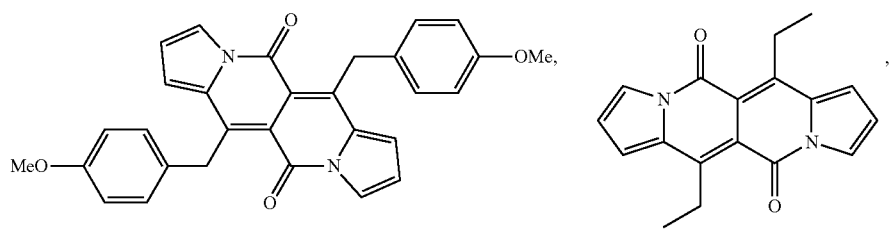 (A-5)
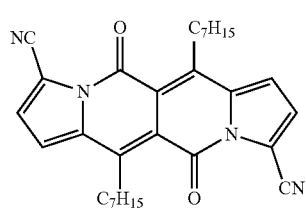 (A-6)
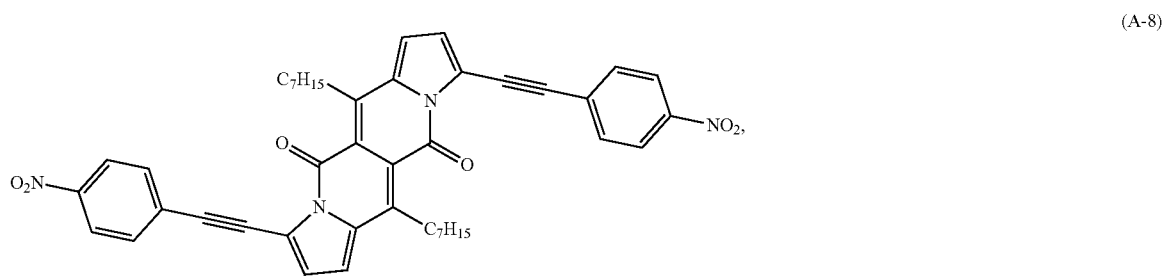 (A-7)
(A-8)
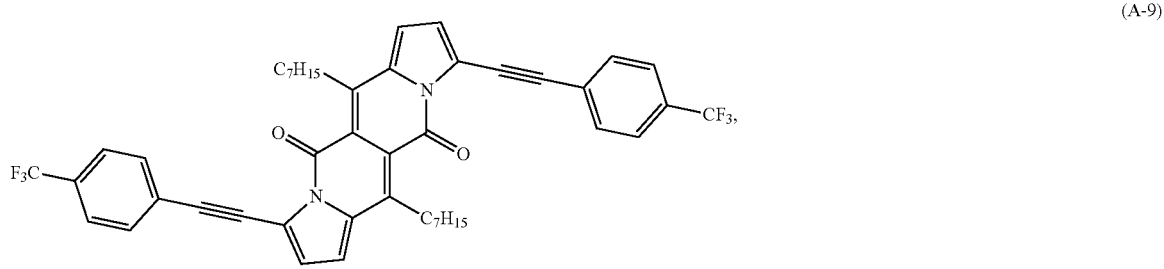 (A-9)

-continued
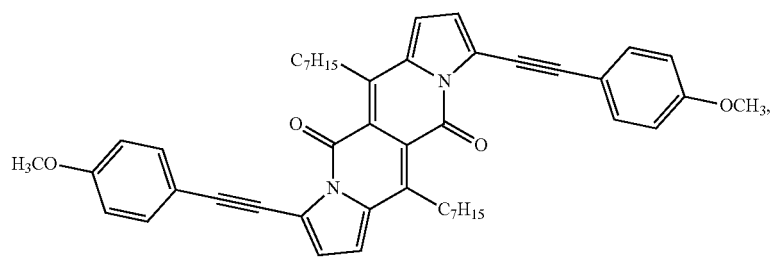
(A-10)
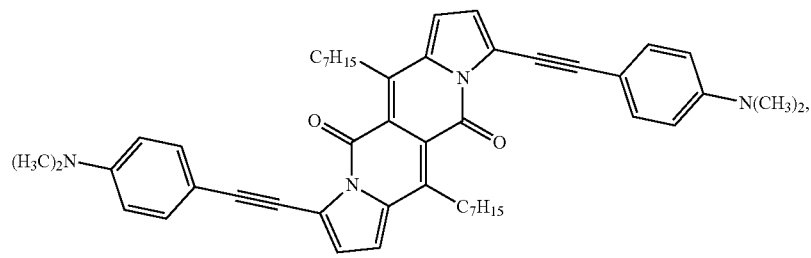
(A-11)
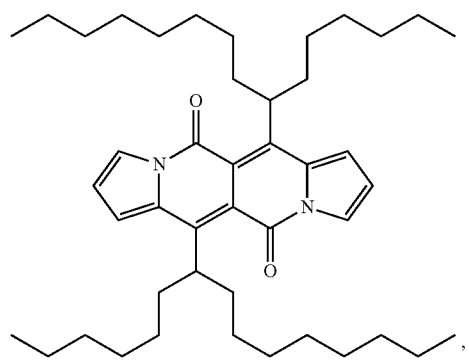
(A-12)
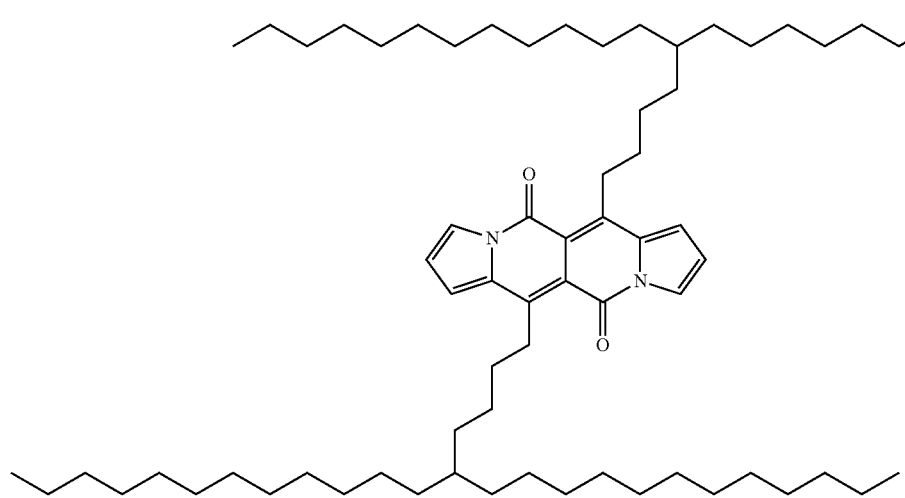
(A-13)

-continued

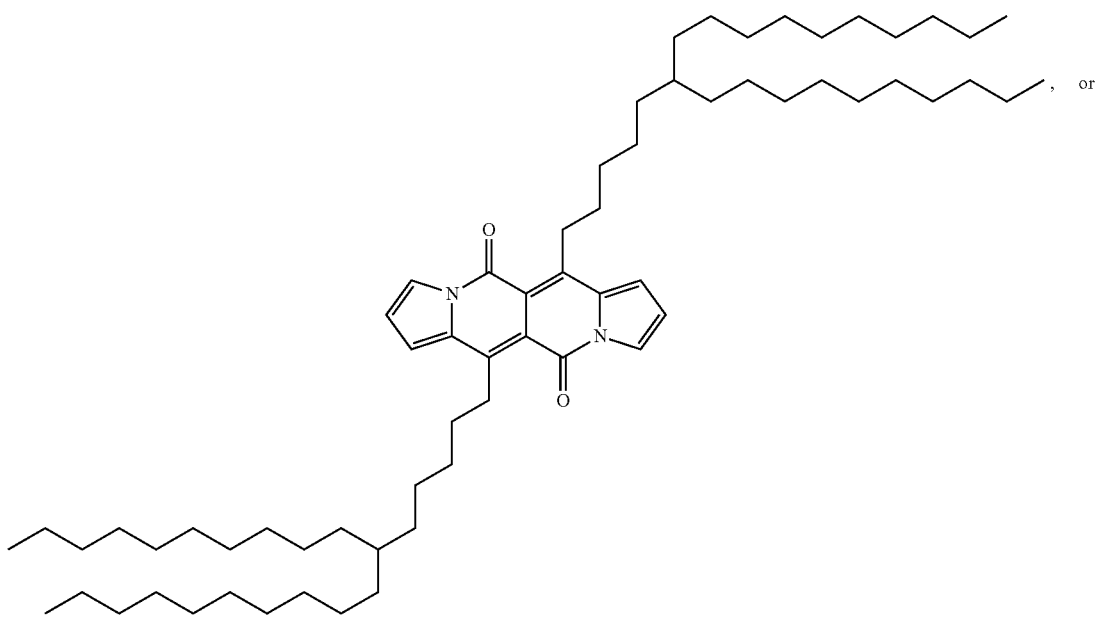

(A-14), or

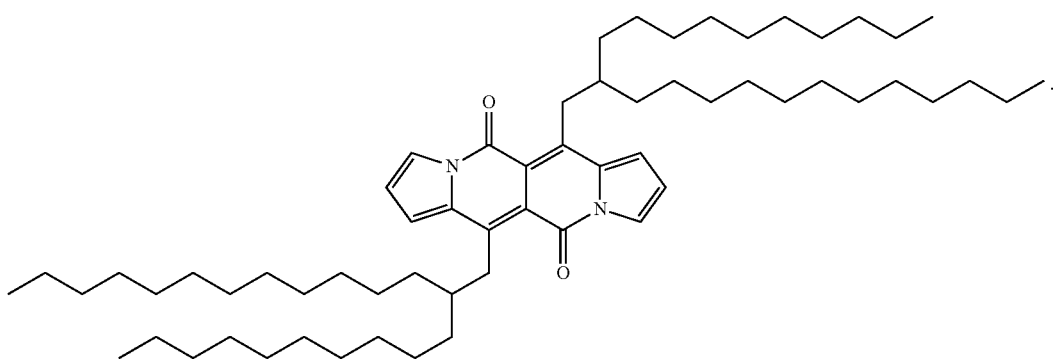

(A-15)

9. A polymer comprising a repeating unit of the formula —[(Ar)'—Y—(Ar')$_z^2$]—(V), wherein $z^1$ and $z^2$ are independently of each other 0, or 1, Y, Ar and Ar' are defined in claim 1.

10. The polymer according to claim 9, comprising a repeating unit of the formula

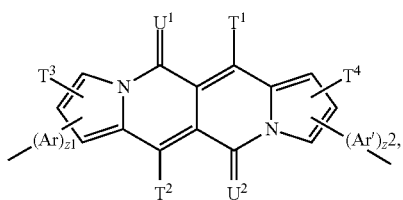

(Va)

wherein $z^1$ and $z^2$ are independently of each other 0, or 1.

11. The polymer according to claim 9, comprising a repeating unit of the formula

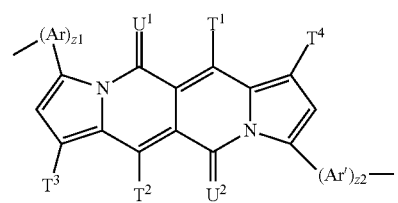

(Va-1)

12. The polymer according to claim 9, wherein $U^1$ and $U^2$ are O.

13. The polymer according to claim 9, wherein $T^1$, $T^2$, $T^3$ and $T^4$ are H, a $C_1$-$C_{38}$alkyl group which can optionally be substituted one or more times with $C_1$-$C_{12}$alkoxy, halogen, $C_5$-$C_{12}$cycloalkyl, or $E_{Si}$, and/or can optionally be interrupted by —O—, —S—, wherein $E_{Si}$ is —SiR$^{161}$R$^{162}$R$^{163}$;

R$^{161}$, R$^{162}$ and R$^{163}$ are independently of each other $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—SiR$^{164}$R$^{165}$R$^{166}$, —(O—SiR$^{164}$R$^{165}$)$_d$—R$^{166}$, or phenyl;

R¹⁶⁴, R¹⁶⁵ and R¹⁶⁶ are independently of each other C₁-C₈alkyl, C₁-C₈haloalkyl, C₂-C₈alkenyl, —O—SiR¹⁶⁹R¹⁷⁰R¹⁷¹, —(O—SiR¹⁶⁹R¹⁷⁰)_d—R¹⁷¹, or phenyl;

R¹⁶⁹, R¹⁷⁰ and R¹⁷¹ are independently of each other C₁-C₈alkyl, C₁-C₈haloalkyl, C₂-C₈alkenyl, —O—Si(CH₃)₃, or phenyl;

d is an integer from 1 to 10.

14. The polymer according to claim 9, wherein —Ar— and —Ar'— are independently of each other a single bond,

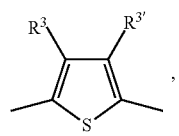 (XIa-1)

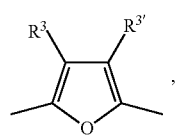 (XIa-2)

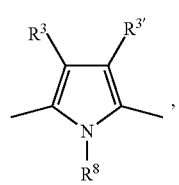 (XIa-3)

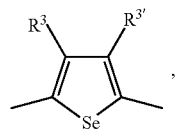 (XIa-4)

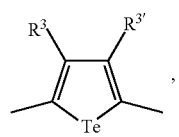 (XIa-5)

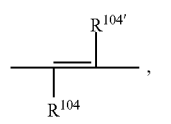 (XId)

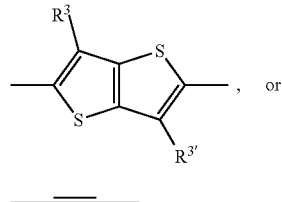 (XIf)

(XIv)

wherein
R³ and R³' are independently of each other hydrogen, F, C₁-C₂₅alkoxy, or C₁-C₂₅alkyl,
R⁸ is hydrogen, or C₁-C₂₅alkyl, and
R¹⁰⁴ and R¹⁰⁴' are independently of each other hydrogen, cyano, COOR¹⁰³, or a C₁-C₂₅alkyl group, wherein R¹⁰³ is a C₁-C₂₅alkyl group, which can optionally be interrupted by —O—, or —S—.

15. The polymer according to claim 9, comprising a repeating unit of the formula *—[A]—* and a repeating unit *—[COM¹]—*, wherein A is a repeating unit of formula (V), and
—COM¹- is a repeating unit, which has the meaning of Ar², or a group of formula

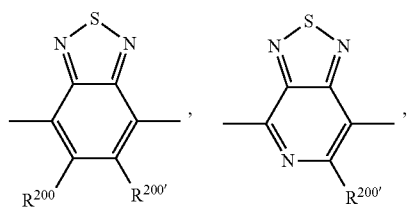

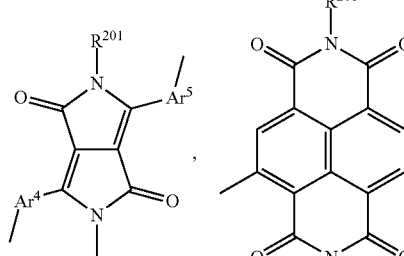

*—[Ar¹⁴]_s—[Ar¹⁵]_t—[Ar¹⁶]_u—[Ar¹⁷]_v—*, wherein
s is 1,
t is 1,
u is 0 or 1,
v is 0 or 1, and
Ar⁴ and Ar⁵ are independently of each other a group of formula

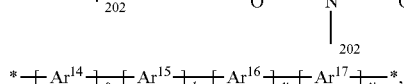

wherein
Ar¹⁴, Ar¹⁵, Ar¹⁶ and Ar¹⁷ are independently of each other a group of formula

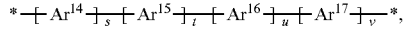

-continued

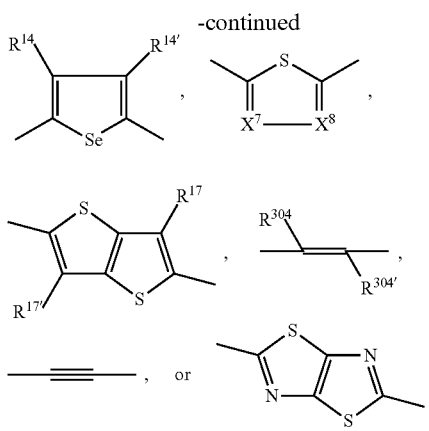

wherein
one of $X^7$ and $X^8$ is N and the other is $CR^{14}$,
$R^{14}$, $R^{14'}$, $R^{17}$ and $R^{17'}$ are independently of each other H, F, a $C_1$-$C_{52}$alkyl group, or a $C_1$-$C_{25}$alkoxy group,
$R^{200'}$ and $R^{200'}$ are independently of each other H, or F,
$R^{201}$ and $R^{202}$ are independently of each other H, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$; and/or can optionally be interrupted by —O—, —S—, —$NR^{60}$—, $CONR^{60}$—, $NR^{60}CO$—, —COO—, —CO— or —OCO—,
a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$,
a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E_{Si}$, $R^{60}$ is hydrogen, $C_1$-$C_{18}$haloalkyl, $C_1$-$C_{25}$alkyl, which may optionally be interrupted by one or more oxygen or sulphur atoms; $C_1$-$C_{18}$alkanoyl, or $C_7$-$C_{25}$arylalkyl,
$R^{206}$ is hydrogen, or $C_1$-$C_{25}$alkyl, or $C_6$-$C_{18}$aryl; $C_6$-$C_{15}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms, and
$R^{304}$ and $R^{304'}$ are independently of each other hydrogen, cyano, $COOR^{305}$, or a $C_1$-$C_{25}$alkyl group, wherein $R^{305}$ is a $C_1$-$C_{25}$alkyl group, which can optionally be interrupted by —O—, or —S—.

16. The polymer according to claim 9, which is a polymer of the formula

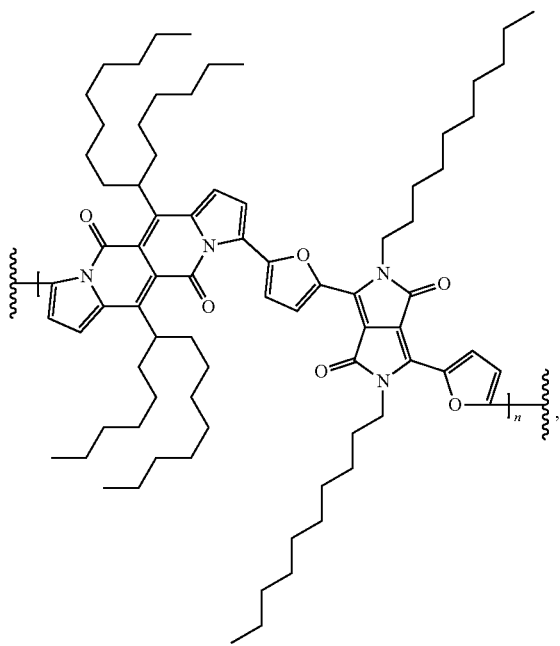

(P-1)

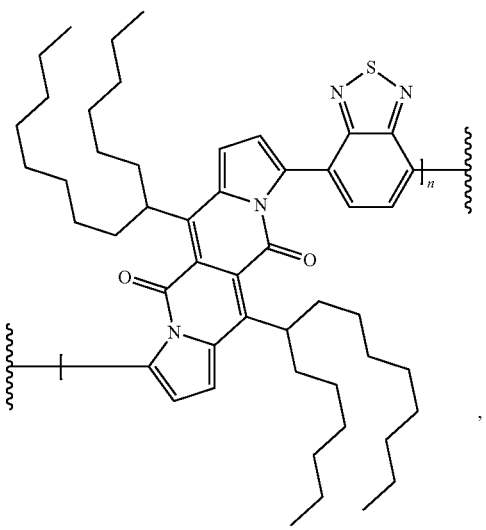

(P-2)

(P-3)
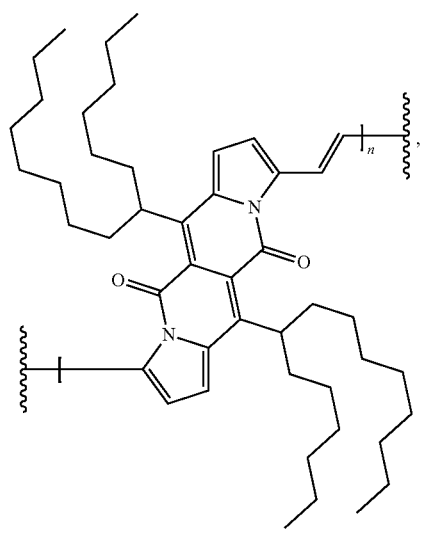
(P-4)
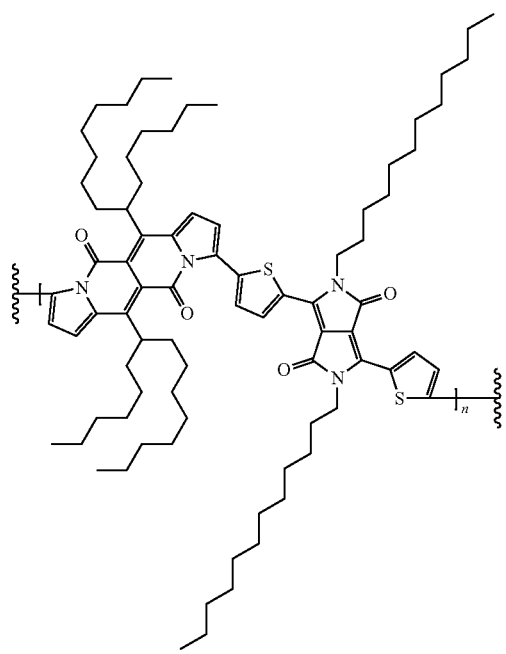
(P-5)
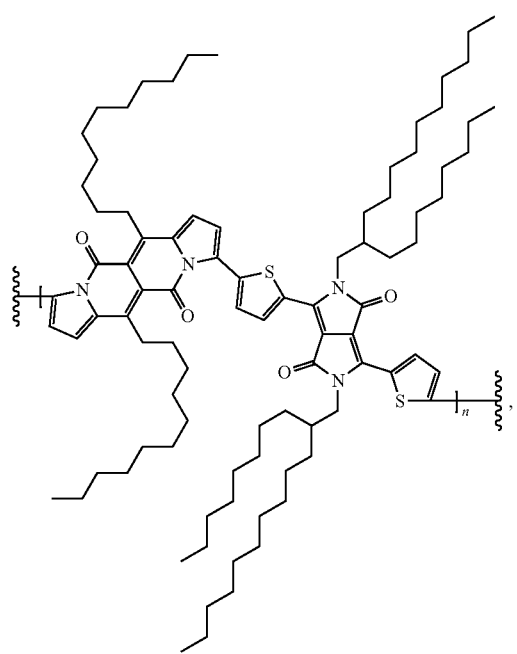

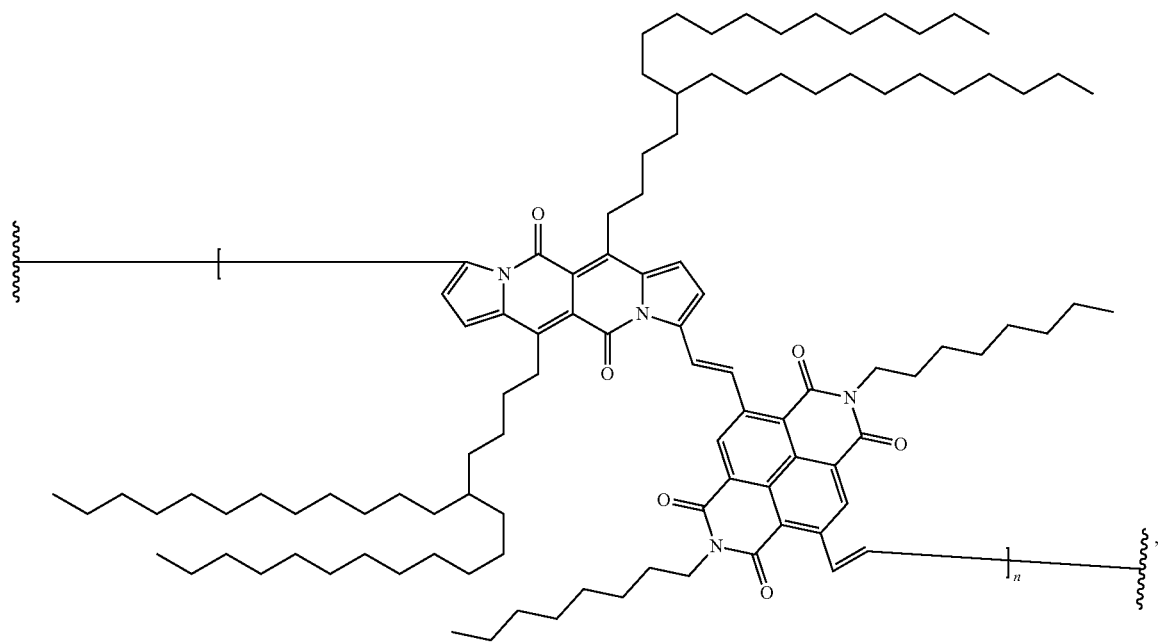
(P-6)
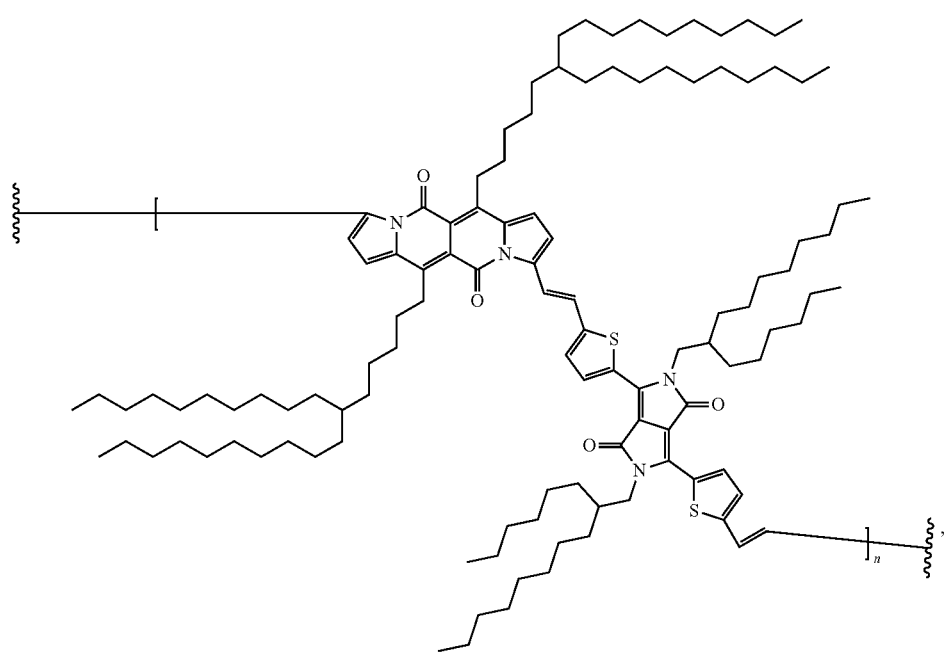
(P-7)

(P-8)
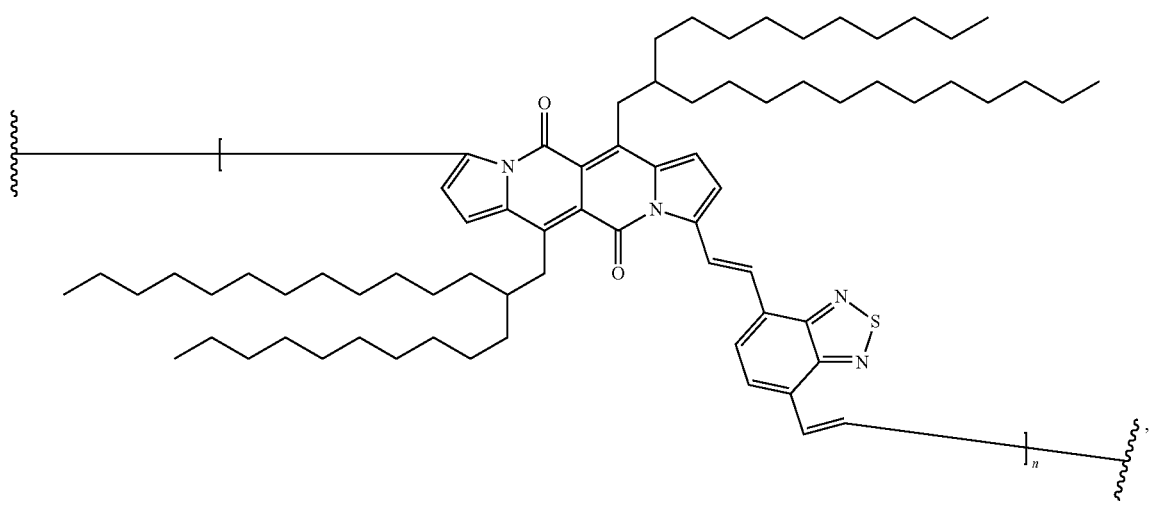
(P-9), or (P-10)
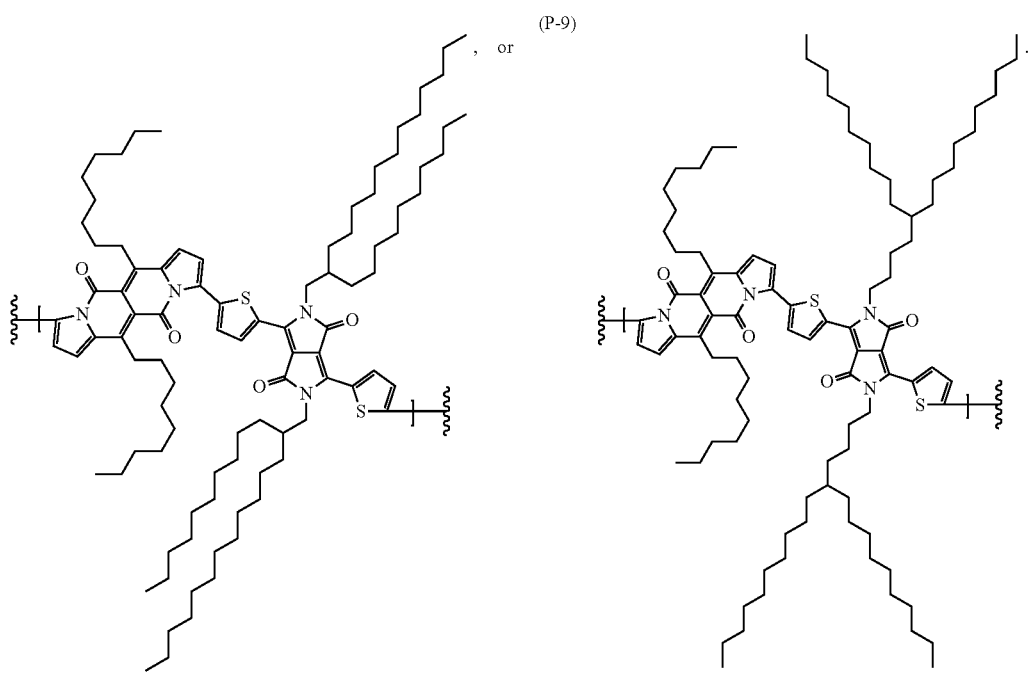

17. An organic semiconductor material, layer or component, comprising a compound according to claim 1.

18. A semiconductor device, comprising a compound according to claim 1.

19. The semiconductor device according to claim 18, which is an organic photovoltaic device, a photodiode, or an organic field effect transistor.

20. A process for the preparation of an organic semiconductor device, which process comprises applying a solution and/or dispersion of a compound according to claim 1 in an organic solvent to a suitable substrate and removing the solvent.

21. A PV device, photodiode, IR absorber, or organic filed effect transistor, comprising the compound according to claim 1.

22. A compound of formula $$X^6\text{—Ar—Y—Ar'—}X^{6'} \quad (X),$$

wherein

Y, Ar and Ar' are defined in claim 1, and $X^6$ and $X^{6'}$ are independently of each other halogen, $ZnX^{12}$, $-SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom; or $-OS(O)_2CF_3$, $-OS(O)_2$-aryl, $-OS(O)_2CH_3$, $-B(OH)_2$, $-B(OY^1)_2$,

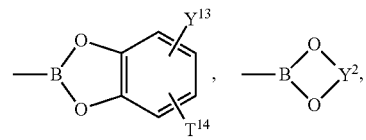

—BF$_4$Na, or —BF$_4$K, wherein $Y^1$ is independently in each occurrence a $C_1$-$C_{10}$alkyl group, $Y^2$ is independently in each occurrence a $C_2$-$C_{10}$ alkylene group, which can optionally be substituted by one, or more $C_1$-$C_8$alkyl groups, and $Y^{13}$ and $Y^{14}$ are independently of each other hydrogen, or a $C_1$-$C_{10}$alkyl group.

23. The compound according to claim 22, which is a compound of formula

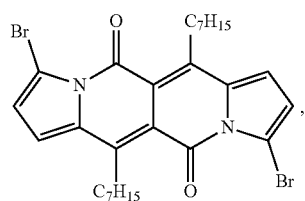
(C-1)

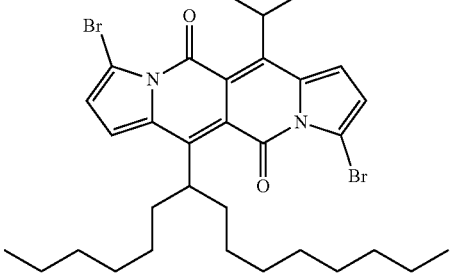
(C-2)

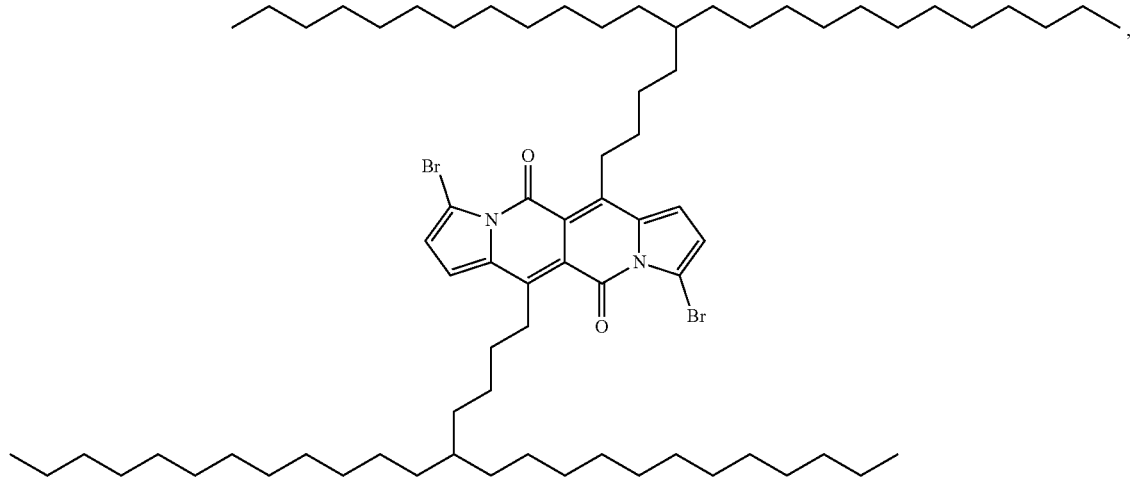
(C-3)

-continued

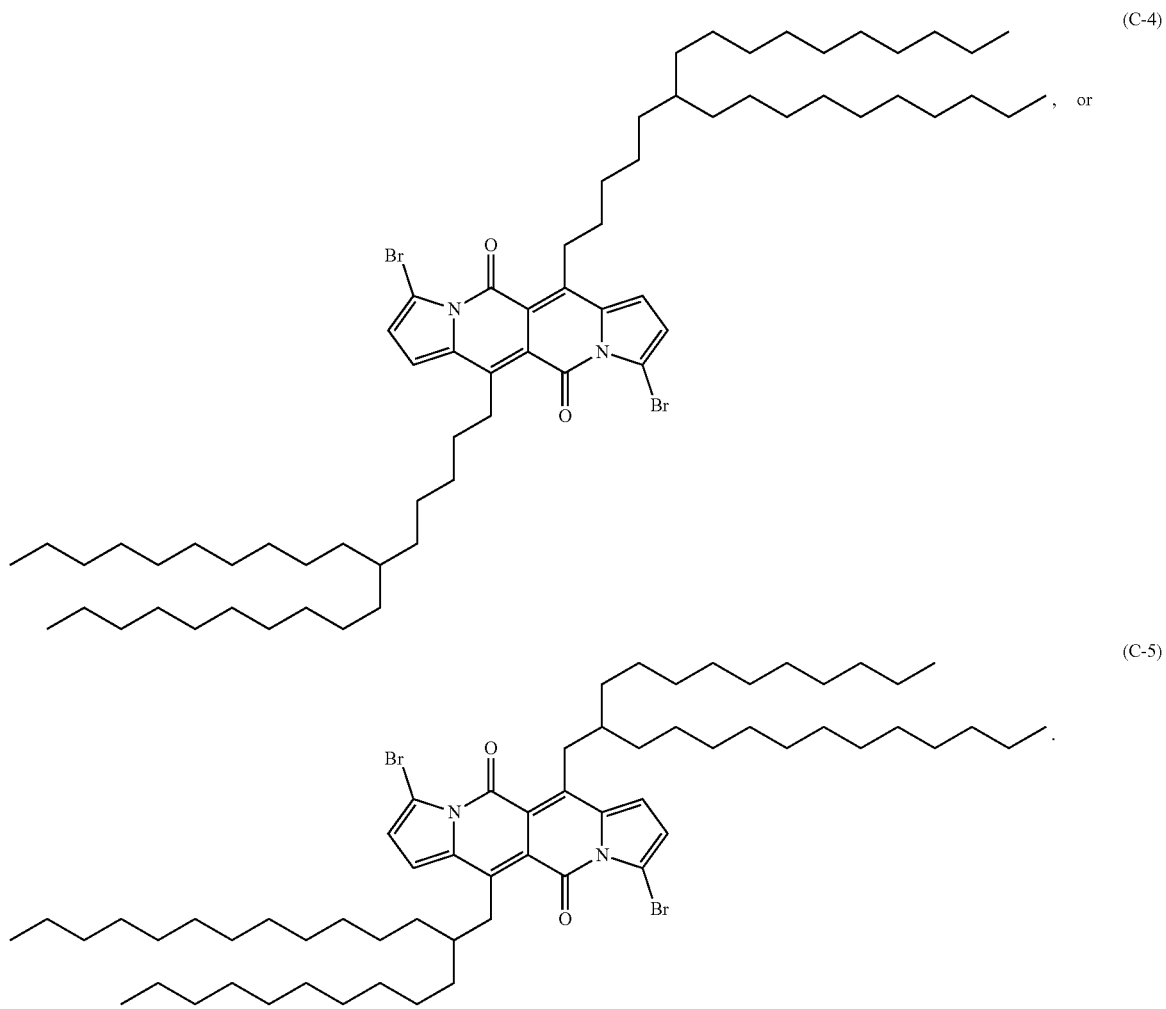

24. A process for producing a compound of formula

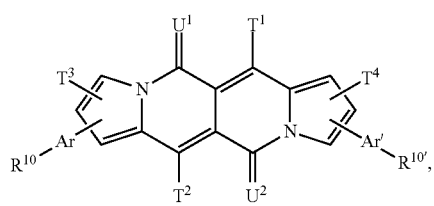

which process comprises
(a) reacting a compound of formula

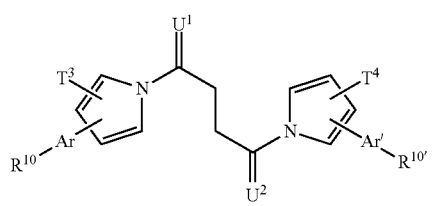

with a compound of formula T₁COOH (XIIa) and a compound of formula T²COOH (XIIb), or a compound of formula T₁COOH (XIIa)

in a solvent in the presence of an acid and/or an acid anhydride, wherein $T^1$, $T^2$, $T^3$, $T^4$, $U^1$, $U^2$, Ar, Ar', $R^{10}$ and $R^{10'}$ are defined in claim 1 and when compound of formula (XI) is reacted only with a compound of formula (XIIa), $T^2$ in formula (Ia) has the meaning of $T^1$.

* * * * *

UNITED STATES PATENT AND TRADEMARK OFFICE
CERTIFICATE OF CORRECTION

PATENT NO. : 10,442,888 B2
APPLICATION NO. : 15/765525
DATED : October 15, 2019
INVENTOR(S) : Marek Grzybowski et al.

Page 1 of 9

It is certified that error appears in the above-identified patent and that said Letters Patent is hereby corrected as shown below:

On the Title Page

Column 1, item (54), title, Line 2, "[2,6]" should read -- [2-6] --.

Column 1, item (72), Inventors, Line 5, "Hofstettn" should read -- Hofstetten --.

In the Specification

Column 1, Line 2, "[2,6]" should read -- [2-6] --.

Column 2, Line 44 (approx.), "(III)" should read -- (II) --.

Column 3, Line 28 (approx.), "(III)" should read -- (II) --.

Column 7, Lines 48-56 (approx.),

"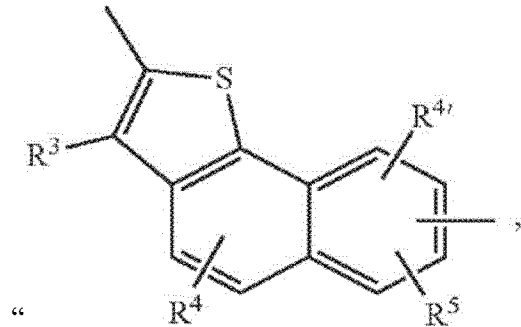" should (XIIc)

Signed and Sealed this
Seventh Day of July, 2020

Andrei Iancu
*Director of the United States Patent and Trademark Office*

CERTIFICATE OF CORRECTION (continued)
U.S. Pat. No. 10,442,888 B2 read --

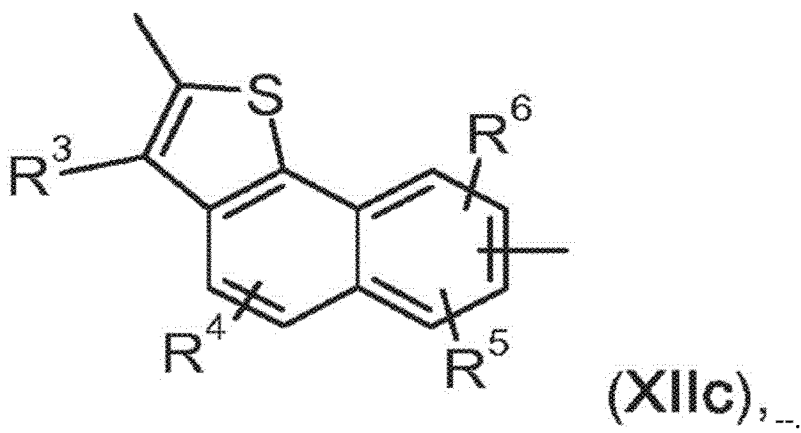

Column 10, Lines 2-14 (approx.),

"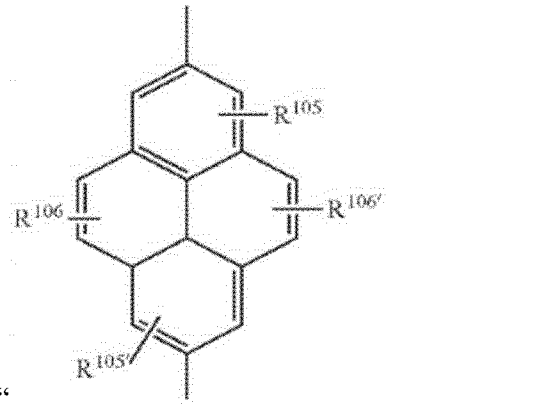" should read

-- 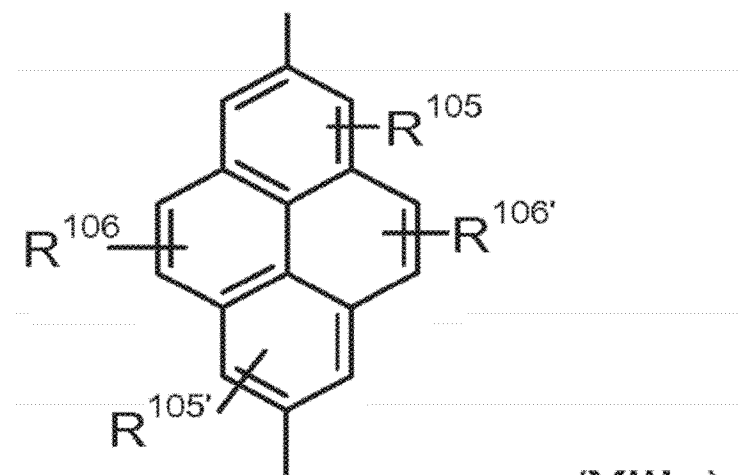 --

Column 14, Line 65, "$C_1$-$C_{18}$alkylthio, $C_1$-$C_{18}$alkoxy," should read -- $C_1$-$C_8$alkylthio, $C_1$-$C_8$alkoxy, --.

Column 16, Line 4 (approx.), "FIGURE" should read -- figure --.

CERTIFICATE OF CORRECTION (continued)
U.S. Pat. No. 10,442,888 B2

Column 21, Lines 11-23 (approx.),

" 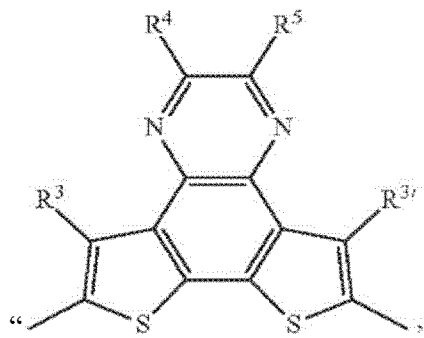 " should read -- 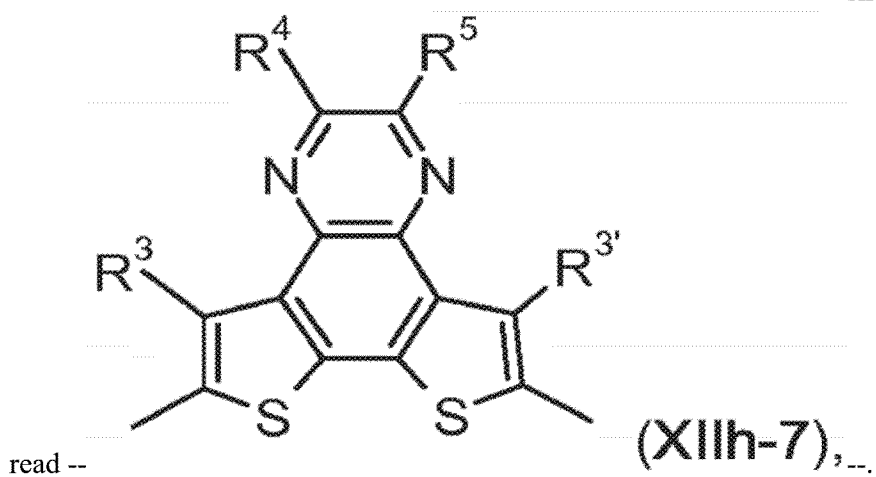 --.

Column 23, Line 53 (approx.), "preferabl" should read -- preferably --.

Column 26, Lines 3-10 (approx.),

" 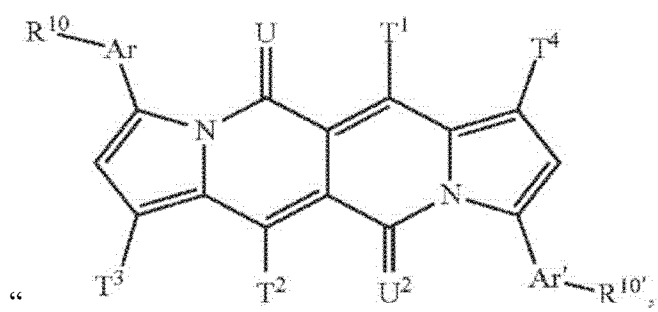 " should

CERTIFICATE OF CORRECTION (continued)
U.S. Pat. No. 10,442,888 B2

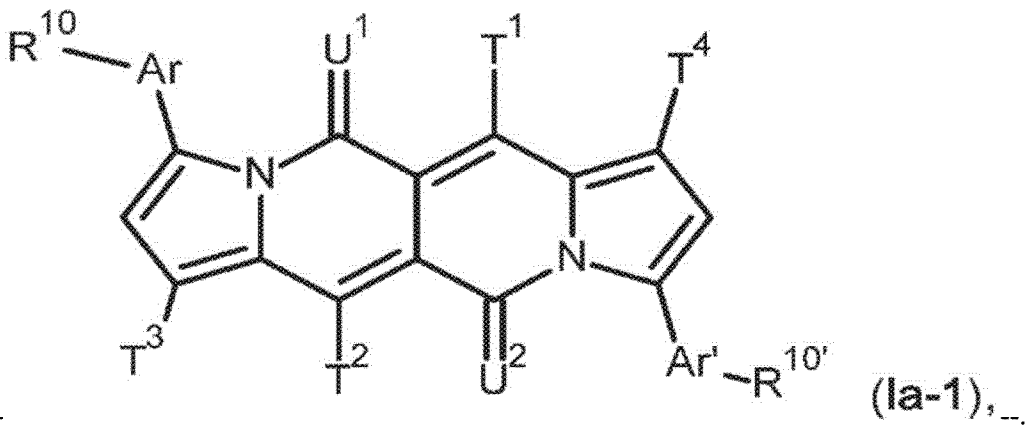

read --

Column 27, Line 33, "$C_6$-$C_8$aryl;" should read -- $C_6$-$C_{18}$aryl; --.

Column 28, Line 64, "$C_1$-$C_1$alkoxy;" should read -- $C_1$-$C_{18}$alkoxy; --.

Column 35, Line 3, "etc.)" should read -- etc.). --.

Column 40, Line 67, "or S–." should read -- or –S–. --.

Column 47, Lines 15-16, "sythesized" should read -- synthesized --.

Column 49, Line 32, "sec.-butyl," should read -- sec-butyl, --;
    Line 32, "tert.-butyl," should read -- tert-butyl, --;
    Line 41, "sec.-butyl," should read -- sec-butyl, --.

Column 49, Line 41, "tert.-butyl," should read -- tert-butyl, --;
    Lines 45-46, "sec.-butyl," should read -- sec-butyl, --;
    Line 46, "tert.-butyl." should read -- tert-butyl. --.

Column 49, Line 62, "tetracosyn" should read -- tetracosyl --.

Column 50, Line 61, "sec.-butoxy," should read -- sec-butoxy, --;
    Line 62, "tert.-butoxy," should read -- tert-butoxy, --;
    Line 66, "sec.-butoxy," should read -- sec-butoxy, --;
    Line 66, "tert.-butoxy," should read -- tert-butoxy, --.

Column 52, Line 58, "WO009/047104," should read -- WO09/047104, --.

Column 56, Line 16 (approx.), "[Apparatus:" should read -- Apparatus: --;
    Line 46 (approx.), "[1,2-b:1,2'-g]" should read -- [1,2-b:1',2'-g] --;
    Line 48, "fromylpyrrole" should read -- formylpyrrole --.

Column 61, Line 67, "C–($CH_3$)" should read -- CH($CH_3$) --.

Column 62, Line 42, "N, 5.88" should read -- N, 5.88; --.

Column 63, Line 65 (approx.), "[b]Propionic" should read -- [b] Propionic --.
    Line 66 (approx.), "[c]0.5" should read -- [c] 0.5 --;
    Line 67 (approx.), "[d]5.0" should read -- [d] 5.0 --.

Column 68, Line 2, "$CH_2(CH_2)_5CH$)." should read -- $CH_2(CH_2)_5CH_3$). --;
    Line 36, "succinylchloride" should read -- succinyl chloride --.

Column 71, Line 5, "cynanostyrene" should read -- cyanosryrene --;
    Line 21, "(EI)" should read -- (El) --;
    Line 22, "[M'+]," should read -- [M+], --;
    Line 66 (approx.), "(EI)" should read -- (El) --;
    Line 67 (approx.), "[M'+]," should read -- [M+], --.

Column 75, Lines 44-47 (approx.),

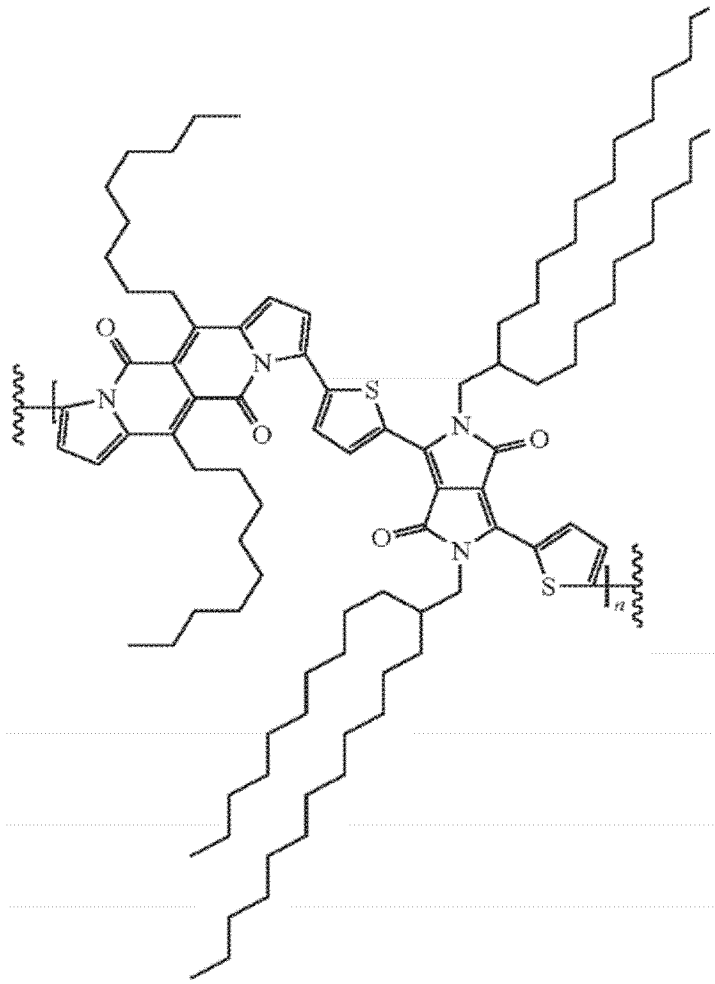

" P-9 " should

CERTIFICATE OF CORRECTION (continued)
U.S. Pat. No. 10,442,888 B2 read --

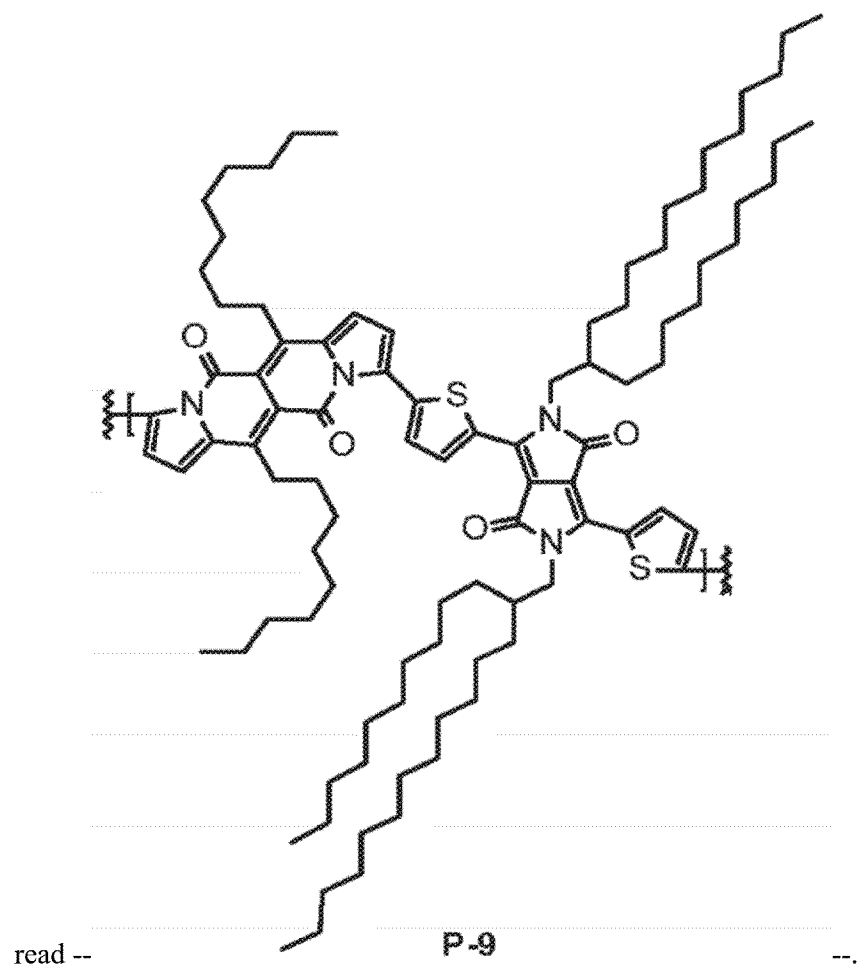

P-9

--.

CERTIFICATE OF CORRECTION (continued)
U.S. Pat. No. 10,442,888 B2

Column 77, Lines 44-47 (approx.), " 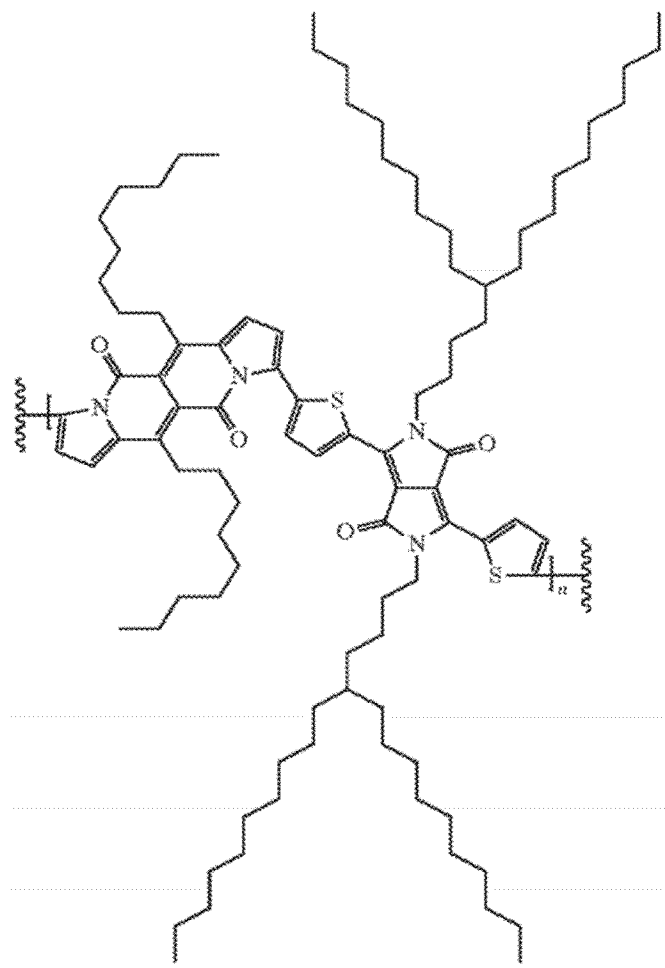 " should read -- 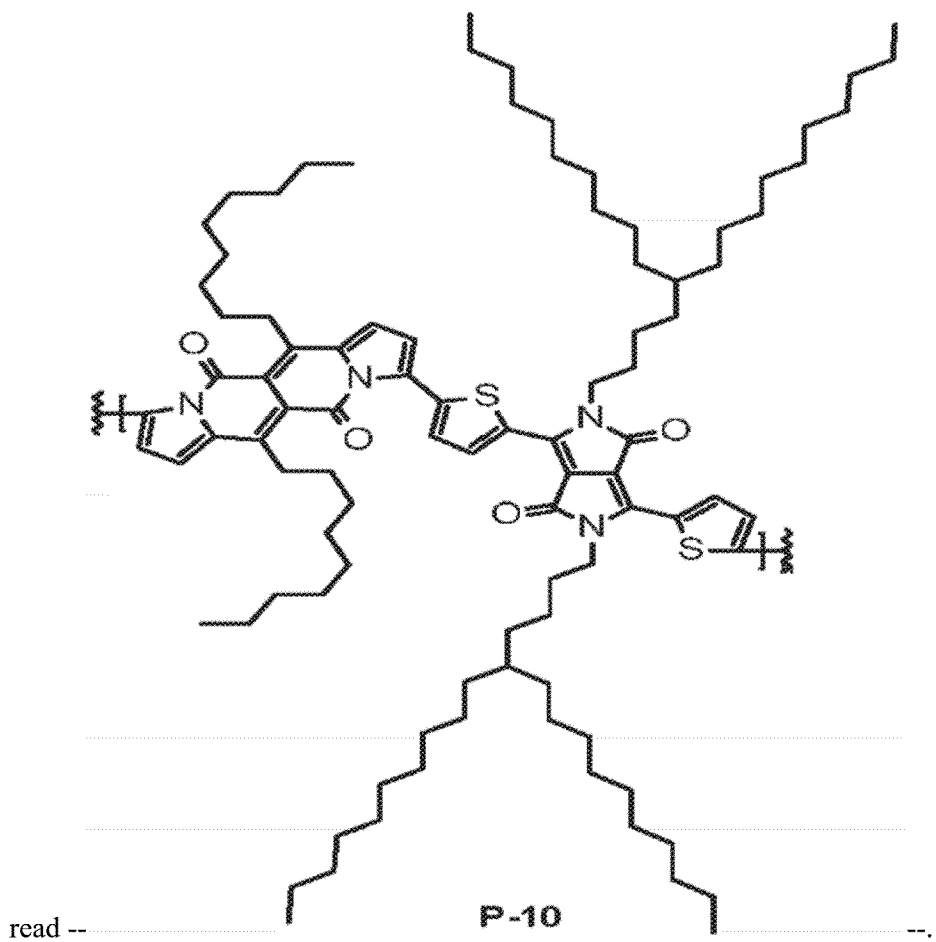 --.

Column 79, Line 3, "Mn" should read -- $M_n$ --.

Column 80, Lines 50-51, "pincoating" should read -- spin-coating --;
   Line 61, "FIGURE" should read -- figure --;
   Line 62, "FIGURE" should read -- figure --;
   Line 66, "FIGURE" should read -- figure --.

In the Claims

Column 89, Line 8, Claim 1, "$C_1$-$C_{25}$arylalkyl;" should read -- $C_7$-$C_{25}$arylalkyl; --.

Column 91, Line 29, Claim 1, "$C_1$-$C_5$alkoxy;" should read -- $C_1$-$C_8$alkoxy; --;
   Line 59, Claim 1, "$C_6$-$C_{15}$aryrl" should read -- $C_6$-$C_{18}$aryl --.

Column 92, Line 37, Claim 1, "$C_1$-$C_8$alkyl," should read -- $C_1$-$C_{18}$alkyl, --.

Column 94, Line 37, Claim 5, "$SiR^{64}$" should read -- $SiR^{164}$ --.

Column 95, Line 57 (approx.), Claim 7, "$U_1$" should read -- $U^1$ --;
   Line 59 (approx.), Claim 7, "$NR^1$" should read -- $NR^{60}$ --.

CERTIFICATE OF CORRECTION (continued)
U.S. Pat. No. 10,442,888 B2

Column 101, Line 45, Claim 9, "–[(Ar)'" should read -- –[(Ar')$_z^1$ --.

Column 105, Line 21, Claim 15, "$C_1$-$C_{52}$alkyl" should read -- $C_1$-$C_{25}$alkyl --.

Column 106, Line 30, Claim 15, "$C_6$-$C_{15}$aryl" should read -- $C_6$-$C_{18}$aryl --.

Column 113, Line 13, Claim 21, "filed" should read -- field --.

Column 116, Line 45, Claim 24, "$T_1COOH$" should read -- $T^1COOH$ --;
    Line 50 (approx.), Claim 24, "$T_1COOH$" should read -- $T^1COOH$ --.